United States Patent
Rothberg et al.

(10) Patent No.: US 9,351,706 B2
(45) Date of Patent: May 31, 2016

(54) INTERCONNECTABLE ULTRASOUND TRANSDUCER PROBES AND RELATED METHODS AND APPARATUS

(71) Applicant: Butterfly Network, Inc., Guilford, CT (US)

(72) Inventors: Jonathan M. Rothberg, Guilford, CT (US); Keith G. Fife, Palo Alto, CA (US); Nevada J. Sanchez, Guilford, CT (US); Tyler S. Ralston, Clinton, CT (US); Gregory L. Charvat, Guilford, CT (US); Gregory Corteville, Madison, CT (US)

(73) Assignee: Butterfly Network, Inc., Guilford, CT (US)

( * ) Notice: Subject to any disclaimer, the term of this patent is extended or adjusted under 35 U.S.C. 154(b) by 0 days.

(21) Appl. No.: 14/561,504

(22) Filed: Dec. 5, 2014

(65) Prior Publication Data

US 2015/0080724 A1 Mar. 19, 2015

Related U.S. Application Data

(63) Continuation of application No. 14/337,813, filed on Jul. 22, 2014.

(60) Provisional application No. 61/857,682, filed on Jul. 23, 2013.

(51) Int. Cl.
*A61B 8/00* (2006.01)
*A61B 8/13* (2006.01)
(Continued)

(52) U.S. Cl.
CPC .............. *A61B 8/4483* (2013.01); *A61B 8/13* (2013.01); *A61B 8/14* (2013.01); *A61B 8/4444* (2013.01);
(Continued)

(58) Field of Classification Search
CPC ............. H02N 1/00; A61H 1/00; A61H 5/00; A61B 8/00; A61B 8/14; A61B 8/4483; G01N 29/00
USPC ........................................................ 600/459
See application file for complete search history.

(56) References Cited

U.S. PATENT DOCUMENTS

| 4,594,662 A | 6/1986 | Devaney |
| 5,269,307 A | 12/1993 | Fife et al. |

(Continued)

FOREIGN PATENT DOCUMENTS

| WO | WO 2007/095499 A2 | 8/2007 |
| WO | WO 2007/096636 A1 | 8/2007 |

(Continued)

OTHER PUBLICATIONS

U.S. Appl. No. 14/561,328, filed Dec. 5, 2014, Rothberg et al.

(Continued)

*Primary Examiner* — Tse Chen
*Assistant Examiner* — Charles G Chiang
(74) *Attorney, Agent, or Firm* — Wolf, Greenfield & Sacks, P.C.

(57) ABSTRACT

Ultrasound devices and methods are described, including a repeatable ultrasound transducer probe having ultrasonic transducers and corresponding circuitry. The repeatable ultrasound transducer probe may be used individually or coupled with other instances of the repeatable ultrasound transducer probe to create a desired ultrasound device. The ultrasound devices may optionally be connected to various types of external devices to provide additional processing and image rendering functionality.

15 Claims, 46 Drawing Sheets

(51) Int. Cl.

| | | |
|---|---|---|
| *A61B 8/08* | (2006.01) | |
| *G03B 27/42* | (2006.01) | |
| *G03B 27/52* | (2006.01) | |
| *B06B 1/02* | (2006.01) | |
| *G01S 7/00* | (2006.01) | |
| *A61B 8/14* | (2006.01) | |
| *A61N 7/02* | (2006.01) | |
| *G01S 7/52* | (2006.01) | |
| *G01S 15/89* | (2006.01) | |
| *A61N 7/00* | (2006.01) | |

(52) U.S. Cl.
CPC ............. *A61B 8/4477* (2013.01); *A61B 8/4488* (2013.01); *A61B 8/4494* (2013.01); *A61B 8/483* (2013.01); *A61B 8/5207* (2013.01); *A61B 8/54* (2013.01); *A61B 8/56* (2013.01); *A61N 7/02* (2013.01); *B06B 1/0292* (2013.01); *G01S 7/003* (2013.01); *G01S 7/5208* (2013.01); *G01S 7/52084* (2013.01); *G01S 15/8915* (2013.01); *G03B 27/423* (2013.01); *G03B 27/52* (2013.01); *A61B 8/4411* (2013.01); *A61N 2007/0078* (2013.01); *Y10T 29/49005* (2015.01)

(56) References Cited

U.S. PATENT DOCUMENTS

| | | | |
|---|---|---|---|
| 5,740,805 A | 4/1998 | Dolazza et al. | |
| 5,782,769 A | 7/1998 | Hwang et al. | |
| 5,817,024 A | 10/1998 | Ogle et al. | |
| 5,893,363 A | 4/1999 | Little et al. | |
| 6,135,961 A | 10/2000 | Pflugrath et al. | |
| 6,203,498 B1 | 3/2001 | Bunce et al. | |
| D456,509 S | 4/2002 | Schultz | |
| 6,364,839 B1 | 4/2002 | Little et al. | |
| 6,371,918 B1 | 4/2002 | Bunce | |
| 6,383,139 B1 | 5/2002 | Hwang et al. | |
| 6,416,475 B1 | 7/2002 | Hwang et al. | |
| D461,895 S | 8/2002 | Barnes et al. | |
| 6,430,109 B1 | 8/2002 | Khuri-Yakub et al. | |
| 6,443,901 B1 | 9/2002 | Fraser | |
| 6,447,451 B1 | 9/2002 | Wing et al. | |
| 6,471,651 B1 | 10/2002 | Hwang et al. | |
| 6,569,101 B2 | 5/2003 | Quistgaard et al. | |
| 6,575,908 B2 | 6/2003 | Barnes et al. | |
| 6,604,630 B1 | 8/2003 | Cabatic et al. | |
| 6,632,178 B1 | 10/2003 | Fraser | |
| 6,645,145 B1 | 11/2003 | Dreschel et al. | |
| 6,648,826 B2 | 11/2003 | Little et al. | |
| 6,659,954 B2 | 12/2003 | Robinson | |
| 6,694,817 B2 | 2/2004 | Degertekin et al. | |
| 6,795,374 B2 | 9/2004 | Barnes et al. | |
| 6,831,294 B1 | 12/2004 | Nishimura et al. | |
| 6,831,394 B2 | 12/2004 | Baumgartner et al. | |
| 6,835,177 B2 | 12/2004 | Fritz et al. | |
| 6,865,140 B2 | 3/2005 | Thomenius et al. | |
| 6,880,137 B1 | 4/2005 | Burlison et al. | |
| 6,958,255 B2 | 10/2005 | Khuri-Yakub et al. | |
| 6,962,566 B2 | 11/2005 | Quistgaard et al. | |
| 6,974,417 B2 | 12/2005 | Lockwood et al. | |
| 7,030,536 B2 * | 4/2006 | Smith .................... | H02N 1/006 310/309 |
| 7,037,746 B1 | 5/2006 | Smith et al. | |
| 7,052,464 B2 | 5/2006 | Wodnicki | |
| 7,125,383 B2 | 10/2006 | Hoctor et al. | |
| 7,257,051 B2 | 8/2007 | Thomenius et al. | |
| 7,280,435 B2 | 10/2007 | Thomenius et al. | |
| 7,285,897 B2 | 10/2007 | Fisher et al. | |
| 7,293,462 B2 | 11/2007 | Lee et al. | |
| D558,351 S | 12/2007 | Diener et al. | |
| 7,303,530 B2 | 12/2007 | Barnes et al. | |
| 7,313,053 B2 | 12/2007 | Wodnicki | |
| 7,353,056 B2 | 4/2008 | Hazard et al. | |
| 7,375,420 B2 | 5/2008 | Fisher et al. | |
| 7,408,283 B2 | 8/2008 | Smith et al. | |
| 7,425,199 B2 | 9/2008 | Hoctor et al. | |
| 7,441,321 B2 | 10/2008 | Baumgartner et al. | |
| 7,441,447 B2 | 10/2008 | Degertekin et al. | |
| 7,443,765 B2 | 10/2008 | Thomenius et al. | |
| 7,449,640 B2 | 11/2008 | Coleman | |
| 7,451,651 B2 | 11/2008 | Woychik et al. | |
| 7,470,232 B2 | 12/2008 | Hoctor et al. | |
| D591,423 S | 4/2009 | Diener et al. | |
| 7,530,952 B2 | 5/2009 | Huang et al. | |
| 7,534,211 B2 | 5/2009 | Hwang et al. | |
| 7,545,012 B2 | 6/2009 | Smith et al. | |
| 7,546,769 B2 | 6/2009 | Ramaswamy et al. | |
| 7,549,961 B1 | 6/2009 | Hwang | |
| 7,549,962 B2 | 6/2009 | Dreschel et al. | |
| 7,564,172 B1 | 7/2009 | Huang | |
| 7,604,596 B2 | 10/2009 | Hwang et al. | |
| 7,612,483 B2 | 11/2009 | Degertekin | |
| 7,612,635 B2 | 11/2009 | Huang | |
| 7,615,834 B2 | 11/2009 | Khuri-Yakub et al. | |
| 7,622,848 B2 | 11/2009 | Lee et al. | |
| 7,646,133 B2 | 1/2010 | Degertekin | |
| 7,686,766 B2 | 3/2010 | Quistgaard et al. | |
| 7,687,976 B2 | 3/2010 | Haider et al. | |
| 7,740,586 B2 | 6/2010 | Hwang et al. | |
| 7,745,248 B2 | 6/2010 | Park et al. | |
| 7,759,839 B2 | 7/2010 | Huang | |
| 7,764,003 B2 | 7/2010 | Huang | |
| 7,775,979 B2 | 8/2010 | Thomenius et al. | |
| 7,779,696 B2 | 8/2010 | Huang | |
| 7,809,400 B1 | 10/2010 | Hwang | |
| 7,819,807 B2 | 10/2010 | Barnes et al. | |
| 7,824,335 B2 | 11/2010 | Wodnicki | |
| 7,846,102 B2 | 12/2010 | Kupnik et al. | |
| 7,867,168 B2 | 1/2011 | Little et al. | |
| 7,878,977 B2 | 2/2011 | Mo et al. | |
| 7,880,565 B2 | 2/2011 | Huang | |
| 7,888,709 B2 | 2/2011 | Lemmerhirt et al. | |
| 7,892,176 B2 | 2/2011 | Wodnicki et al. | |
| 7,898,905 B2 | 3/2011 | Wodnicki et al. | |
| 7,952,260 B2 | 5/2011 | Haider et al. | |
| 7,954,387 B1 | 6/2011 | Furlong | |
| 7,955,264 B2 | 6/2011 | Mathew et al. | |
| 7,956,510 B2 | 6/2011 | Huang | |
| 7,978,461 B2 | 7/2011 | Diener et al. | |
| 7,996,688 B2 | 8/2011 | Little et al. | |
| 8,004,373 B2 | 8/2011 | Huang | |
| 8,008,105 B2 | 8/2011 | Huang | |
| 8,008,835 B2 | 8/2011 | Degertekin | |
| 8,018,301 B2 | 9/2011 | Huang | |
| 8,038,620 B2 | 10/2011 | Lee et al. | |
| 8,052,606 B2 | 11/2011 | Barnes et al. | |
| 8,066,642 B1 | 11/2011 | Little et al. | |
| 8,105,941 B2 | 1/2012 | Huang | |
| 8,120,229 B2 | 2/2012 | Huang | |
| 8,128,050 B1 | 3/2012 | Sliger | |
| 8,133,182 B2 | 3/2012 | Wagner | |
| 8,137,278 B2 | 3/2012 | Lundberg et al. | |
| D657,361 S | 4/2012 | Goodwin et al. | |
| 8,176,787 B2 | 5/2012 | Haider et al. | |
| 8,197,413 B2 * | 6/2012 | Kurse .................... | A61B 8/12 29/594 |
| 8,199,685 B2 | 6/2012 | Hwang | |
| 8,203,912 B2 | 6/2012 | Roest et al. | |
| 8,213,467 B2 | 7/2012 | Little et al. | |
| 8,216,146 B2 | 7/2012 | Hwang et al. | |
| 8,222,065 B1 | 7/2012 | Smeys et al. | |
| 8,226,563 B2 | 7/2012 | Petersen et al. | |
| 8,237,601 B2 | 8/2012 | Dunbar et al. | |
| 8,242,665 B2 | 8/2012 | Robinson et al. | |
| 8,247,945 B2 | 8/2012 | Huang | |
| 8,298,144 B2 | 10/2012 | Burcher | |
| 8,309,428 B2 | 11/2012 | Lemmerhirt et al. | |
| 8,315,125 B2 | 11/2012 | Lemmerhirt et al. | |
| 8,327,521 B2 | 12/2012 | Dirksen et al. | |
| 8,345,508 B2 | 1/2013 | Wodnicki et al. | |
| 8,345,513 B2 | 1/2013 | Huang | |
| 8,355,554 B2 | 1/2013 | Ma et al. | |
| 8,363,514 B2 | 1/2013 | Huang | |

(56) References Cited

U.S. PATENT DOCUMENTS

| | | | |
|---|---|---|---|
| 8,372,011 B2 | 2/2013 | Degertekin | |
| 8,388,544 B2 | 3/2013 | Hoctor et al. | |
| 8,398,408 B1 | 3/2013 | Hansen et al. | |
| 8,398,554 B2 | 3/2013 | Degertekin | |
| 8,399,278 B2 | 3/2013 | Lemmerhirt et al. | |
| 8,402,831 B2 | 3/2013 | Kupnik et al. | |
| 8,409,095 B1 | 4/2013 | Marquis | |
| 8,429,808 B2 | 4/2013 | Huang | |
| 8,439,840 B1 | 5/2013 | Duffy | |
| 8,451,693 B2 | 5/2013 | Nikoozadeh et al. | |
| 8,461,978 B2 | 6/2013 | Garner et al. | |
| 8,483,014 B2 | 7/2013 | Huang | |
| 8,526,271 B2 | 9/2013 | Huang | |
| 8,527,033 B1 | 9/2013 | Williams et al. | |
| 8,559,274 B2 | 10/2013 | Huang | |
| 8,563,345 B2 | 10/2013 | Adler et al. | |
| 8,647,279 B2 | 2/2014 | Daft et al. | |
| 8,658,453 B2 | 2/2014 | Lemmerhirt et al. | |
| 8,672,850 B1 | 3/2014 | Miller | |
| 8,689,606 B2 | 4/2014 | Schellekens et al. | |
| 8,804,457 B2 | 8/2014 | Franchini et al. | |
| 2001/0039389 A1* | 11/2001 | Sakurai | A61B 17/320068 601/2 |
| 2002/0177774 A1 | 11/2002 | Hwang et al. | |
| 2003/0114760 A1* | 6/2003 | Robinson | B06B 1/0685 600/459 |
| 2003/0205947 A1* | 11/2003 | Klee | B06B 1/0688 310/311 |
| 2005/0171431 A1* | 8/2005 | Petersen | B06B 1/0223 600/437 |
| 2005/0177045 A1 | 8/2005 | Degertekin et al. | |
| 2005/0240127 A1* | 10/2005 | Seip | A61N 7/02 601/2 |
| 2007/0239019 A1 | 10/2007 | Richard et al. | |
| 2007/0242567 A1 | 10/2007 | Daft et al. | |
| 2007/0276238 A1 | 11/2007 | Sudol | |
| 2008/0194053 A1 | 8/2008 | Huang | |
| 2008/0290756 A1 | 11/2008 | Huang | |
| 2008/0296708 A1 | 12/2008 | Wodnicki et al. | |
| 2009/0134497 A1 | 5/2009 | Barth et al. | |
| 2009/0142872 A1 | 6/2009 | Park et al. | |
| 2009/0240148 A1* | 9/2009 | Jeong | A61B 8/4483 600/439 |
| 2009/0250729 A1* | 10/2009 | Lemmerhirt | A61B 8/00 257/254 |
| 2010/0063397 A1 | 3/2010 | Wagner | |
| 2010/0152587 A1* | 6/2010 | Haider | A61B 8/00 600/459 |
| 2010/0191894 A1* | 7/2010 | Bartley | G06F 11/201 711/5 |
| 2010/0225200 A1 | 9/2010 | Kupnik et al. | |
| 2010/0256488 A1* | 10/2010 | Kim | B06B 1/0633 600/439 |
| 2010/0317972 A1* | 12/2010 | Baumgartner | G10K 11/002 600/459 |
| 2011/0071397 A1 | 3/2011 | Wodnicki et al. | |
| 2011/0084570 A1 | 4/2011 | Soeda et al. | |
| 2011/0218436 A1 | 9/2011 | Dewey et al. | |
| 2011/0272693 A1 | 11/2011 | Kobayashi et al. | |
| 2012/0022379 A1 | 1/2012 | Gubbini et al. | |
| 2012/0074509 A1 | 3/2012 | Berg et al. | |
| 2012/0289829 A1 | 11/2012 | Barnes et al. | |
| 2013/0116561 A1 | 5/2013 | Rothberg et al. | |
| 2013/0169110 A1* | 7/2013 | Jeong | B06B 1/0292 310/314 |
| 2014/0066763 A2 | 3/2014 | Rothberg et al. | |
| 2014/0217478 A1 | 8/2014 | Rothberg et al. | |
| 2014/0219062 A1 | 8/2014 | Rothberg et al. | |
| 2014/0264660 A1 | 9/2014 | Rothberg et al. | |
| 2014/0288428 A1 | 9/2014 | Rothberg et al. | |
| 2015/0032002 A1 | 1/2015 | Rothberg et al. | |
| 2015/0087977 A1 | 3/2015 | Rothberg et al. | |

FOREIGN PATENT DOCUMENTS

| | | |
|---|---|---|
| WO | WO 2012/017978 A2 | 2/2012 |
| WO | WO 2014/151362 A2 | 9/2014 |

OTHER PUBLICATIONS

U.S. Appl. No. 14/561,384, filed Dec. 5, 2014, Rothberg et al.
PCT/US2014/047553, Nov. 26, 2014, Invitation to Pay Additional Fees.
U.S. Appl. No. 14/208,281, filed Mar. 13, 2014, Rothberg et al.
U.S. Appl. No. 14/208,351, filed Mar. 13, 2014, Rothberg et al.
U.S. Appl. No. 14/337,813, filed Jul. 22, 2014, Rothberg et al.
PCT/US2014/025567, Jul. 2, 2014, Invitation to Pay Additional Fees.
PCT/US2014/025567, Sep. 15, 2014, International Search Report and Written Opinion.
Invitation to Pay Additional Fees mailed Jul. 2, 2014 for Application No. PCT/US2014/025567.
International Search Report and Written Opinion mailed Sep. 15, 2014 for Application No. PCT/U52014/025567.
[No Author Listed], Technical Publications: Vscan Version 1.x.x CE0470 User manual GM092102. Revision 05. GE Healthcare. 2011. Chapters 1-5. 81 pages.
[No Author Listed], Universal Series Bus 3.0 Specification. Revision 1.0. Hewlett-Packard Company, Intel Corporation, Microsoft Corporation, NEC Corporation, STEricsson, and Texas Instruments. Jun. 6, 2011. 531 pages.
Agarwal et al., Single-Chip Solution for Ultrasound Imaging Systems: Initial Results. 2007 IEEE Ultrasonics Symposium. Oct. 1, 2007;1563-6.
Bavaro et al., Element Shape Design of 2-D CMUT Arrays for Reducing Grating Lobes. IEEE Trans Ultrason Ferroelectr Freq Contr. Feb. 2008;55(2):308-18.
Calmes et al., Highly Integrated 2-D Capacitive Micromachined Ultrasonic Transducers. 1999 IEEE Ultrason Symp. 1999;1163-6.
Chen et al., Ultrasonic Imaging Front-End Design for CMUT: A 3-Level 30Vpp Pulse-Shaping Pulser with Improved Efficiency and a Noise-Optimized Receiver. IEEE Asian Solid-State Circuits Conference. Nov. 12-14, 2012;173-6.
Cheng et al., An Efficient Electrical Addressing Method Using Through-Wafer Vias for Two-Dimensional Ultrasonic Arrays. 2000 IEEE Ultrasonics Symposium. 2000;2:1179-82.
Cheng et al., CMUT-in-CMOS ultrasonic transducer arrays with on-chip electronics. Transducers 2009. IEEE. Jun. 21, 2009;1222-5.
Cheng et al., Electrical Through-Wafer Interconnects with Sub-PicoFarad Parasitic Capacitance. 2001 Microelectromechan Syst Conf. Aug. 24, 2001;18-21.
Daft et al., 5F-3 A Matrix Transducer Design with Improved Image Quality and Acquisition Rate. 2007 IEEE Ultrasonics Symposium. Oct. 1, 2007 ;411-5.
Daft et al., Microfabricated Ultrasonic Transducers Monolithically Integrated with High Voltage Electronics. 2004 IEEE Ultrasonics Symposium. Aug. 23, 2004 ;1:493-6.
Doody et al., Modeling and Characterization of CMOS-Fabricated Capacitive Micromachined Ultrasound Transducers. J Microelectromechan Sys. Feb. 2011;20(1):104-118.
Eccardt et al., Micromachined ultrasound transducers with improved coupling factors from a CMOS compatible process. Ultrasonics. Mar. 2000;38:774-80.
Eccardt et al., Surface micromachined ultrasound transducer in CMOS technology. Proc Ultrason Symp. 1996;959-62.
Gurun et al., Front-end CMOS electronics for monolithic integration with CMUT arrays: circuit design and initial experimental results. Proc Ultrason Symp. 2008;390-3.
Kim et al., Design and Test of a Fully Controllable 64×128 2-D CMUT Array Integrated with Reconfigurable Frontend ASICs for Volumetric Ultrasound Imaging. IEEE. International Ultrasonics Symposium Proceedings. Oct. 7-10, 2012;77-80. doi: 10.1109/ULTSYM.2012.0019.
Knight et al., Low Temperature Fabrication of Immersion Capacitive Micromachined Ultrasonic Transducers on Silicon and Dielectric Substrates. IEEE Trans Ultrason Ferroelectr Freq Contr. Oct. 2004;51(10):1324-33.

(56) References Cited

OTHER PUBLICATIONS

Kupnik et al., CMUT Fabrication Based on a Thick Buried Oxide Layer. Proc IEEE Ultrason Symp. Oct. 2010;2010:547-550. doi:10.1109/ULTSYM.2010.5935935. Epub Jun. 8, 2012. 10 pages.

Kupnik et al., Wafer-Bonded CMUT Meets CMOS. 2010 CMOS Emerging Technology Workshop. May 21, 2010;1-22.

Lin et al., Packaging of Large and Low-Pitch Size 2D Ultrasonic Transducer Arrays. MEMS Conf. 2010;508-11.

Nikoozadeh et al., Forward-Looking Intracardiac Ultrasound Imaging Using a 1-D CMUT Array Integrated With Custom Front-End Electronics. IEEE Trans Ultrason Ferroelectr Freq Contr. Dec. 2008;55(12):2651-60.

Noble et al., A cost-effective and manufacturable route to the fabrication of high-density 2D micromachined ultrasonic transducer arrays and (CMOS) signal conditioning electronics on the same silicon substrate. Proc Ultrason Symp. 2001;941-5.

Noble et al., Low-temperature micromachined CMUTs with fully-integrated analogue front-end electronics. Proc Ultrason Symp. 2002;1045-50.

Oralkan et al., Volumetric Imaging Using 2D Capacitive Micromachined Ultrasonic Transducer Arrays (CMUTs): Initial Results. 2002 IEEE Ultrason Symp. 2002;1083-6.

Oralkan et al., Volumetric Ultrasound Imaging Using 2-D CMUT Arrays. IEEE Trans Ultrason Ferroelectr Freq Contr. Nov. 2003;50(11):1581-94.

Park et al., Fabrication of Capacitive Micromachined Ultrasonic Transducers via Local Oxidation and Direct Wafer Bonding. J Microelectromechan Syst. Feb. 2011;20(1):95-103.

Tsuji et al., Low Temperature Process for CMUT Fabrication with Wafer Bonding Technique. IEEE Intl Ultrason Symp Proc. 2010;551-4.

Um et al., An Analog-Digital-Hybrid Single-Chip RX Beamformer with Non-Uniform Sampling for 2D-CMUT Ultrasound Imaging to Achieve Wide Dynamic Range of Delay and Small Chip Area. IEEE International Solid-State Circuits Conference. Feb. 12, 2014;426-8.

Wodnicki et al., Multi-Row Linear CMUT Array Using CMUTs and Multiplexing Electronics. Proc Ultrason Symp. 2009;2696-9.

Wolffenbuttel et al., Low-temperature silicon wafer-to-wafer bonding using gold at eutectic temperature. Sensors and Actuators A. 1994;43:223-9.

Wygant et al., Integration of 2D CMUT Arrays with Front-End Electronics for Volumetric Ultrasound Imaging. IEEE Trans Ultrason Ferroelectr Freq Contr. Feb. 2008;55(2):327-42.

Zahorian et al., Single chip CMUT arrays with integrated CMOS electronics: fabrication process development and experimental results. Proc Ultrason Symp. 2008;386-9.

Zhuang et al., Wafer-bonded 2-D CMUT arrays incorporating through-wafer trench-isolated interconnects with a supporting frame. IEEE Trans Ultrason Ferroelectr Freq Control. Jan. 2009;56(1):182-92. doi: 10.1109/TUFFC.2009.1018.

International Search Report and Written Opinion mailed Mar. 2, 2015 for Application No. PCT/US2014/047553.

Office Communication and Interview Summary mailed Mar. 26, 2015 for U.S. Appl. No. 14/561,328.

PCT/US2014/047553, Mar. 2, 2015, International Search Report and Written Opinion.

Invitation to Pay Additional Fees mailed Nov. 26, 2014 for Application No. PCT/US2014/047553.

Interview Summary mailed May 7, 2015 for U.S. Appl. No. 14/561,328.

International Preliminary Report on Patentability mailed Sep. 24, 2015 for Application No. PCT/US2014/025567.

Office Communication mailed Aug. 17, 2015 for U.S. Appl. No. 14/561,328.

Khuri-Yakub et al., Miniaturized Ultrasound Imaging Probes Enabled by CMUT Arrays with Integrated Frontend Electronic Circuits. Conf Proc IEEE Eng Med Biol Soc. 2010;1:5987-90. doi:10.1109/IEMBS.2010.5627580. Epub Dec. 6, 2010. 13 pages.

International Preliminary Report on Patentability mailed Feb. 4, 2016 for Application No. PCT/US2014/047553.

PCT/US2014/047553, Feb. 4, 2016, International Preliminary Report on Patentability.

PCT/US2014/025567, Sep. 24, 2015, International Preliminary Report on Patentability.

\* cited by examiner

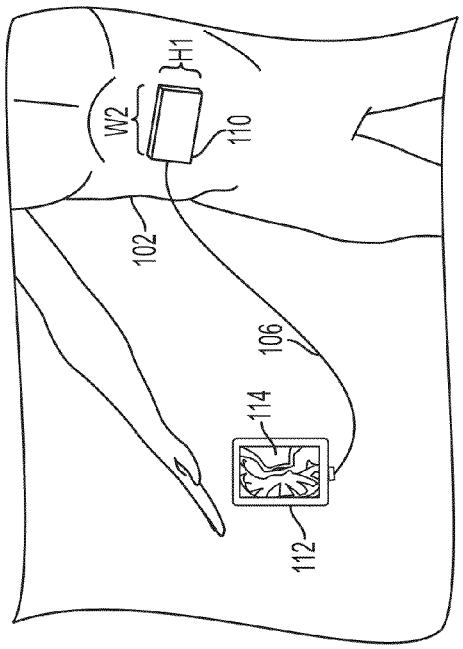
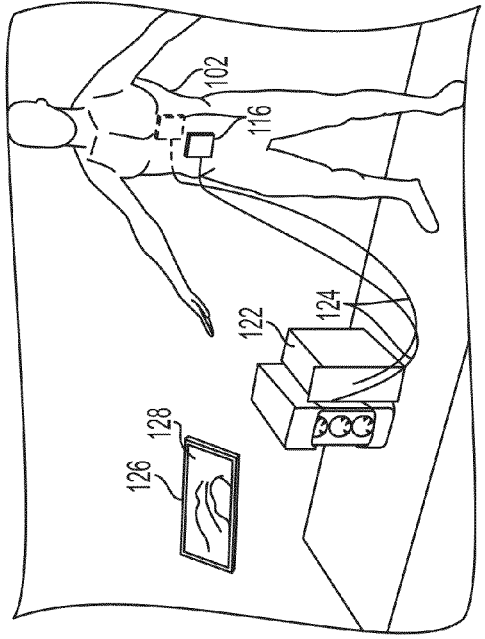
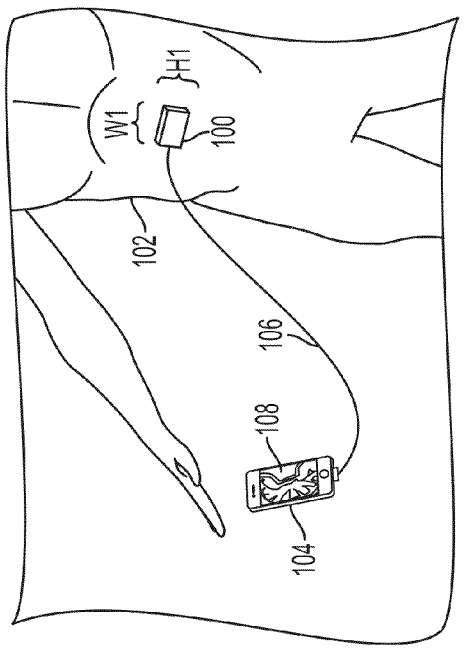

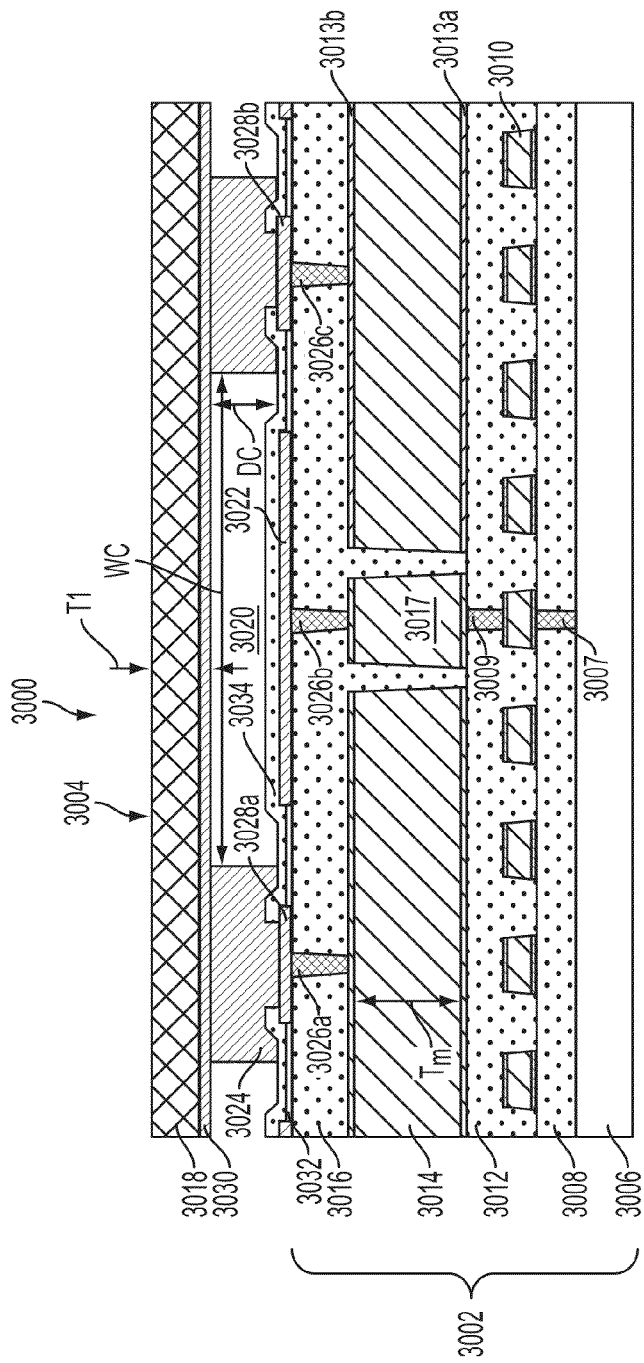
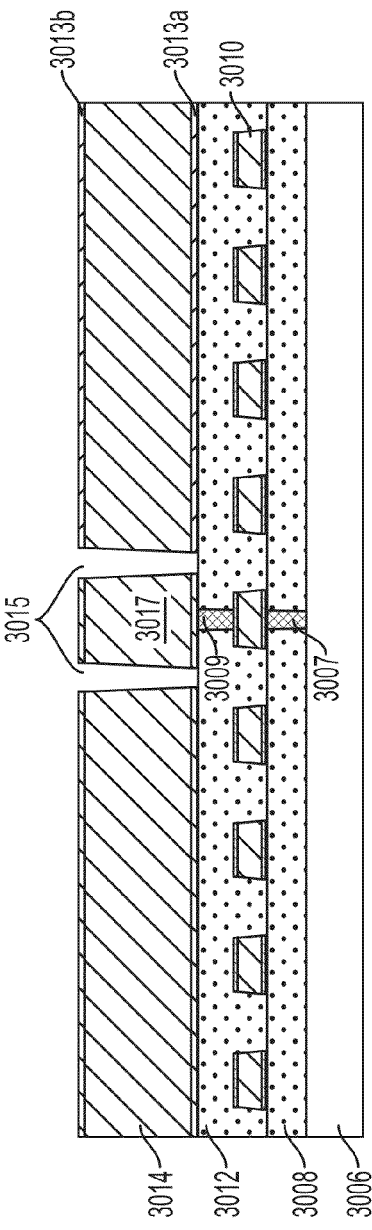
FIG. 30A
FIG. 30B

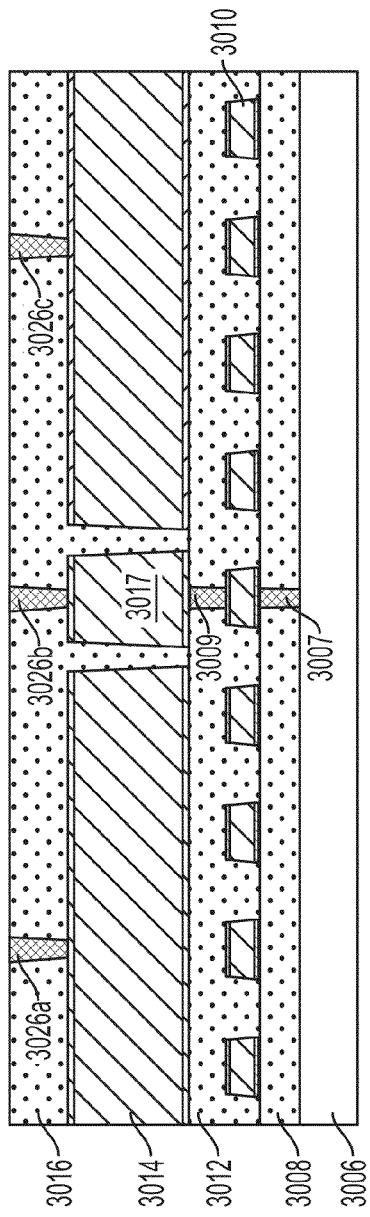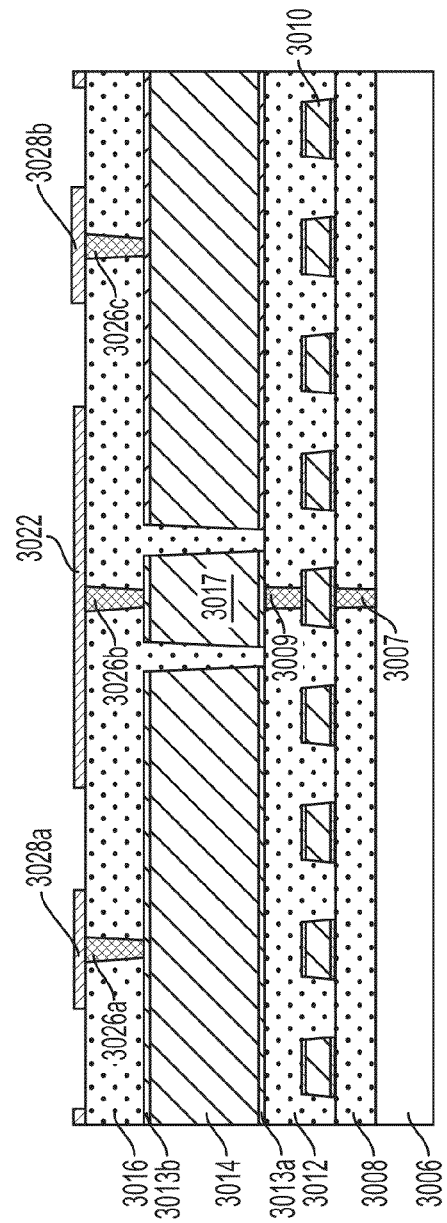

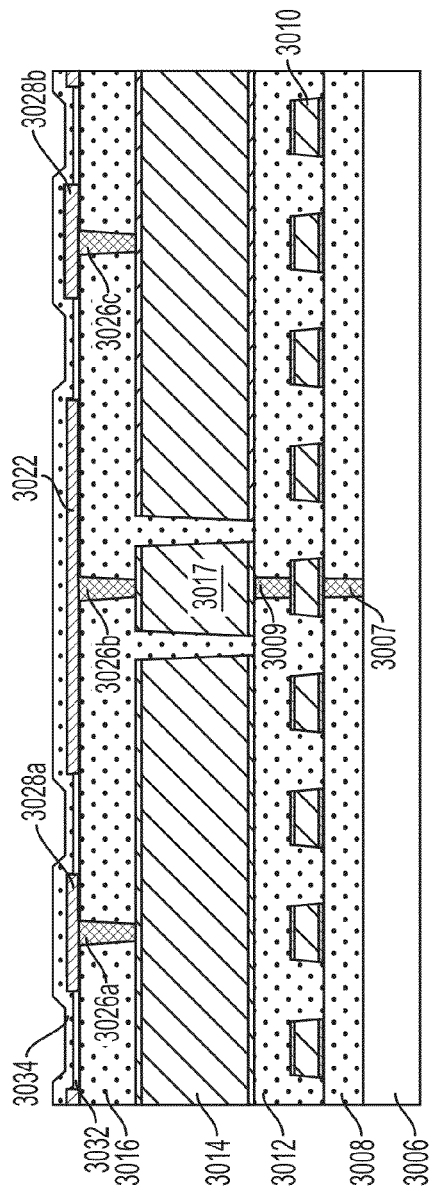
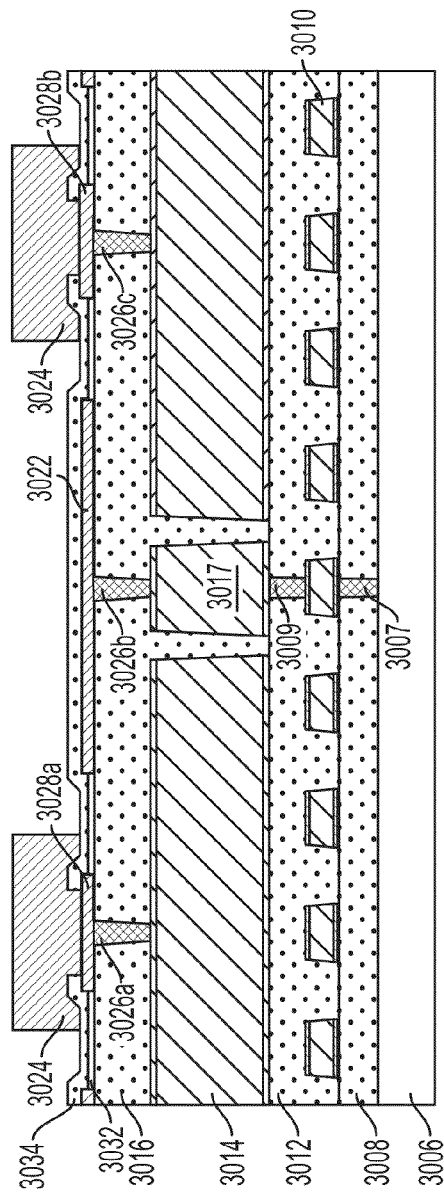
FIG. 30E
FIG. 30F

INTERCONNECTABLE ULTRASOUND TRANSDUCER PROBES AND RELATED METHODS AND APPARATUS

RELATED APPLICATIONS

This application is a continuation of and claims the benefit under 35 U.S.C. §120 of U.S. patent application Ser. No. 14/337,813, filed on Jul. 22, 2014 and entitled "INTERCONNECTABLE ULTRASOUND TRANSDUCER PROBES AND RELATED METHODS AND APPARATUS" which claims the benefit under 35 U.S.C. §119(e) of U.S. Provisional Patent Application Ser. No. 61/857,682, filed on Jul. 23, 2013 and entitled "INTERCONNECTABLE ULTRASOUND TRANSDUCER PROBES AND RELATED METHODS AND APPARATUS", both of which are incorporated herein by reference in their entireties.

BACKGROUND

1. Field

The technology described herein relates to ultrasound devices and related methods and apparatus.

2. Related Art

Ultrasound imaging probes exist. Conventionally, distinct probes are required for imaging in two dimensions (2D) or three dimensions (3D). Separate design and manufacture of such distinct probes are required, which increases cost and limits versatility of the probes.

Also, conventional ultrasound probes are designed for connection to specialized control systems. The probes themselves include transducers but typically lack any control circuitry for controlling operation of the transducers or processing signals received by the transducers. Rather, control of the transducers and processing of signals received by the transducers is performed by the specialized control systems. The specialized control systems are available to only a select few. Such design further limits the versatility and accessibility of the ultrasound probes.

SUMMARY

Aspects of the present application provide a highly integrated, microfabricated ultrasound transducer probe which may serve as a stand-alone ultrasound transducer probe and which is configured to be interconnectable with other such transducer probes to form ultrasound devices capable of two-dimensional (2D) and three-dimensional (3D) ultrasound imaging. In some embodiments, the ultrasound transducer probe includes microfabricated ultrasonic transducers integrated with integrated circuitry controlling operation of the ultrasonic transducers and providing multiple electronic interfaces for connecting the ultrasound transducer probe to one or more external devices. In some embodiments, the device is a complete ultrasound-on-a-chip containing all transducers and electronics to perform collection and processing of ultrasound signals. Final image processing may be performed on or off the chip.

The external devices may perform some processing and/or image generation with ultrasound data provided by the ultrasound transducer probe. In some embodiments, the ultrasonic transducers of the ultrasound transducer probe may be configured suitably to enable 2D imaging and the transducer probe itself may include a substrate with a suitable geometry to provide a 1D aperture or 1.5D aperture in some embodiments. A 1.5D aperture, and thus a 1.5D device (e.g., a 1.5D ultrasound transducer probe) is one in which focusing is provided along one dimension of the aperture. The integrated circuitry may be at least partially programmable to allow for coordinated operation between multiple such interconnected ultrasound transducer probes, for example when providing higher dimensional imaging functionality than that provided by a single instance of the ultrasound transducer probe.

The ultrasound transducer probes may be operated as sensors and/or sources of ultrasound energy. For example, the ultrasound transducer probes may be operated as ultrasound imaging probes in some embodiments, sensing ultrasound energy from a subject. The ultrasound energy may be emitted by the same ultrasound transducer probe detecting the ultrasound energy, or may be emitted by a distinct source. In some embodiments, the ultrasound transducer probe may be operated as a source, for example a source of high intensity focused ultrasound (HIFU).

Further aspects of the present application provide ultrasound devices making use of the microfabricated ultrasound transducer probe described above, ultrasound imaging techniques utilized by such devices, and methods of fabricating, operating, and/or interconnecting the microfabricated ultrasound transducer probe.

According to an aspect of the application, an apparatus is provided comprising a substrate, a plurality of ultrasonic transducers on the substrate, and control circuitry on the substrate, coupled to the plurality of ultrasonic transducers and configured to control operation of the plurality of ultrasonic transducers. The apparatus further comprises a first interface, the first interface being of a first type, and a second interface, the second interface being of a second type. The first and second interfaces may be individually configured to transfer electronic signals between the control circuitry and an external device.

According to an aspect of the application, an apparatus is provided comprising a single substrate ultrasound-on-a-chip imaging device comprising multiple different interface types supporting different data transfer rates.

According to an aspect of the application, an apparatus is provided comprising a substrate including a plurality of ultrasound elements, a first interface of a first type on the substrate, and a second interface of a second type that is different than the first type on the substrate.

According to an aspect of the application, a method is provided, comprising forming a plurality of ultrasonic transducers on a substrate, forming control circuitry on the substrate, coupled to the plurality of ultrasonic transducers, and forming a first interface of a first type on the substrate and a second interface of a second type on the substrate. The first and second interfaces may be individually configured to provide an electrical connection between the control circuitry and an external device.

According to an aspect of the application, an apparatus is provided, comprising a substrate, a plurality of ultrasonic transducers on the substrate, and control circuitry on the substrate, coupled to the plurality of ultrasonic transducers and configured to control operation of the plurality of ultrasonic transducers. The control circuitry comprises a waveform generator coupled to at least one ultrasonic transducer of the plurality of ultrasonic transducers, the waveform generator being configurable to generate different kinds of waveforms.

According to an aspect of the application, an apparatus is provided, comprising a substrate having a width and height, the width being at least twice as large as the height, and a plurality of ultrasonic transducers on the substrate. The apparatus further comprises control circuitry on the substrate, coupled to the plurality of ultrasonic transducers and configured to control operation of the plurality of ultrasonic transducers.

According to an aspect of the application, an apparatus is provided, comprising a plurality of ultrasound transducer probes tiled and interconnected to form an ultrasound imaging device. Each ultrasound transducer probe of the plurality of ultrasound transducer probes includes a plurality of ultrasonic transducers and control circuitry coupled to the plurality of ultrasonic transducers and configured to control, at least in part, operation of the plurality of ultrasonic transducers. The control circuitry includes interface circuitry configured to interface the ultrasound transducer probe to an external device.

According to an aspect of the application, an apparatus is provided, comprising at least one substrate having a first dimension and a second dimension that is perpendicular to the first dimension. The first dimension is at least twice as great as the second dimension. The apparatus further comprises a plurality of ultrasonic transducers on the substrate, the plurality of ultrasonic transducers being arranged along the first dimension and the second dimension of the substrate. The apparatus further comprises control circuitry coupled to the plurality of ultrasonic transducers and configured to control operation of the plurality of ultrasonic transducers.

According to an aspect of the application, a method of forming an ultrasound device is provided, comprising dicing at least first and second ultrasound transducer probes of a plurality of ultrasound transducer probes on a wafer, and tiling and interconnecting the at least first and second ultrasound transducer probes.

According to an aspect of the application, a device is provided comprising a plurality of complementary metal oxide semiconductor (CMOS) ultrasound transducer elements, and CMOS control circuitry coupled to the plurality of CMOS ultrasound transducer elements and configured to control the CMOS ultrasound transducer elements to support one-dimensional (1D), two-dimensional (2D), and three-dimensional (3D) ultrasound imaging.

According to an aspect of the present application, a complementary metal oxide semiconductor (CMOS) integrated circuit (IC) is provided comprising an array of ultrasound transducer elements and CMOS control circuitry coupled to the array of ultrasound transducer elements and configured to control operation of the array of ultrasound transducer elements to support both two-dimensional (2D) and three-dimensional (3D) ultrasound imaging.

According to an aspect of the application, an apparatus is provided, comprising a complementary metal oxide semiconductor (CMOS) substrate and a plurality of ultrasonic transducers on the CMOS substrate. The apparatus further comprises a CMOS integrated circuit (IC) on the CMOS substrate and coupled to the plurality of ultrasonic transducers, wherein the CMOS IC is configured to support a voltage signal that is greater than approximately 20 V.

According to an aspect of the application, an apparatus is provided, comprising a complementary metal oxide semiconductor (CMOS) substrate having a top metal layer configured to conduct a power signal. The apparatus further comprises an ultrasonic transducer disposed above the top metal layer and including an electrode, wherein the electrode is connected to the top metal layer by an electrically conductive via.

According to an aspect of the application an apparatus is provided comprising a complementary metal oxide semiconductor (CMOS) substrate having a top metal layer. The top metal layer has a thickness between approximately 0.5 microns and approximately 10 microns. The apparatus further comprises an ultrasonic transducer disposed above the top metal layer.

According to an aspect of the application, an apparatus is provided comprising a complementary metal oxide semiconductor (CMOS) substrate having a metal layer having a thickness between approximately 0.5 microns and approximately 10 microns. The apparatus further comprises an ultrasonic transducer having an electrode. The apparatus further comprises a via connecting the electrode to the metal layer of the CMOS substrate.

According to an aspect of the application, an apparatus is provided comprising a complementary metal oxide semiconductor (CMOS) substrate comprising a metallization layer and a wiring line. The apparatus further comprises an ultrasonic transducer on the CMOS substrate. The metallization layer is configured to distribute a power signal and is configured as an electrical shield between the ultrasonic transducer and the wiring line.

According to an aspect of the application, an apparatus is provided, comprising a complementary metal oxide semiconductor (CMOS) substrate and an ultrasonic transducer on the CMOS substrate. The ultrasonic transducer comprises a membrane sealing a cavity in the CMOS substrate and further comprises a thin film electrode. The cavity is between the thin film electrode and the membrane.

According to an aspect of the application, a method of fabricating an ultrasonic transducer is provided, comprising forming the ultrasonic transducer above a top metal layer of a complementary metal oxide semiconductor (CMOS) substrate, and connecting the ultrasonic transducer to the top metal layer with at least one electrically conductive via.

According to an aspect of the application a method of manufacturing an ultrasonic transducer is provided, comprising forming a complementary metal oxide semiconductor (CMOS) substrate, the CMOS substrate including a metal layer, and forming an electrically conductive via through a portion of the CMOS substrate. The method further comprises forming the ultrasonic transducer above the CMOS substrate, wherein at least a portion of the ultrasonic transducer is electrically coupled to the CMOS substrate through the electrically conductive via.

According to an aspect of the application, a method is provided, comprising printing a photolithography pattern on a wafer, rotating the wafer by approximately 180 degrees after printing the photolithography pattern on the wafer, and printing a copy of the photolithography pattern on the wafer after rotating the wafer by approximately 180 degrees such that the pattern on the wafer and the copy of the pattern on the wafer are aligned with each other.

According to an aspect of the application, a method is provided comprising printing a photolithography pattern on a wafer, rotating the wafer after printing the photolithography pattern on the wafer, and printing a copy of the photolithography pattern on the wafer after rotating the wafer such that the pattern on the wafer and the copy of the pattern on the wafer are aligned with each other.

According to an aspect of the application, a method is provided, comprising illuminating a reticle having a pattern thereon to print a pattern on a wafer, the pattern on the reticle having a first side substantially opposite a second side, and the pattern on the wafer having a first side substantially opposite a second side. The method further comprises rotating the wafer approximately 180 degrees, and aligning the second side of the pattern on the reticle with the second side of the pattern on the wafer. The method further comprises, subsequent to aligning the second side of the pattern on the reticle with the second side of the pattern on the wafer, illuminating the reticle.

According to an aspect of the application, a method is provided, comprising scanning a first portion of a reticle with a photolithographic scanner to print a first pattern on a wafer, the first portion being less than the entire reticle. The method further comprises stepping the wafer. The method further comprises, subsequent to stepping the wafer, scanning a second portion of the reticle with the photolithographic scanner to print a second pattern on the wafer in alignment with the first pattern, the second portion being less than the entire reticle and being different than the first portion.

According to an aspect of the application, a method is provided comprising tiling ultrasound transducer probes on a wafer by printing different patterns from one or more reticles on the wafer. Printing different patterns may comprise using a blade to obstruct at least a portion of at least one reticle during tiling.

According to an aspect of the application, a method is provided comprising scanning a first portion of a pattern mask with a scanner to print a first pattern on a wafer, the pattern mask including a first, second, third, and fourth alignment mark thereon. The first portion includes an area between the first alignment mark and the third alignment mark. The method further comprises moving the wafer, and scanning a second portion of the pattern mask with the scanner to print a second pattern on the wafer in alignment with the first pattern. The second portion includes an area between the second alignment mark and the fourth alignment mark.

BRIEF DESCRIPTION OF THE DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

FIGS. 1A-1D illustrate differing ultrasound transducer devices which may be formed from a common repeatable ultrasound transducer probe, according to non-limiting embodiments of the present application.

FIGS. 30A-30G illustrate a device including an ultrasonic transducer integrated with a CMOS substrate and formed above a top metal layer of the CMOS substrate, and a method of fabricating the device, according to a non-limiting embodiment of the present application.

DETAILED DESCRIPTION

Overview

Figure 2A:
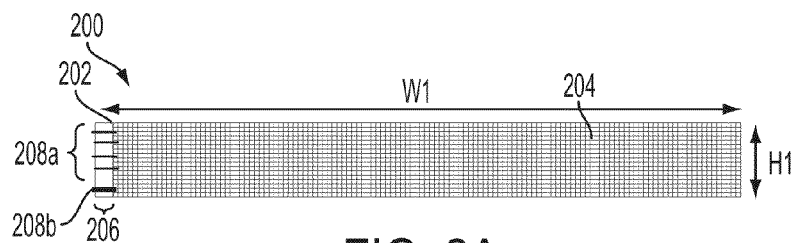
FIGS. 2A and 2B illustrate non-limiting alternative embodiments of an ultrasound transducer probe which may be configured to be interconnectable with other such ultrasound transducer probes, according to non-limiting embodiments of the present application.

Aspects of the present application provide a microfabricated ultrasound transducer probe which may represent a universal building block to construct various types of ultrasound imaging and/or HIFU devices operable in various modes by mere replication and suitable connection of multiple copies of the transducer probe. In some embodiments, the ultrasound transducer probe is suitable to operate as a standalone ultrasound transducer probe. One-dimensional (1D), one and a half dimensional (1.5D), two-dimensional (2D), and three-dimensional (3D) ultrasound imaging devices capable of implementing highly advanced ultrasound imaging techniques may be fabricated easily by replication of, suitable dicing of, and interconnection of the ultrasound transducer probe, with minimal or no redesign of the ultrasonic transducers and integrated circuitry of the ultrasound transducer probe. As a result, the ultrasound transducer probe is highly versatile, providing flexibility in achieving an ultrasound device of choice.

Various features of the microfabricated ultrasound transducer probe may contribute to its versatility and provide flexibility to an end user. One such feature is the inclusion of multiple types of interfaces for electrically connecting to different types of external devices. In some embodiments, higher speed and lower speed interfaces may be provided as part of the ultrasound transducer probe for communicating electrical signals with external devices at different rates. The higher speed interface(s) may facilitate connection of the ultrasound transducer probe to any desired external processing device, such as specialized field programmable gate arrays (FPGA), graphics processing units (GPU), or other devices suitable for receiving and processing ultrasound data, for example to form one or more ultrasound images. The higher speed interface(s) may be configured in some embodiments to maximize the output of ultrasound data, which may be in digital form, from the ultrasound transducer probe. In some embodiments, then, the higher speed interface(s) may be used when complex ultrasound applications are to be performed, such as 3D ultrasound imaging. The lower speed interface(s), by contrast, may be configured in some embodiments to allow for connection of the ultrasound transducer probe to a consumer electronics device with lesser processing capabilities than some types of devices to which the higher speed interface(s) may be connected, and thus may be suitable when performing ultrasound applications not requiring the amount of data provided by the higher speed interface(s). Such functionality may make the ultrasound transducer probe usable by a wide range of end users who lack access to more sophisticated graphics processing systems, thereby making an important medical diagnostic tool accessible to a large number of people. Thus, the interface configuration of the ultrasound transducer probe may enhance the transducer probe's versatility by allowing for connection to a wide range of external devices, and may provide a user flexibility in choosing to which external device(s) to connect.

Other features of an ultrasound transducer probe which may be provided according to some aspects of the present application and which may contribute to the transducer probe's versatility include the transducer probe's physical form and the architecture of the transducer probe circuitry. The ultrasound transducer probe may be microfabricated on a substrate (e.g., a chip, such as a semiconductor chip) having a geometry that provides for a suitable aperture. In some embodiments, for example, the substrate may allow for a suitable one-dimensional (1D) aperture, for instance being wider than it is tall (e.g., a wide aspect ratio substrate). Such a form factor may allow the transducer probe to function suitably as a 1D imaging device for performing 2D imaging while allowing for multiple replicas of the transducer probe to be tiled horizontally and/or vertically to provide enhanced 2D or 3D imaging functionality. As used herein, "tiled" means arranged next to each other to form, in combination, a larger device. In some embodiments, the ultrasound transducer probe may be a 1.5D device capable of tiling to provide enhanced 2D or 3D imaging functionality.

Interconnection of multiple tiled replicas of the ultrasound transducer probe in a manner suitable to form a larger ultrasound transducer probe may be facilitated by suitable relative physical positioning of the ultrasonic transducers and integrated processing or control circuitry on the substrate. As used herein, the term "control circuitry" may include, but is not limited to, circuitry that may control operation of the ultrasonic transducers and/or processing circuitry that processes signals transmitted to and/or received from the ultrasonic transducers. In some embodiments, a portion of the control circuitry may be positioned beneath an arrangement of ultrasonic transducers on the substrate, with other integrated circuitry including input/output (I/O) circuitry positioned on one or more peripheral regions (e.g., a tab in some embodiments) of the substrate. Such physical placement may facilitate tiling multiple copies of the ultrasound transducer probe by allowing for creation of a substantially continuous arrangement of ultrasonic transducers when tiled while providing suitable external access to the circuitry of the transducer probes, i.e., not obstructing the I/O circuitry when the transducer probes are tiled.

The integrated circuitry (e.g., integrated control circuitry) of the ultrasound transducer probe may also facilitate interconnection of the transducer probe with other such transducer probes, for example when tiled as described above. In some embodiments, the integrated circuitry may be at least partially programmable, thus allowing for the ultrasound transducer probe to be programmed to operate as a standalone transducer probe or in conjunction with one or more additional such transducer probes. The programmable circuitry may include programmable timing circuitry and/or a programmable waveform generator for generating (or producing) excitation signals to excite the ultrasonic transducers. The waveform generator may be programmable to generate a desired kind of waveform from among multiple possible kinds, including impulses, continuous waves, chirp waveforms (e.g., linear frequency modulation (LFM)) chirps), and coded excitations. Such flexibility in the waveform generated may also facilitate the use of highly advanced ultrasound imaging techniques, non-limiting examples of which are described further below.

The ultrasound transducer probe may include micromachined ultrasonic transducers having features which facilitate creation of a standalone ultrasound transducer probe, and which also facilitate formation of ultrasound devices by interconnection of multiple copies of the ultrasound transducer probe. In some embodiments, the ultrasound transducer probe may be formed on a complementary metal oxide semiconductor (CMOS) substrate. In some embodiments, the CMOS substrate may include a top metal layer, which in some embodiments may be a thick top metal layer (also referred to in some embodiments as an ultra-thick redistribution layer), which may be utilized for power distribution to the ultrasonic transducers. Such a configuration may facilitate suitable power distribution to all ultrasonic transducers of the transducer probe over the relatively large distances which the power signal may travel in some embodiments. When the thick top metal layer is used for power distribution, the ultrasonic transducers may be formed above the thick top metal layer, and may be connected to the thick top metal layer with a suitable electrically conductive via structure including one or more electrically conductive vias. In some such embodiments, one electrically conductive via may connect a bottom electrode of an ultrasonic transducer to the thick top metal layer of the CMOS substrate, and a second electrically conductive via may connect a membrane of the ultrasonic transducer to the thick top metal layer. Further details of such structures are described further below, along with methods of fabricating such structures.

Some aspects of the present application provide wafer-level fabrication techniques for fabricating ultrasound transducer probes of the types described herein. For example, interconnection of multiple copies of an ultrasound transducer probe may be achieved in multiple ways according to different embodiments by suitable positioning of the ultrasound transducer probes on a wafer and suitable dicing. In some embodiments, multiple copies of the ultrasound transducer probes may be suitably tiled and interconnected on a wafer and then diced together to form a single-substrate ultrasound device, for instance to meet certain performance specifications for the device. In other embodiments, individual copies of the ultrasound transducer probe or groups of multiple instances of the ultrasound transducer probe may be diced from a wafer and interconnected after dicing. According to aspects of the present application, scanning and/or stepping technologies may be used to suitably position multiple instances of an ultrasound transducer probe on a wafer.

In some embodiments, multiple instances of an ultrasound transducer probe may be aligned on a wafer by printing a pattern from a reticle on the wafer, rotating the wafer, and printing the pattern again. In some embodiments, an ultrasound transducer probe may be formed by printing portions of a pattern from a reticle on the wafer in alignment with each other. Blading techniques may be used to print desired portions of the reticle pattern, and stepping and/or scanning may be used to provide proper alignment of the various portions printed.

As described previously, some embodiments of the present application provide an ultrasound transducer probe which may serve as a building block (also referred to in some embodiments as a "repeatable unit" or simply a "unit," a "module," or by other similar terminology) for constructing ultrasound imaging devices with desired imaging capabilities. In some such embodiments, the ultrasound transducer probe may be a 1D ultrasound transducer probe, but not all embodiments are limited in this respect. For instance, the building block ultrasound transducer probe may be a 1.5D or 2D transducer probe in some embodiments.

The aspects and embodiments described above, as well as additional aspects and embodiments, are described further below. These aspects and/or embodiments may be used individually, all together, or in any combination of two or more, as the application is not limited in this respect.

Standalone and Tiled Ultrasound Transducer Probes

According to an aspect of the present application, different types of ultrasound devices with different ultrasound imaging and/or HIFU capabilities may be created utilizing a common, repeatable ultrasound transducer probe, which in some embodiments may be a 1D ultrasound transducer probe or a 1.5D ultrasound transducer probe. FIGS. 1A-1D illustrate examples of ultrasound devices that may be created in this manner.

FIG. 1A illustrates an ultrasound device 100 positioned to perform ultrasound analysis of a subject 102. The ultrasound device 100 may represent a single repeatable ultrasound transducer probe. That is, the ultrasound device 100 may be referred to alternatively as an ultrasound transducer probe. The ultrasound device 100 is connected to an external device 104, illustrated as a smartphone (or mobile phone) in this non-limiting example, via a wired connection 106.

The ultrasound device 100 may be a 1D ultrasound transducer probe, configured with a 1D aperture formed by a plurality of ultrasonic transducers which may be microfabricated on a substrate (e.g., a semiconductor substrate in some embodiments). The ultrasound device 100 may further include control circuitry configured to control, at least in part, the ultrasonic transducers. Non-limiting examples of suitable 1D ultrasound transducer probes which may serve as the ultrasound device 100 are described in further detail below, for example in connection with FIGS. 2A and 2B.

The ultrasound device 100 may have any suitable dimensions, including a width W1 and height H1. In some embodiments, the ultrasound device 100 may be a 1D ultrasound transducer probe configured with a 1D aperture, and thus the width W1 may be greater than the height H1 in some such embodiments. In some embodiments, the width W1 may be between approximately 20 mm and approximately 40 mm, or any value within that range. In some embodiments, the height H1 may be between approximately 2 mm and approximately 10 mm, or any value within that range. In some embodiments, a square ultrasound device 100 may be provided having a width W1 equal to the height H1.

The external device 104 may be a device configured to receive and process ultrasound data provided by the ultrasound device 100. In some embodiments, the external device 104 may be a consumer electronics device (e.g., the illustrated smartphone) having a display 108 for displaying ultrasound data and/or ultrasound images based on ultrasound data produced by the ultrasound device 100. However, other types of external devices may be utilized as the various aspects described herein are not limited to the particular type of external device to which the ultrasound transducer probe is connected.

FIG. 1B illustrates a variation on FIG. 1A in which an ultrasound device 110 is provided. The ultrasound device 110 may represent a composite ultrasound transducer probe including multiple repeatable ultrasound transducer probes, for example of the type illustrated in FIG. 1A. The ultrasound device 110 may be a 1D ultrasound transducer probe formed by suitable horizontal tiling and interconnection of two of the ultrasound devices 100 of FIG. 1A in a side-by-side (or left-to-right) configuration. Thus, the ultrasound device 110 may have the same height H1 as the ultrasound device 100, but may have a width W2 that is approximately or substantially twice as great as the width W1. In this manner, the ultrasound device 110 may provide a greater linear aperture than the ultrasound device 100 and may be used to image a greater area.

The ultrasound device 110 may be connected to an external device 112 via the wired connection 106. In the example shown, the external device 112 is a tablet computer having a display 114 for displaying ultrasound data and/or ultrasound images based on ultrasound data produced by the ultrasound device 110. However, other types of external devices may be used.

FIG. 1C illustrates a further example of an ultrasound device which may be formed from a collection of multiple ultrasound transducer probes, for example of the type of ultrasound device 100 of FIG. 1A. That is, like the ultrasound device 110, the ultrasound device 116 may represent a composite ultrasound transducer probe including multiple repeatable ultrasound transducer probes, for example of the type illustrated in FIG. 1A.

The ultrasound device 116 may be a 2D ultrasound transducer probe formed by suitable vertical tiling (also referred to herein as "stacking") and interconnection of multiple copies of the ultrasound device 100. Thus, the ultrasound device 116 may have the same width W1 as ultrasound device 100 and a height H2 greater than the height H1 of ultrasound device 100. The height H2 may be, for example, N×H1, wherein N represents the number of ultrasound devices 100 tiled vertically to create the ultrasound device 116. In some embodiments, N may equal 2, 4, 8, may be between 2 and 10, or may assume any other suitable integer value.

The ultrasound device 116 may be connected to an external device 118 by the wired connection 106. The external device 118 may be any suitable external device, including any suitable consumer electronics device. In the non-limiting example illustrated, the external device 118 is a laptop computer having a display 120 for displaying ultrasound data and/or ultrasound images based on ultrasound data produced by the ultrasound device 116.

Although not shown, it should be appreciated that an ultrasound device may be constructed from horizontal and vertical tiling of multiple copies of the ultrasound device 100, thus effectively representing a combination of ultrasound device 110 and ultrasound device 116. For example, two of the ultrasound devices 100 may be tiled horizontally, defining a "row" that is two ultrasound transducer probes wide, and two or more such rows of two ultrasound transducer probes may be tiled vertically (e.g., 2 such rows, 4 such rows, 8 such rows, or any other suitable number of such rows). Thus, an ultrasound transducer probe having a desired size and aperture may be easily created by suitable tiling of an ultrasound transducer probe like ultrasound device 100. The ultrasound device 100 may therefore serve as a (universal) building block for building an ultrasound device with target size and aperture characteristics, and therefore specified imaging and/or HIFU capabilities.

A further example of an ultrasound device which may be formed utilizing multiple copies of the ultrasound device 100 of FIG. 1A is shown in FIG. 1D. As shown, the ultrasound device may include two copies of the ultrasound device 116 of FIG. 1C, each of which may include two or more instances of the ultrasound device 100, as previously described. The two ultrasound devices 116 in FIG. 1D may be configured to operate in combination to perform transmissive ultrasound imaging, for example being positioned on opposite sides of the subject 102. For example, the ultrasound devices 116 may operate together in the configuration of FIG. 1D according to the transmissive ultrasound operating techniques described in PCT Patent Application Publication No. WO 2013/059,358 A2, which is hereby incorporated herein by reference in its entirety. The configuration of FIG. 1D may be particularly advantageous for 3D ultrasound imaging purposes, though it need not be used in this manner.

The ultrasound devices 116 in FIG. 1D may be connected to an external device 122 via respective wired connections 124. The external device 122 may be any suitable external device for receiving and processing the ultrasound data provided by the ultrasound devices 116. In some embodiments, the external device 122 may include an FPGA, a GPU, or other suitable processing circuitry for receiving and handling large amounts of ultrasound data as may be produced in the configuration of FIG. 1D.

Also provided in FIG. 1D is a second external device 126 having a display 128 for displaying ultrasound data and/or ultrasound images based on ultrasound data produced by the ultrasound devices 116. The external device 126 may be connected to receive data from the external device 122 in some embodiments, though alternative configurations are possible. Furthermore, in some embodiments the external device 122 may itself include a suitable display, and external device 126 may be omitted.

Thus, FIGS. 1A-1D illustrate different ultrasound transducer probes and device configurations for producing ultrasound data and/or ultrasound images based upon a common underlying ultrasound device 100. Both reflective (e.g., FIGS. 1A-1C) and transmissive (e.g., FIG. 1D) ultrasound imaging devices may be created, operating in two or three dimensions.

The ultrasound devices illustrated in FIGS. 1A-1D and, more generally, described herein may be placed at various positions relative to a subject. In some embodiments, the ultrasound devices may be placed in contact with the subject. In some embodiments, the ultrasound devices may be placed in proximity to, but not in contact with, the subject, for example being within several centimeters of the subject. Thus, the ultrasound devices are not limited to being used at any particular distance from a subject unless otherwise stated. Moreover, the ultrasound devices may be moveable (or positionable), for example by hand. Thus, an operator (e.g., an ultrasound technician) may move the location of the ultrasound devices during operation, in some embodiments. The ultrasound devices may therefore be considered portable in some embodiments.

It should be appreciated that the ultrasound transducer probes shown in FIGS. 1A-1D may be considered ultrasound peripherals, configured to be connected to (e.g., plugged into) a suitable external device to provide some control and/or processing functionality. Thus, aspects of the present application provide desired ultrasound peripherals based on suitable replication and interconnection of a common, repeatable ultrasound transducer probe design.

FIGS. 1A-1D illustrate ultrasound transducer probes connected to external devices by wired connections (e.g., wired connections 106 and 124). However, wireless connections may alternatively be implemented in some embodiments.

FIGS. 2A-2G illustrate examples of configurations of ultrasound transducer probes which may be used to form the devices of FIGS. 1A-1D. FIG. 2A illustrates a first non-limiting example of an ultrasound transducer probe 200 representing an implementation of the ultrasound device 100. The ultrasound transducer probe 200 may be a 1D ultrasound transducer probe having a substrate 202 with the width W1 and height H1, on which a plurality of ultrasonic transducers 204 and integrated control circuitry (not explicitly shown) are formed. As shown, the plurality of ultrasonic transducers 204 may be positioned over a majority of the substrate 202, including over the center of the substrate 202. A peripheral region 206 of the substrate 202, which may represent a "tab" of the substrate 202, may include integrated circuitry including interface circuitry (e.g., interfaces 208a and 208b, described further below). The peripheral region 206 may not include any of the ultrasonic transducers 204.

Figure 2B:
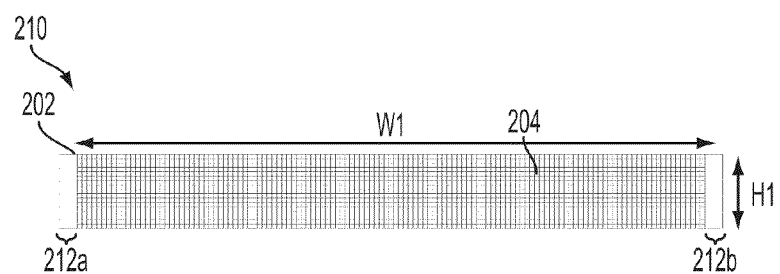

FIG. 2B illustrates a variation on the ultrasound transducer probe 200 of FIG. 2A. The ultrasound transducer probe 210 of FIG. 2B may differ from the ultrasound transducer probe 200 in that instead of a single peripheral region 206, the ultrasound transducer probe 210 may include two peripheral regions (or "tabs") 212a and 212b. The peripheral regions 212a and 212b may have a combined width, in the direction parallel to W1, equal to the width of peripheral region 206 in the direction parallel to W1, though not all embodiments are limited in this respect. For example, each of regions 212a and 212b may have a width in the direction parallel to W1 equal to approximately half the width of peripheral region 206 in the direction parallel to W1. One or both of the peripheral regions 212a and 212b may include integrated circuitry including interface circuitry (not shown). In some embodiments, only one of the two peripheral regions 212a and 212b may include I/O circuitry acting as an interface for an external device. Such a configuration may facilitate horizontal tiling of ultrasound transducer probes so that access to the integrated circuitry of the horizontally tiled ultrasound transducer probes need not be provided at a middle point between the horizontally tiled transducer probes.

As previously described, the width W1 and height H1 may assume any suitable values. In some embodiments, the aspect ratio of the substrate 202, defined as the width relative to the height, may be greater than or equal to 1.5:1, greater than or equal to 2:1, greater than or equal to 3:1, greater than or equal to 4:1, greater than or equal to 5:1, between 2:1 and 16:1, between 4:1 and 10:1, or any range or value within such ranges, as non-limiting examples. The substrate 202 may be said to be a wide aspect ratio substrate when the aspect ratio is greater than or equal to 3:1. In some embodiments, the width W1 may be between approximately 20 mm and approximately 40 mm, or any value within that range. In some embodiments, the height H1 may be between approximately 2 mm and approximately 10 mm, or any value within that range. As a non-limiting example, the width W1 may be approximately 32 mm and the height H1 may be approximately 4 mm. In FIG. 2A, the width of the peripheral region 206, parallel to W1, may be approximately 3 mm with the remaining part of the width of the ultrasound transducer probe 200 being covered by ultrasonic transducers. In the embodiment of FIG. 2B, each of the peripheral regions 212a and 212b may have a width (parallel to W1) of approximately 1.5 mm.

It should be appreciated that the ultrasound transducer probes 200 and 210 may be 1.5D ultrasound transducer probes in some embodiments. For example, a suitable number of ultrasonic transducers may be provided along the height H1 to allow for focusing of ultrasound energy in the height dimension.

Figure 2C:
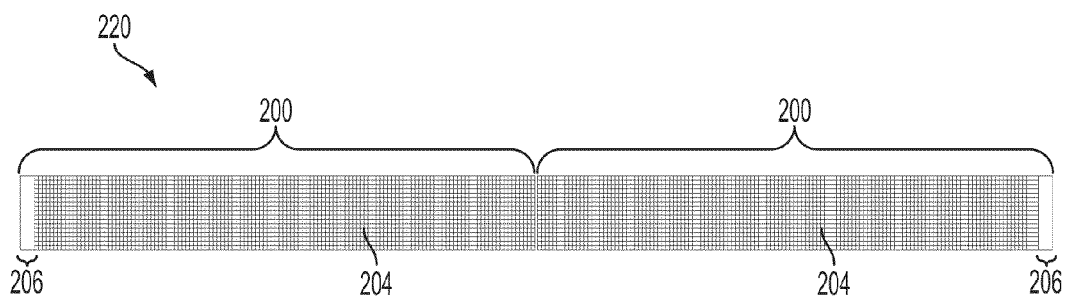
FIGS. 2C, 2F, and 2G illustrates ultrasound transducer probes which may be formed by tiling and interconnecting multiple instances of the ultrasound transducer probe of FIG. 2A, according to non-limiting embodiments of the present application.

FIG. 2C illustrates an ultrasound transducer probe 220 which may represent an implementation of ultrasound device 110 of FIG. 1B. As shown, the ultrasound transducer probe 220 may include two copies of the ultrasound transducer probe 200 horizontally tiled, with the peripheral regions 206 positioned to be on opposite sides of the ultrasound transducer probe 220. The configuration of FIG. 2C may be achieved by fabricating the two copies of ultrasound transducer probe 200 on a single wafer and dicing them together, or may be achieved by individually dicing the two copies of ultrasound transducer probe 200 and then positioning and interconnecting them. In some embodiments, one copy of the ultrasonic transducer probe may be a mirror image of the other copy (e.g., the copy on the left side of transducer probe 220 may be a mirror image of the copy on the right side of transducer probe 220). Thus, aspects of the present application provide for suitable tiling of multiple instances of an ultrasound transducer probe in a mirror image configuration to form a larger ultrasound transducer probe.

Figure 2D:
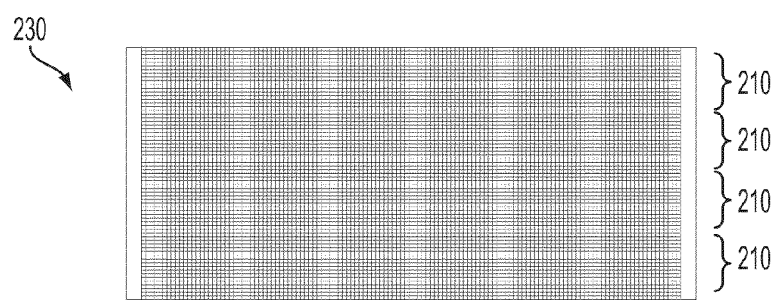
FIGS. 2D and 2E illustrate ultrasound transducer probes which may be formed by tiling and interconnecting multiple instances of the ultrasound transducer probe of FIG. 2B, according to non-limiting embodiments of the present application.

FIG. 2D illustrates an ultrasound transducer probe 230 which may represent an implementation of ultrasound device 116 of FIG. 1C. As shown, the ultrasound transducer probe 230 may include four copies of the ultrasound transducer probe 210 of FIG. 2B vertically tiled (also referred to herein as "stacked"). The configuration of FIG. 2D may be achieved by fabricating the four copies of ultrasound transducer probe 210 on a single wafer and dicing them together, or may be achieved by dicing one or more of the ultrasound transducer probes 210 individually and then positioning and interconnecting them.

Figure 2E:
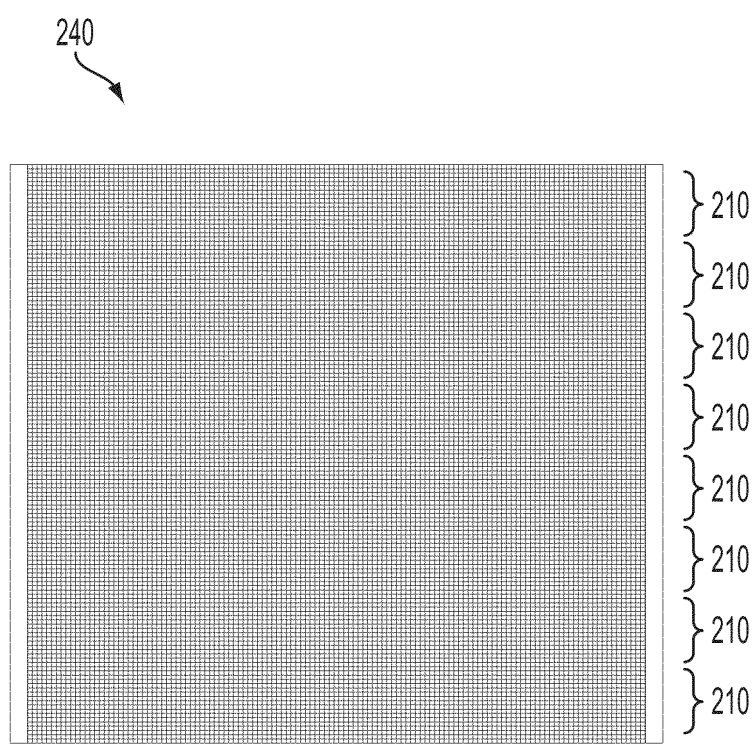

FIG. 2E illustrates an alternative ultrasound transducer probe 240 which may represent an alternative implementation of ultrasound device 116 of FIG. 1C. As shown, the ultrasound transducer probe 240 may include eight copies of the ultrasound transducer probe 210 of FIG. 2B vertically tiled. The configuration of FIG. 2E may be achieved by fabricating the eight copies of ultrasound transducer probe 210 on a single wafer and dicing them together, or may be achieved by dicing one or more of the ultrasound transducer probes 210 individually and then suitably positioning and interconnecting them.

Figure 2F:
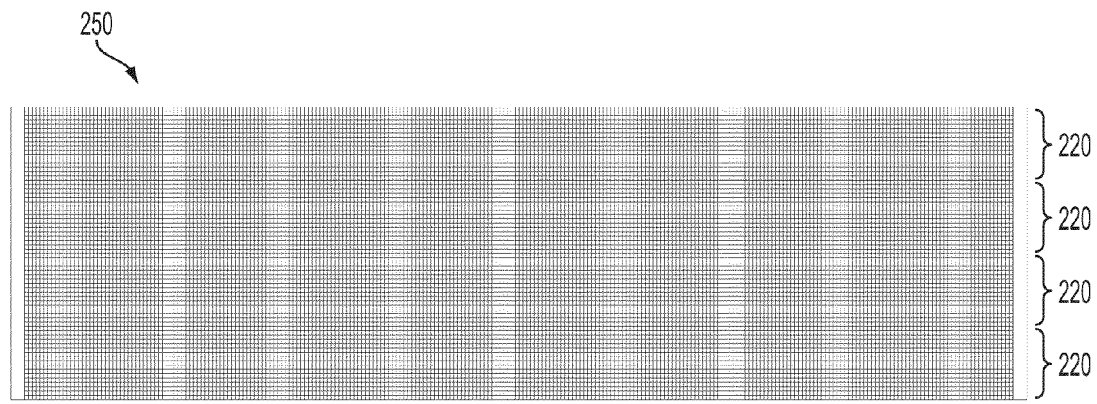

FIG. 2F illustrates an ultrasound transducer probe formed by suitable horizontal and vertical tiling and interconnection of multiple instances of the ultrasound transducer probe 200 of FIG. 2A. Namely, the ultrasound transducer probe 250 includes four vertically tiled (or stacked) instances of the ultrasound transducer probe 220 of FIG. 2C, and thus includes eight instances of the ultrasound transducer probe 200 of FIG. 2A. Four instances of the ultrasound transducer probe 200 may be positioned on the left half of the ultrasound transducer probe 250, with the other four instances of the ultrasound transducer probe 200 being positioned on the right half, as mirror images of the left half, of ultrasound transducer probe 250.

Figure 2G:
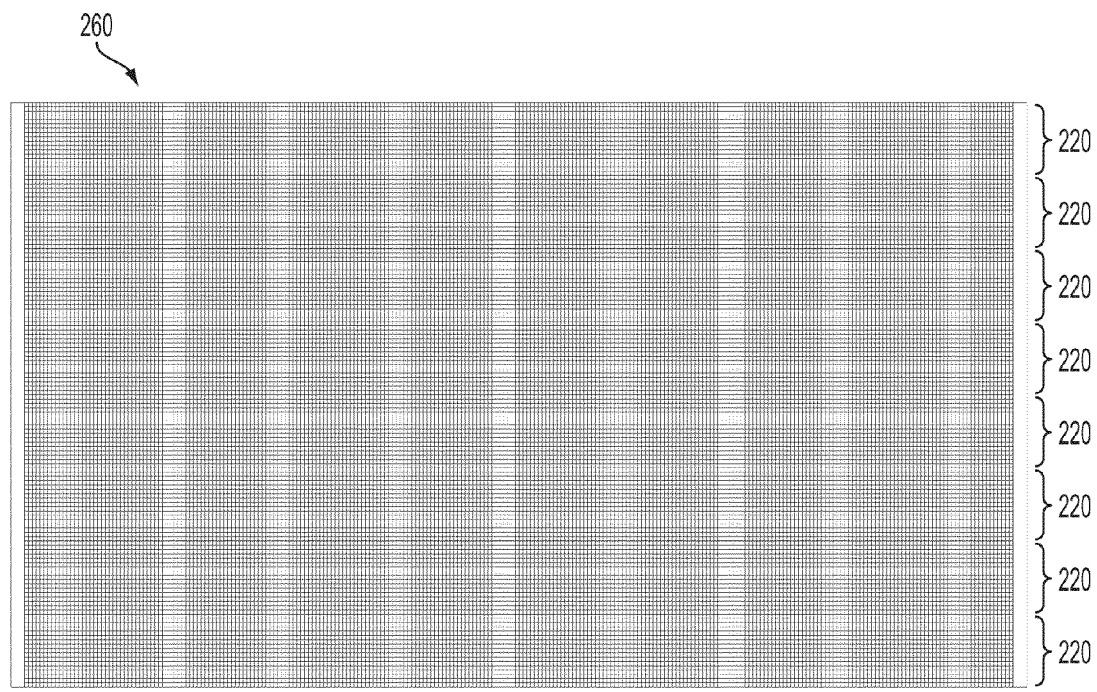

FIG. 2G illustrates a further example of an ultrasound transducer probe which may be formed by suitable horizontal and vertical tiling and interconnection of multiple instances of the ultrasound transducer probe 200 of FIG. 2A. The ultrasound transducer probe 260 includes eight vertically tiled (or stacked) instances of the ultrasound transducer probe 220 of FIG. 2C, and thus includes sixteen instances of the ultrasound transducer probe 200.

It should be appreciated from FIGS. 2A-2G that suitable horizontal and/or vertical tiling of copies of an ultrasound transducer probe configured as a repeatable building block ultrasound transducer probe may be used to produce ultrasound transducer probes of various dimensions. In this manner, the use of a common, repeatable ultrasound transducer probe design may simplify design and manufacture of multiple different ultrasound transducer probe configurations.

It should be appreciated that alternative configurations of a repeatable ultrasound transducer probe to those shown in FIGS. 2A and 2B are possible, still allowing for constructions of tiled devices like those illustrated in FIGS. 2C-2G. For example, an ultrasound transducer probe may include peripheral regions on the top and bottom sides of the substrate in addition to or as an alternative to the peripheral regions 206, 212a and 212b. For example, peripheral regions free of ultrasonic transducers may be provided parallel to the length W1. Such peripheral regions may include only contact pads for making electrical connection to the ultrasonic transducers in some embodiments, although in alternative embodiments circuitry may also be included. In some embodiments, an ultrasound transducer probe may include one or more peripheral regions parallel to the width W1 and one or more peripheral regions parallel to the height H1. Such transducer probes may still be tiled to form a contiguous region of ultrasonic transducers using blading techniques of the type described further below, as an example.

Figure 3:
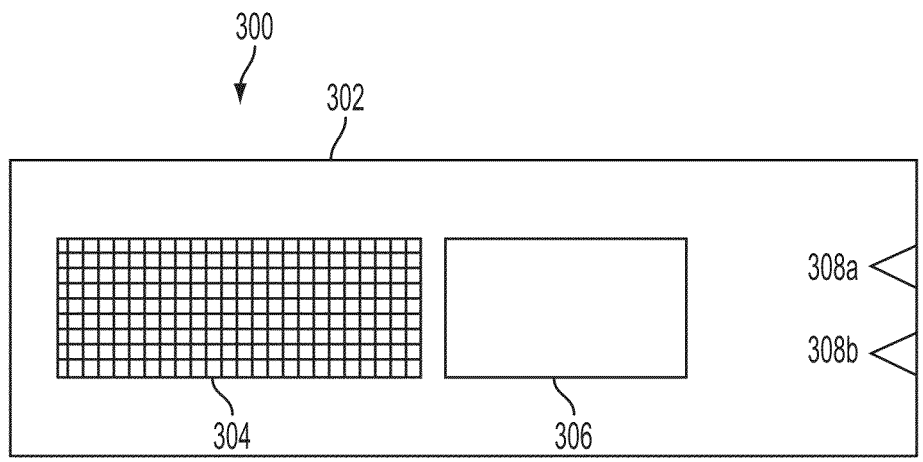
FIG. 3 is a block diagram of an ultrasound transducer probe which may be configured to be tiled and interconnected with other such ultrasound transducer probes, according to a non-limiting embodiment of the present application.

FIG. 3 is a block diagram representation of an ultrasound transducer probe which may serve as a stand-alone ultrasound transducer probe (e.g., a stand-alone 1D or 1.5D ultrasound transducer probe) and which may be repeatable so that it may be tiled and interconnected with other such transducer probes to form larger ultrasound devices. Thus, the ultrasound transducer probe 300 is a block diagram of a non-limiting example of the ultrasound device 100 of FIG. 1A and ultrasound transducer probes 200 and 210 of FIGS. 2A and 2B, respectively.

As shown, the ultrasound transducer probe 300 may include a substrate 302 on which may be a plurality of ultrasonic transducers 304 and integrated circuitry 306, which may perform control and/or processing functions. Interfaces 308a and 308b may provide electrical communication between the ultrasound transducer probe 300 and an external device (e.g., any of the external devices illustrated in FIGS. 1A-1D).

The ultrasonic transducers 304 may be capacitive micromachined ultrasonic transducers (CMUTs), CMOS ultrasonic transducers (CUTs), which are monolithically integrated ultrasonic transducers and CMOS ICs, or other ultrasonic transducers compatible with a CMOS substrate. In some embodiments, the ultrasonic transducers 304 may be formed on the substrate 302 using microfabrication techniques, and in some embodiments may be monolithically integrated with the substrate 302. For example, the substrate 302 may be a CMOS substrate and the ultrasonic transducers 304 may be monolithically integrated with the CMOS substrate.

The plurality of ultrasonic transducers 304 may be arranged to form a 1D (or 1.5D) aperture on the substrate 302, and the integrated circuitry 306 may operate the plurality of ultrasonic transducers in a 2D mode. The integrated circuitry may, in such an example, include transmit and receive circuitry. The ultrasound transducer probe 300 may be considered an ultrasound system-on-a-chip in some embodiments.

Various features of the ultrasound transducer probe 300, as well as ultrasound transducer probes 200 and 210 are now described in further detail.

Interface

Aspects of the present application provide an ultrasound transducer probe having multiple types of interfaces for electrically connecting the transducer probe to external devices via corresponding wired or wireless links. For example, higher speed and lower speed interfaces may be provided to allow an end user flexibility in choosing a type of device to which to connect the ultrasound transducer probe. FIG. 3 provides a non-limiting example.

The interfaces 308a and 308b may represent physical interfaces and may be considered part of the integrated circuitry 306. They may provide for electrical communication between the ultrasound transducer probe 300 and an external device. In some embodiments, the interfaces 308a and 308b may be of different types, configured to connect to different types of external devices. For example, the interface 308a may be of a type configured to connect to external devices capable of receiving and processing large amounts of ultrasound data, such as a specialized FPGA, a GPU, or other suitable device. By contrast, the interface 308b may be configured to operate with more widely available communication protocols used for consumer electronics devices, such as universal serial bus (USB) connections. Accordingly, the ultrasound transducer probe 300 may be highly versatile, allowing for the highest possible performance via connection to an external device with interface 308a or allowing for use with widely accessible consumer electronics via interface 308b, thus expanding the accessibility of ultrasound technology compared to current devices. The end user may choose between which interface to use in some embodiments.

When the interfaces 308a and 308b represent different types of physical interfaces, they may differ in the communication protocols supported and/or the speed of data communication supported (i.e., the data rate supported). For example, interface 308a may be a higher speed interface while interface 308b may be a lower speed interface. Thus, the interface 308a may be configured to maximize the amount of data which the ultrasound transducer probe 300 may provide to an external device, and thus may be used in situations in which advanced ultrasound imaging techniques are desirably implemented, high resolution is desired, fast frame rates are desired, or other imaging characteristics facilitated by high speed communication are desired. In some embodiments, a high speed interface may support data rates above approximately 4 gigabits per second (Gbps), above approximately 5 Gbps, above approximately 9 Gbps, above approximately 10 Gbps, above approximately 12 Gbps, above approximately 15 Gbps, above 30 Gbps, between approximately 9 Gbps and approximately 100 Gbps, between 15 Gbps and 50 Gbps, any data rate within those ranges, or any other suitable data rate. These data rates may represent maximum data rates in some embodiments.

By comparison, the interface 308b may be a relatively low speed interface suitable for supporting communication with consumer electronics (e.g., a portable device) or other external devices which may not be capable of performing the same level of ultrasound data processing as that provided by external devices connectable to the interface 308a, but which may be more widely available. When the interface 308b represents a relatively low speed interface, it may support less sophisticated ultrasound imaging techniques, may provide lower resolution ultrasound data, may provide lower frame rates, or otherwise provide a decrease in performance compared to that provided by interface 308a. In some embodiments, the interface 308b may be configured to support data rates less than approximately 10 Gbps, less than approximate 5 Gbps, less than approximately 4 Gbps, less than approximately 3 Gbps, less than approximately 2 Gbps, any data rate within those ranges, or any other suitable data rate. These data rates may represent maximum data rates in some embodiments.

Non-limiting examples of high speed interfaces, for example which may serve as interface 308a, include twisted pair interfaces, low voltage differential signaling (LVDS) interfaces, and optical fiber interfaces. Such high speed interfaces may implement high speed protocols such as SerDES, SONET, 10 GB Ethernet, 40 GB Ethernet, 100 GB Ethernet, PCI Express, HDMI, Infiniband, Thunderbolt, and JESD-204B, among others. External devices to which such an interface may connect may include high throughput devices, such as high throughput FPGAs.

In some embodiments, a high speed interface of an ultrasound transducer probe may connect to an FPGA which may perform some type of processing, such as packetization, compression, or other processing, before sending such data to a digital signal processor (DSP), central processing unit (CPU), or GPU. In some embodiments, the suitability of an external device for connection to a high speed interface of an ultrasound transducer probe (e.g., interface 308a) may be quantified by considering minimum memory and processing capacity targets. For example, a suitable external device may include over approximately 2 GB of random access memory (RAM) and/or over a particular number of processing cores, for example greater than 300 processing cores, greater than 400 processing cores, greater than 500 processing cores, between 200 and 600 processing cores, any number within that range, or any other suitable number. As non-limiting examples, the NVIDIA GTX 680 and NVIDIA Tesla K20, available from NVIDIA of Santa Clara, Calif., may be implemented in some embodiments as suitable external devices to which to connect a high speed interface of an ultrasound transducer probe of the types described herein.

Non-limiting examples of lower speed interfaces, for example which may be used for interface 308b, include USB 3.0, USB 2.0, firewire, and Gigabit Ethernet. The lower speed interfaces may be capable of connection to an external device via only a single cable in some embodiments (e.g., a USB cable).

In those aspects of the present application in which an ultrasound transducer probe includes different types of physical interfaces for interfacing with external devices, more than two different types of interfaces may be provided and/or more than two instances of one or more types of interfaces may be provided with an ultrasound transducer probe. For example, referring to FIG. 3, more than two interfaces may be provided with the ultrasound transducer probe 300. Considering FIG. 2A, for instance, four higher speed interfaces 208a may be provided while only a single lower speed interface 208b may be provided. The 4:1 ratio illustrated is non-limiting, however. For example, the ratio of higher speed interfaces to lower speed interfaces of an ultrasound transducer probe may be 2:1, 4:1, 8:1, 10:1, 1:1, 1:2, 1:4, any suitable ratio between those listed (e.g., between 10:1 and 1:4), or any other suitable ratio. More than one instance of the lower speed interface may also be provided in some embodiments.

As previously described, the higher speed interfaces may be configured to maximize the amount of ultrasound data provided by the ultrasound transducer probe to an external device. The number of higher speed interfaces may be selected accordingly in some embodiments. The number of higher speed interfaces may be selected based on the number of receive signal channels of the ultrasound transducer probe, which will be described further below in connection with an example of the architecture of the ultrasound transducer probe. For example, the more receive channels included with the ultrasound transducer probe, the greater the number of higher speed interfaces which may be included. In some embodiments, the number of higher speed interfaces provided may scale linearly and proportionally with the number of receive channels of the ultrasound transducer probe.

When multiple interfaces of a single type are included on a transducer probe of the types described herein, not all such interfaces need be used in all embodiments. The point may be illustrated by consideration of the ultrasound transducer probe 200 of FIG. 2A with the four illustrated interfaces 208a. In some embodiments, all four such interfaces may be utilized, for example when it is desired to maximize data output from the ultrasound transducer probe. However, in some embodiments, a reduced number of the four illustrated interfaces 208a may be used. For instance, only one, two, or three of the four interfaces 208a may be used in some embodiments, even though the transducer probe 200 may include all four. In some such embodiments, the number of interfaces used in operation may be dependent on a cable connected to the interfaces, non-limiting examples of which are described below in connection with FIGS. 4A and 4B. For example, plugging the transducer probe 200 into an external device using a particular type of cable may dictate how many of the four interfaces 208a are used. In an alternative embodiment, the number of available interfaces of a given type which are used in operation of the transducer probe may be programmable and thus a user may select the number via a selection tool (e.g., a menu option on a control program).

Although not explicitly shown, the interfaces of ultrasound transducer probes 210, 220, 230, 240, 250, and 260 may also generally conform to the configuration of the interfaces of ultrasound transducer probe 300, including both higher and lower speed interfaces. The ultrasound transducer probe 210 may include the same interfaces 208a and 208b of ultrasound transducer probe 200, located on the peripheral region(s) 212a and/or 212b in some embodiments. For example, in a first embodiment, the peripheral region 212a may include the interfaces of ultrasound transducer probe 200 of FIG. 2A (i.e., four higher speed interfaces 208a and one lower speed interface 208b). In an alternative embodiment, the higher speed interfaces may be split (equally or not) between the peripheral region 212a and the peripheral region 212b. Other configurations are also possible.

Because the ultrasound transducer probes 220, 230, 240, 250, and 260 represent multiple instances of the ultrasound transducer probe 200 or 210, the number of interfaces included may simply scale with the number of instances of the ultrasound transducer probe 200 or 210 making up the ultrasound transducer probes 220, 230, 240, 250, and 260.

The physical interfaces described herein may be suitable for wired connections (e.g., a cable) or wireless connection in some embodiments. Thus, the aspects of the present application relating to an ultrasound transducer probe having two or more different types of interfaces are not limited to whether the interfaces are configured for wired or wireless connection unless otherwise stated.

When a wired connection is made to the interfaces of an ultrasound transducer probe of the types described herein, such connection may be made in any suitable manner. In some embodiments, the ultrasound transducer probe may be enclosed within a package or housing, and one or more ports may be provided for connecting a wire/cable to the ultrasound transducer probe. In some such embodiments, one port for each type of interface of the ultrasound transducer probe may be provided, though alternative configurations are possible. A non-limiting example is illustrated in FIG. 4A.

Figure 4A:
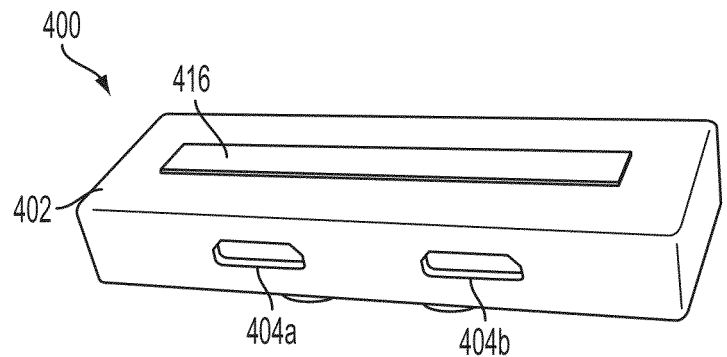
FIGS. 4A and 4B illustrate packaged ultrasound transducer probes with ports providing access to different types of physical interfaces of the ultrasound transducer probe, according to a non-limiting embodiment of the present application.

The device 400 of FIG. 4A represents a non-limiting example of an ultrasound transducer probe 400 including a package 402 (also referred to herein as a "housing"). The package 402 may substantially enclose an ultrasound transducer probe of the types illustrated in FIGS. 2A-2G. The ultrasound transducer probe 400 includes two ports, 404a and 404b which may allow for connection of respective cables to the previously-described interfaces 208a and 208b. For instance, port 404a may be configured to receive a cable connecting to interface 208a and port 404b may be configured to receive a cable connecting to interface 208b. The ports 404a and 404b may be any suitable types of ports for accepting cables (or, more generally, wired connectors such as wired connections 106 and 124) for the types of interfaces implemented on the ultrasound transducer probe.

As a non-limiting example, the port 404b may be suitable for connecting to a USB cable (e.g., wired connection 106 or 124 may be a USB cable). As previously described, interface 208b may, in some embodiments, be a suitable interface for connecting the ultrasound transducer probe to a consumer electronics device. In some such embodiments, the interface 208b may be compatible with a USB connection, since many consumer electronics devices are configured to connect to other devices via USB cables. Thus, the port 404b may be a USB port. However, it should be appreciated that alternatives are possible.

As a non-limiting example, the port 404a may be suitable for connecting to a direct-attach cable, such as a quad small form-factor pluggable (QSFP) cable (e.g., wired connection 106 or 124 may be a QSFP cable). As previously described, the ultrasound transducer probe 200 may include multiple interfaces 208a (or, stated another way, multiple instances of the interface 208a), yet in some embodiments only a single cable may be needed to connect the interfaces to an external device, and thus only a single port 404a may be provided. For example, use of a QSFP cable may allow for connection of a single cable to four of the interfaces 208a. In this manner, the number of interfaces of the ultrasound transducer probe to which any external device is connected may be determined by the cable used to connect the ultrasound transducer probe 400 to the external device, which may render transparent the process of selecting how many interfaces to connect to.

In some embodiments, a single cable may be used for each interface of the ultrasound transducer probe to which an external device is to be connected. In such instances, the ultrasound transducer probe 400 may include a port corresponding to each of the physical interfaces 208a and 208b.

It should be appreciated that in operation the ultrasound transducer probe 400 may be connected to an external device by a single cable at a time. That is, the user may select whether to utilize the interface 208a or the interface 208b, and thus connect a single cable to the appropriate port 404a or 404b.

Figure 4B:
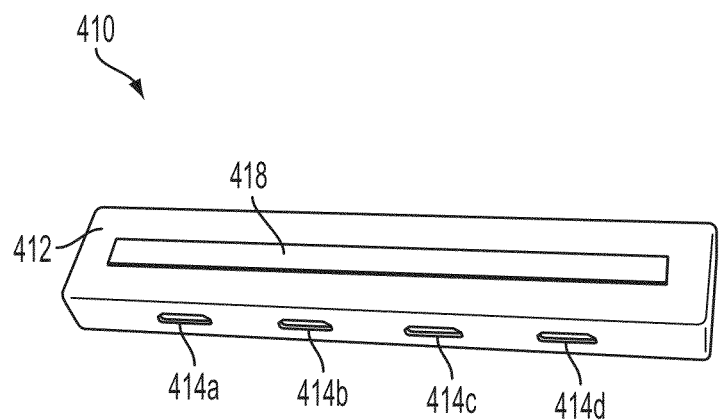

FIG. 4B illustrates an alternative ultrasound transducer probe 410 to that of FIG. 4A. The ultrasound transducer probe 410 represents a non-limiting example of an ultrasound transducer probe including a package and may represent a packaged version of ultrasound transducer probe 220 of FIG. 2C, i.e., including two instances of the ultrasound transducer probe 200 of FIG. 2A. The ultrasound transducer probe 410 includes a package (or housing) 412 and four ports 414a-414d. Two of the four ports (e.g., ports 414a and 414c) may be configured to connect interfaces of the type of interface 208a to an external device via a suitable cable, while the other two ports (e.g., ports 414b and 414d) may be configured to connect interfaces of the type of interface 208b to an external device via a suitable cable. Thus, it should be appreciated that in operation the ultrasound transducer probe 410 may be connected to an external device by two cables at a time, in some embodiments.

In some embodiments, the package or housing of an ultrasound device may limit accessibility to one or more interfaces of the ultrasound transducer probe. The point may be illustrated by considering the ultrasound transducer probe 200 of FIG. 2A, having interfaces 208a and 208b. In some embodiments, the ultrasound transducer probe 200 may be packaged with a package that has one or more ports providing access only to the interface 208a, or alternatively only to the interface 208b. Such a configuration may allow for production and distribution of ultrasound devices to target consumers without needing to change the underlying design of transducer probe 200 (e.g., not all consumers may want or need to have the option of connecting the ultrasound transducer probe via the two or more types of interfaces).

Although some embodiments have been described in which multiple types of interfaces are provided with an ultrasound transducer probe, not all embodiments are limited in this respect. In some embodiments, only a single type of interface may be provided on the probe. For example, in some embodiments, an ultrasound transducer probe like that of FIG. 2A may lack the interface 208a or 208b.

Architecture

As previously described, various features of an ultrasound transducer probe may facilitate use of the transducer probe as a stand-alone ultrasound transducer probe (e.g., a stand-alone or self-contained 1D, 1.5D or 2D ultrasound transducer probe) or as a component of a larger ultrasound device formed by tiling and interconnection of multiple instances of the transducer probe. One such feature is the physical architecture of the transducer probe, including the geometry of the transducer probe and the positioning of ultrasonic transducers and integrated circuitry of the transducer probe.

Form Factor of Ultrasound Transducer Probes

The geometry of the ultrasound transducer probe may be selected to provide a desired aperture, which may facilitate tiling and interconnection of multiple instances of the transducer probe to form a larger ultrasound device having a desired aperture. In some embodiments, an ultrasound transducer probe may have a first side longer than a second side, where the first side is substantially perpendicular to the second side. The sides may represent sides of a device surface on which ultrasonic transducers and/or circuitry are formed. As an example, the ultrasound device 100 of FIG. 1 has a first side representing a width W1 and a second side representing a height H1. As previously described, W1 may be greater than H1. FIGS. 2A and 2B also illustrate the point. In some such embodiments, the transducer probe may be a wide aspect ratio transducer probe. In some embodiments, the width to height ratio may be greater than or equal to 3:1, greater than or equal to 4:1, greater than or equal to 5:1, greater than or equal to 10:1, between 2:1 and 15:1, between 4:1 and 10:1, any range or value within such ranges, or any other suitable aspect ratio.

As has been described, in some embodiments an ultrasound transducer probe includes a substrate, such as a semiconductor or CMOS substrate (e.g., substrate 202 of transducer probe 200). In any of those embodiments in which the transducer probe has one side longer than another perpendicular side (e.g., when the transducer probe is a wide aspect ratio transducer probe), the dimensions may refer to the dimensions of the substrate.

Referring to FIG. 3, the substrate 302 may be any suitable substrate and in some embodiments may be a semiconductor substrate or CMOS substrate, such as a silicon substrate, a silicon-on-insulator (SOI) substrate, or an engineered substrate. In some embodiments, the substrate 302 may be a CMOS substrate suitable for supporting integrated circuitry, such as integrated circuitry 306. Likewise, the substrate 202 of ultrasound transducer probe 200 may be any of those types of substrates listed.

In some embodiments the use of an ultrasound transducer probe having one side longer than a perpendicular side (e.g., a wide aspect ratio transducer probe) may provide benefits in terms of the aperture of the transducer probe. For example, such a configuration may facilitate creation of a suitable 1D transducer probe aperture. Thus, in some embodiments, the dimensions of an ultrasound transducer probe (e.g., ultrasound transducer probes 200 and 210) may be selected to provide a desired aperture (e.g., a desired 1D aperture or 2D aperture). In some embodiments, a transducer probe having a width of between approximately 30 mm and approximately 40 mm and having a height between approximately 2 mm and approximately 8 mm may provide a suitable 1D aperture, allowing for suitable focusing of an ultrasound beam in the height dimension.

The ultrasonic transducers of an ultrasound transducer probe may assume a configuration suitable for providing a desired aperture. For example, referring to FIG. 2A, the plurality of ultrasonic transducers 204 may assume a configuration in which the transducers are arranged along a greater distance in the direction of the width W1 than in the direction of the height H1, and in some embodiments may be arranged suitably to provide a desired 1D, 1.5D, or 2D aperture. In some embodiments, the plurality of ultrasonic transducers (e.g., ultrasonic transducers 204 or 304) may be arranged in an array, though alternative arrangements are possible.

One or more lensing components may be provided with the ultrasound transducer probe to control the focus of the ultrasound transducer probe. For example, an acoustic lens may be provided overlying the ultrasonic transducers to focus transmitted and/or received acoustic signals. The acoustic lens may assume any suitable configuration for providing desired lensing functionality and may be formed of any suitable material. For example, referring to FIGS. 4A and 4B, reference numbers 416 and 418 may represent acoustic lenses. The acoustic lenses may have a curved (e.g., convex) geometry when viewed in cross-section, in some embodiments. The curvature may be in the elevation dimension (e.g., in the direction of the height H1 referring to FIG. 2A, as an example) in some embodiments, although curvature in other dimensions or a combination of two dimensions is possible.

Any suitable number of ultrasonic transducers may be provided on an ultrasound transducer probe, as the number is not limiting of the various aspects described herein. In some embodiments, tens, hundreds, thousands, hundreds of thousands, or millions of ultrasonic transducers may be provided on an ultrasound transducer probe. As a non-limiting example, the plurality of ultrasonic transducers 204 of ultrasound transducer probe 200 may include an array of sixteen rows (parallel to the width W1) of ultrasound elements with each row of ultrasound elements having 128 ultrasound elements. The same may be true for the ultrasound transducer probe 210 of FIG. 2B. Thus, ultrasound transducer probe 220 of FIG. 2C may include sixteen rows of ultrasound elements with each row having 256 ultrasound elements. Ultrasound transducer probe 230 may include an array of 64 rows of ultrasound elements with each row having 128 ultrasound elements. Ultrasound transducer probe 240 may include an array of 128 rows of ultrasound elements with each row having 128 ultrasound elements. Ultrasound transducer probe 250 may include an array of 64 rows of ultrasound elements with each row including 256 ultrasound elements. Ultrasound transducer probe 260 may include 128 rows of ultrasound elements with each row including 256 ultrasound elements. In any such embodiment, each ultrasound element may have one or more ultrasonic transducers. An example is now described in connection with FIGS. 5A and 5B.

Figure 5A:
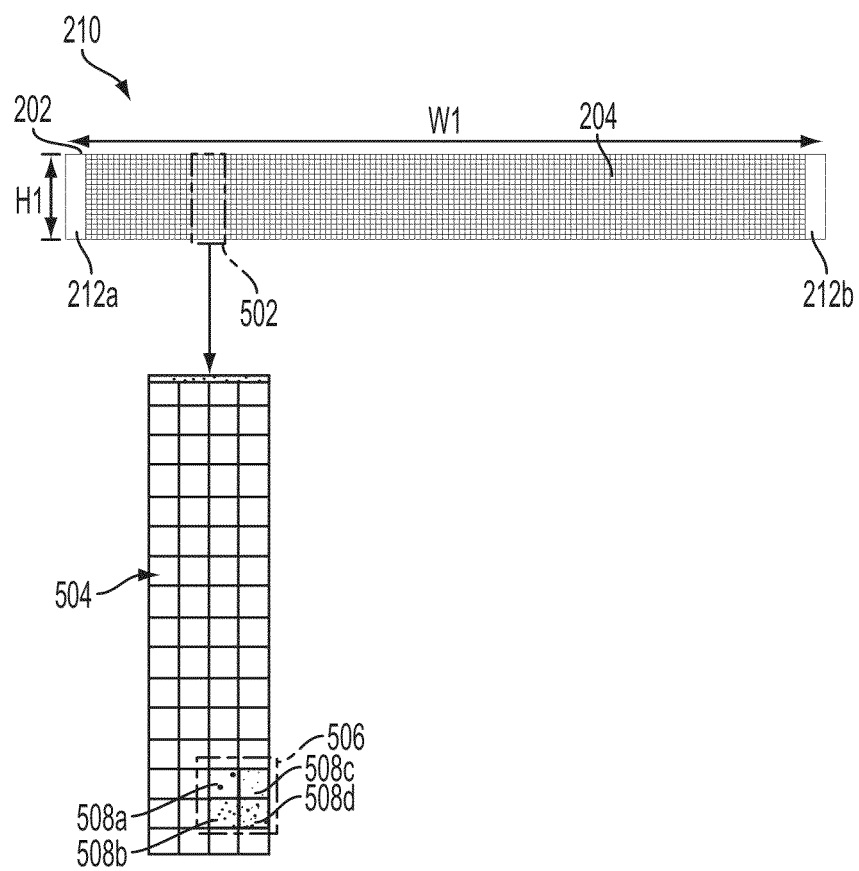
FIGS. 5A and 5B illustrate a non-limiting example of ultrasonic transducers (or transducer cells) arranged into transducer elements to form part of an ultrasound transducer probe, according to a non-limiting embodiment of the present application.

FIG. 5A replicates FIG. 2B with the addition of an enlarged inset 502. As shown in the inset 502, the ultrasound transducer probe 210 may include sixteen rows (arranged along the height H1) of ultrasound elements 504. The ultrasound transducer probe 210 may include 128 columns of ultrasound elements 504 extending substantially across the width W1, except not covering the peripheral regions 212a and 212b. The ultrasound elements 504 are illustrated as being square, but need not be in all embodiments.

Figure 5B:
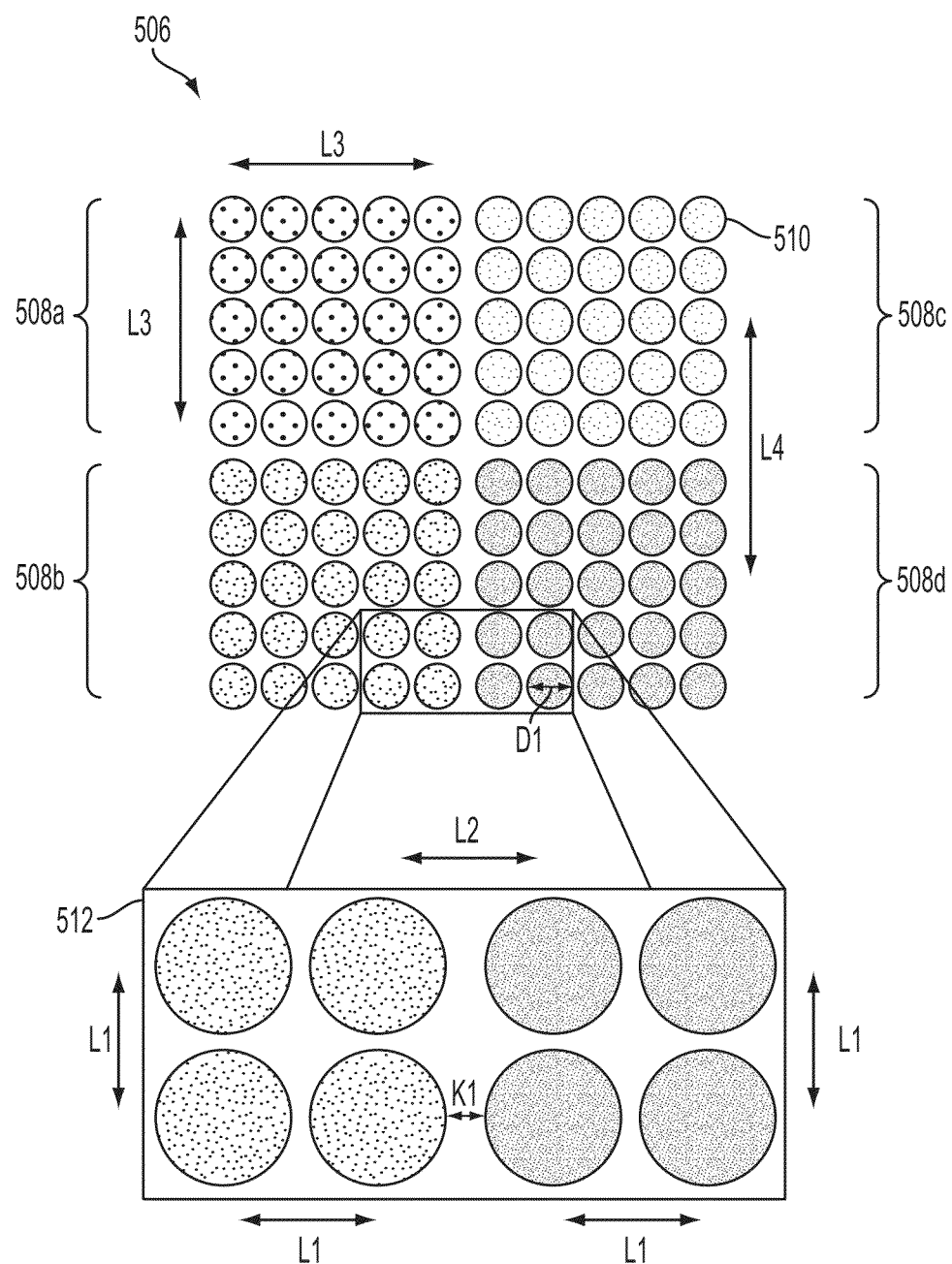

In some embodiments, the ultrasound elements (e.g., element 504) may include one or more ultrasonic transducers (also referred to herein as "transducer cells"). Stated differently, the ultrasonic transducers may be grouped together to form ultrasound elements. The concept is illustrated in connection with cluster 506 of ultrasound elements 508a-508d, enlarged in FIG. 5B. Referring to FIG. 5B, each of the illustrated ultrasound elements 508a-508d includes a 5×5 arrangement of ultrasonic transducers 510, though other arrangements and other numbers of ultrasonic transducers may be included in an ultrasound element.

The ultrasonic transducers 510 may be CMUTs, CUTs, or other suitable ultrasonic transducers. The ultrasonic transducers 510 are illustrated as being circular (from a top view) but may have any suitable geometry. The ultrasonic transducers 510 within an element 504 may be electrically interconnected to operate as a single element rather than as individually controllable transducers. For example, the transducers may have one or more common electrodes to provide unified operation.

FIG. 5B illustrates a non-limiting example of the spacing of the ultrasonic transducers 510 and the ultrasound elements 508a-508d. The ultrasonic transducers 510 may have diameters D1 of approximately 50 microns, between approximately 30 microns and approximately 70 microns, any value within that range, or any other suitable diameter. The inset 512, which provides an expanded view of a portion of ultrasound elements 508b and 508d, shows that the ultrasound elements may be spaced by a kerf k1 of approximately 10 microns (or any other suitable distance) such that the center-to-center distance L2 between ultrasonic transducers 510 of neighboring ultrasound elements 504 may be, for example, approximately 60 microns. Providing such spacing between ultrasound elements may allow for running signal lines between the elements and/or reducing acoustic cross-talk between the ultrasound elements. However, in some embodiments the ultrasound elements may not have any additional spacing between them other than the spacing between individual ultrasonic transducers. As an example, the spacing between ultrasound transducers 510 within an ultrasound element may be approximately 2 microns.

The transducer cell pitch L1 of the ultrasonic transducers may be approximately 52 microns or any other suitable value. The length L3 of an ultrasound element of the type illustrated in FIG. 5B may be approximately 258 microns or any other suitable value. The ultrasound element pitch L4 of neighboring ultrasound elements may be approximately 268 microns or any other suitable value. It should be appreciated that the values of the distances shown in FIG. 5B are non-limiting, and that alternative values for the element size, transducer size, cell and element pitches, and the kerf are possible.

Figure 5C:
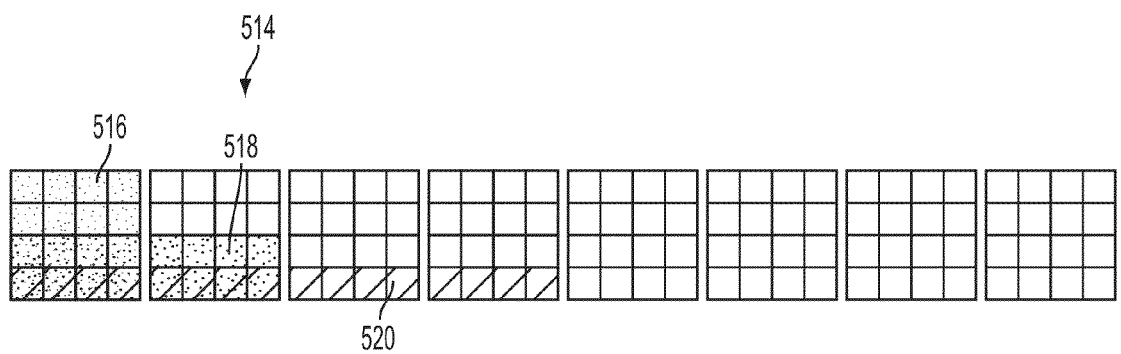
FIG. 5C illustrates different configurations of ultrasound elements which may be formed from a common arrangement of ultrasonic transducers.

While FIG. 5B illustrates a non-limiting example of a configuration of an ultrasound element including a 5×5 arrangement of ultrasonic transducers, variations are possible. In some embodiments, the configuration of ultrasonic transducers defining an ultrasound element may be configurable during manufacture of the device via choice of a metallization layer. That is, in some embodiments the ultrasonic transducers may be microfabricated and selection of a metal layer interconnecting multiple ultrasonic transducers may be used to define ultrasound elements of a desired configuration. FIG. 5C illustrates an example.

FIG. 5C illustrates a plurality of ultrasonic transducers 514. In this example, the ultrasonic transducers are laid out substantially in a repeating array of 4×4 blocks, which represents an example of a configuration of ultrasonic transducers on an ultrasound transducer probe. From this arrangement of ultrasonic transducers, different ultrasound element configurations may be created via choice of a metallization layer. Three different potential ultrasound element configurations are illustrated. Namely, a 4×4 element 516 may be created. Alternatively a 2×8 element 518 may be created. As a third option, a 1×16 element 520 may be created. Depending on the configuration chosen, the remaining ultrasonic transducers 514 may be grouped into similarly configured ultrasound elements. For example, all the illustrated ultrasonic transducers 514 may be grouped into 4×4 elements, or into 2×8 elements, or into 1×16 elements. These differing configurations may be formed with an underlying arrangement of ultrasonic transducers (e.g., the arrangement of ultrasonic transducers 514) simply by patterning a metallization layer appropriately (i.e., in the illustrated configurations) to serve as a common electrode for the ultrasonic transducers within each element. Thus, configurability of ultrasound transducer elements may be provided during the manufacturing process.

Such configurability may be utilized to facilitate certain operating modes. Examples of ultrasound imaging modes which may be implemented by ultrasound transducer probes according to aspects of the present application are described further below. A particular ultrasound element configuration (e.g., one of the configurations shown in FIG. 5C) may be utilized to facilitate implementation of a particular imaging mode.

The physical placement of the circuitry of an ultrasound transducer probe of the types described herein may also facilitate the use of the ultrasound transducer probe as a stand-alone ultrasound transducer probe or as a component of a larger transducer probe formed by tiling and interconnection of multiple instances of the transducer probe. As previously described, in some embodiments the ultrasound transducer probe may include a CMOS substrate and integrated circuitry. In some embodiments, at least some circuitry of the ultrasound transducer probe may be positioned beneath the ultrasonic transducers of the transducer probe. In some embodiments, some of the integrated circuitry may be positioned on the peripheral region (or "tab") of the ultrasound transducer probe. For instance, circuitry which is shared among two or more of the ultrasonic transducers or ultrasound elements may be positioned on the peripheral region. Yet, circuitry specific to an ultrasound element or to a particular ultrasonic transducer may be positioned beneath that ultrasound element or ultrasonic transducer in some embodiments. A non-limiting example is shown in FIG. 6.

Placement of Ultrasonic Transducers and Circuitry

Figure 6:
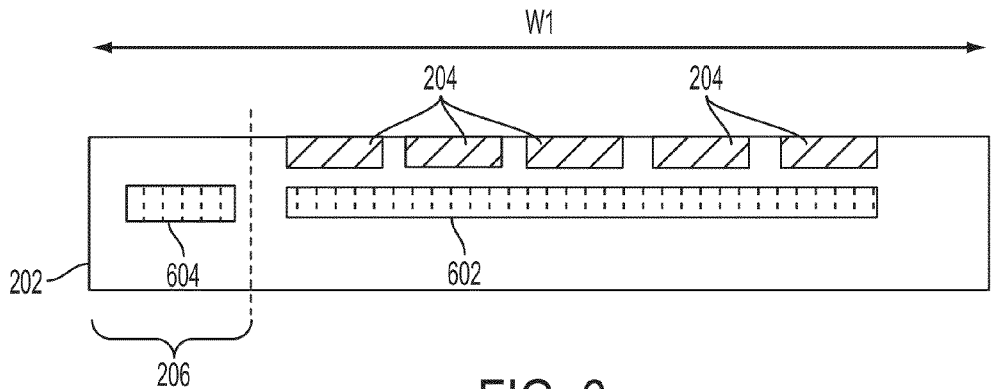
FIG. 6 illustrates a cross-sectional view of an ultrasound transducer probe having integrated circuitry beneath ultrasonic transducers of the ultrasound transducer probe as well as integrated circuitry on a peripheral region of the ultrasound transducer probe, according to a non-limiting embodiment of the present application.

FIG. 6 illustrates a simplified cross-sectional view of an ultrasound transducer probe having ultrasonic transducers and integrated circuitry on a substrate. For instance, FIG. 6 may represent a cross-section of the ultrasound transducer probe 200 of FIG. 2A taken into and out of the page of FIG. 2A and along the width W1. As shown, the substrate 202 may have the plurality of ultrasonic transducers 204 formed thereon, which may be arranged in ultrasound elements. In some embodiments, the ultrasonic transducers 204 may be integrated with (e.g., monolithically integrated with) the substrate 202. For instance, the substrate 202 may be a CMOS substrate and the ultrasonic transducers 204 may be CUTs or CMUTs monolithically integrated with the substrate 202.

As shown, the ultrasound transducer probe of FIG. 6 may further include integrated circuitry 602 and 604, which may be considered in some embodiments to form a single integrated circuit. The integrated circuitry 602 and/or 604 may include circuitry for controlling operation of the ultrasonic transducers 204 (e.g., transmit and receive circuitry) and/or processing of signals received by the ultrasonic transducers (e.g., decimation and filtering) and/or for interfacing the ultrasound transducer probe with an external device (e.g., interfaces 208a and 208b). As shown, the integrated circuitry 602 may be positioned (or disposed or placed) beneath the ultrasonic transducers 204. Such a configuration may conserve chip area, allowing for the ultrasound transducer probe to be more compact than would be possible if the integrated circuitry 602 was in-plane with the ultrasonic transducers 204. The integrated circuitry 602 and the ultrasonic transducers 204 may be connected in any suitable manner, non-limiting examples of which are described further below, for example in connection with FIG. 36. For example, the integrated circuitry 602 and ultrasonic transducers 204 may be connected by one or more vias between an ultrasonic transducer and a metallization layer of the substrate 202.

In some embodiments, the integrated circuitry 602 may be arranged into IC cells corresponding to the ultrasonic transducers or to ultrasound elements of the type described in connection with FIG. 5A. For example, transmit and/or receive circuitry specific to a particular ultrasonic transducer 204 or ultrasound element may be disposed beneath that ultrasonic transducer or element. As a non-limiting example, the integrated circuitry 602 may include a low-noise amplifier (LNA) for each ultrasound element of the ultrasound transducer probe, and each LNA may be positioned beneath the respective ultrasound element. In some embodiments, a first transistor of the LNA may be positioned beneath the respective ultrasound element and the remainder of the LNA positioned elsewhere (e.g., in a peripheral region). The LNA may be a transimpedance amplifier (TIA) in some embodiments, and in others may be a transconductance amplifier, voltage amplifier, or current amplifier, as non-limiting examples. In some embodiments, a waveform generator for each ultrasound element may be positioned beneath the ultrasound element.

As shown, the integrated circuitry 604 may be positioned on the peripheral region 206 (indicated as being to the left of the vertical dashed line). In some embodiments, the integrated circuitry 604 may include circuitry which is not specific to any particular transducer of the ultrasound transducer probe. For example, timing circuitry, I/O circuitry, power conversion circuitry, or other circuitry which may be shared among multiple transducers or elements, or shared among all of the transducers may be positioned on the peripheral region 206 in some embodiments. Other circuit components may additionally or alternatively be included on the peripheral region 206. Furthermore, in some embodiments, all integrated circuitry of the ultrasound transducer probe may be positioned beneath the ultrasonic transducers, which may minimize the chip area required for the ultrasound transducer probe.

Ultrasound Transducer Probe Circuitry

The architecture of the ultrasound transducer probe circuitry may include further features facilitating the use of the ultrasound transducer probe as a stand-alone probe or as a component of a larger ultrasound device formed by tiling and interconnection of multiple instances of the transducer probe. For example, the circuitry of the transducer probe may include digitization circuitry (e.g., analog-to-digital converters (ADCs)). Such digitization circuitry may digitize signals from the ultrasonic transducers such that the ultrasound transducer probe may communicate the ultrasound data to an external device in digital form (e.g., via a USB cable or other interface of the types described herein). Thus, aspects of the present application provide digital ultrasound transducer probes. Examples of suitable digital circuitry are described further below and may include, for example, analog-to-digital converters (ADCs), multiplexers, re-quantizers, averaging circuits, and communication interfaces, among others.

Another feature of the ultrasound transducer probe circuitry which may facilitate the use of the ultrasound transducer probe as a stand-alone probe or as a component of a larger ultrasound device formed by tiling and interconnection of multiple instances of the transducer probe is the programmable nature of the circuitry. The use of programmable circuitry may allow the ultrasound transducer probe to be programmed to work suitably in combination with other such ultrasound transducer probes (e.g., when two or more ultrasound transducer probes are tiled to form a larger ultrasound transducer probe). Also, the use of programmable circuitry may support various ultrasound imaging modes. In some embodiments, the programmable circuitry may include a programmable waveform generator. Non-limiting examples of such waveform generators as well as other circuitry of an ultrasound transducer probe are described further below.

Figure 7:
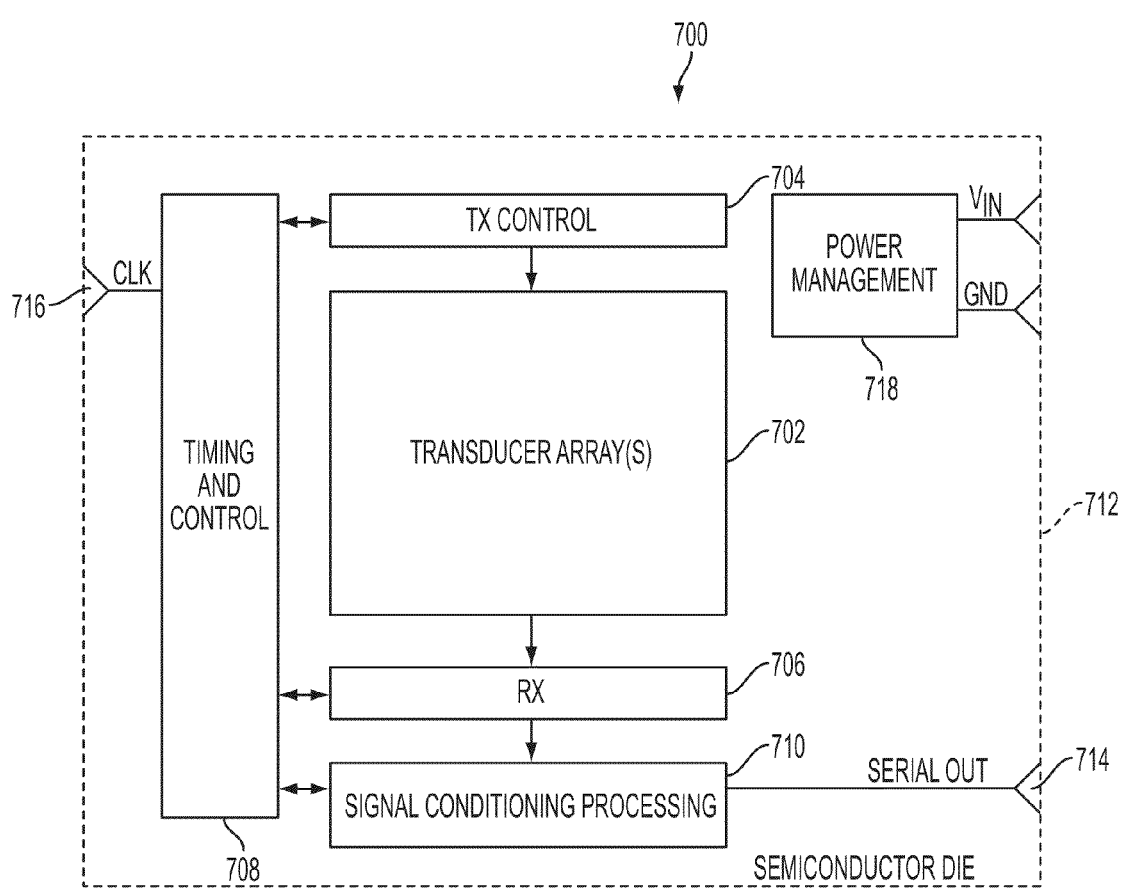
FIG. 7 is a schematic diagram illustrating the circuitry architecture of an ultrasound transducer probe according to a non-limiting embodiment of the present application.

The control circuitry of an ultrasound transducer probe of the types described herein (e.g., integrated circuitry 306 of ultrasound transducer probe 300) may include any suitable circuitry for controlling, at least in part, transmission and/or receiving functions of the plurality of ultrasonic transducers of the transducer probe (e.g., ultrasonic transducers 304). FIG. 7 illustrates a non-limiting example of a suitable configuration for the circuitry of an ultrasound transducer probe.

The ultrasound transducer probe 700 includes one or more transducer arrangements (e.g., arrays) 702, a transmit (TX) control circuit 704, a receive (RX) circuit 706, a timing and control circuit 708, a signal conditioning/processing circuit 710, and/or a power management circuit 718 receiving ground (GND) and voltage reference ($V_{IN}$) signals. Optionally, a HIFU controller (not shown) may be included if the ultrasound transducer probe is to be used to provide HIFU. In the embodiment shown, all of the illustrated elements are formed on a single semiconductor die (or substrate or chip) 712, though not all embodiments are limited in this respect. In addition, although the illustrated example shows both a TX control circuit 704 and an RX circuit 706, in alternative embodiments only a TX control circuit or only an RX control circuit may be employed. For example, such embodiments may be employed in a circumstance in which the ultrasound transducer probe is operated as a transmission-only device to transmit acoustic signals or a reception-only device used to receive acoustic signals that have been transmitted through or reflected by a subject being ultrasonically imaged, respectively.

The ultrasound transducer probe 700 further includes a serial output port 714 which may represent an implementation of an interface of the types previously described herein (e.g., interface 308a or 308b). While only a single output port 714 is illustrated, it should be appreciated that multiple output ports may be provided, consistent with the ultrasound transducer probe 700 having multiple interface types.

The ultrasound transducer probe 700 may also include a clock input port 716 to receive and provide a clock signal CLK to the timing and control circuit 708.

It should be further appreciated from the components of ultrasound transducer probe 700 that a complete ultrasound system-on-a-chip may be provided in accordance with some embodiments. Not all embodiments are limited to such a configuration, however.

Figure 8:
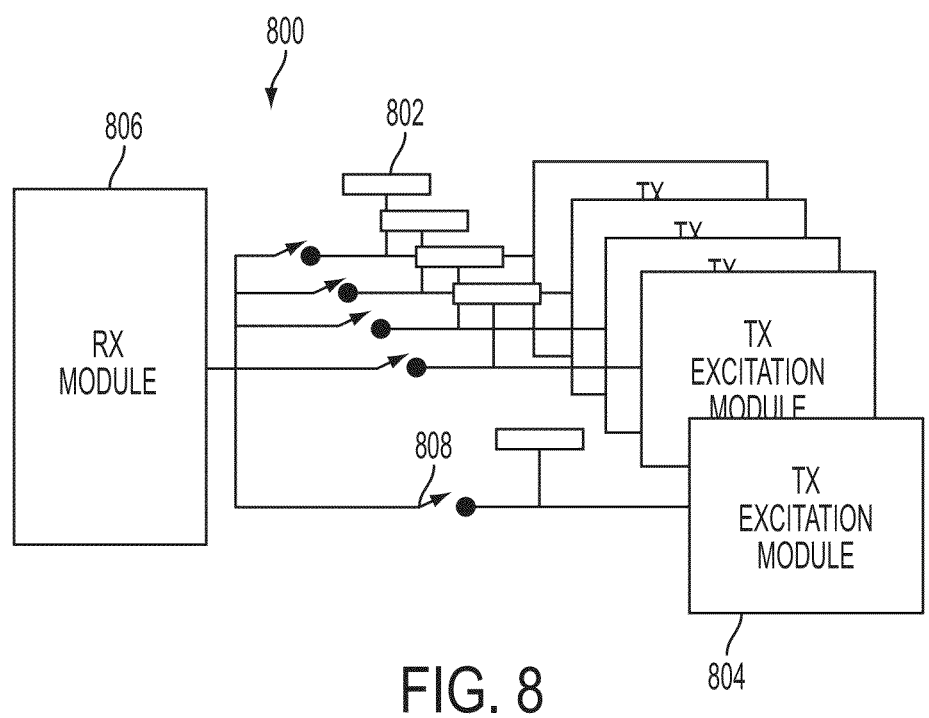
FIG. 8 illustrates a configuration of circuitry of an ultrasound transducer probe in which multiple ultrasound elements are associated with respective transmit excitation modules and share a receive module, according to a non-limiting embodiment of the present application.

In some embodiments, the control circuitry of an ultrasound transducer probe may be configured to reduce the amount of data to be sent from the transducer probe to an external device. Reducing the amount of data may facilitate use of the ultrasound transducer probe for high end applications, such as high end ultrasound imaging applications. According to some embodiments, the amount of data provided externally from the ultrasound transducer probe may be reduced by including fewer receive signal channels than the probe contains ultrasound elements, such that multiple ultrasound elements share a receive signal channel. Thus, the receive circuit 706 and signal conditioning/processing circuit 710 may be shared among multiple ultrasound elements. A non-limiting example is illustrated in FIG. 8.

As shown, the circuitry configuration 800 includes a plurality of ultrasound elements 802, which may be of the types previously described herein or any other suitable type. For example, the ultrasound elements 802 may each be like an ultrasound element 508a, previously described. A respective transmit excitation module 804 may be provided for each of the ultrasound elements 802. However, multiple ultrasound elements 802 share a single receive module 806. For example, the illustrated ultrasound elements 802 may each be coupled to the receive module 806 by a respective switch 808. In this manner, the amount of receive circuitry implemented on the ultrasound transducer probe may be reduced and the amount of data provided by the ultrasound transducer probe to an external device may be more readily reduced to an amount which can be communicated serially.

In those embodiments in which multiple ultrasound elements 802 share a single receive module 806, the number of ultrasound elements 802 sharing the receive module 806 may be any suitable number to provide a desired reduction in receive circuitry compared to providing a respective receive module for each ultrasound element. Referring to FIG. 5A and considering the ultrasound transducer probe 210 as a non-limiting example, two receive circuits (e.g., two receive modules 806) may be provided for each column of ultrasound elements 504, such that eight ultrasound elements 504 may share a single receive circuit. However, this is a non-limiting example, as any two or more ultrasound elements may share a receive circuit in those embodiments in which multiple ultrasound elements share a receive circuit.

The switches 808 may be operated in any suitable manner to provide desired receive functionality. For example, all the switches 808 may be open, disconnecting the receive module 806 from the ultrasound elements 802, when the ultrasound elements 802 are transmitting ultrasound signals. When the ultrasound elements 802 are receiving ultrasound signals, the switches 808 may be sequentially closed to read signals out of the ultrasound elements 802 sequentially, as a non-limiting example.

Figure 9:
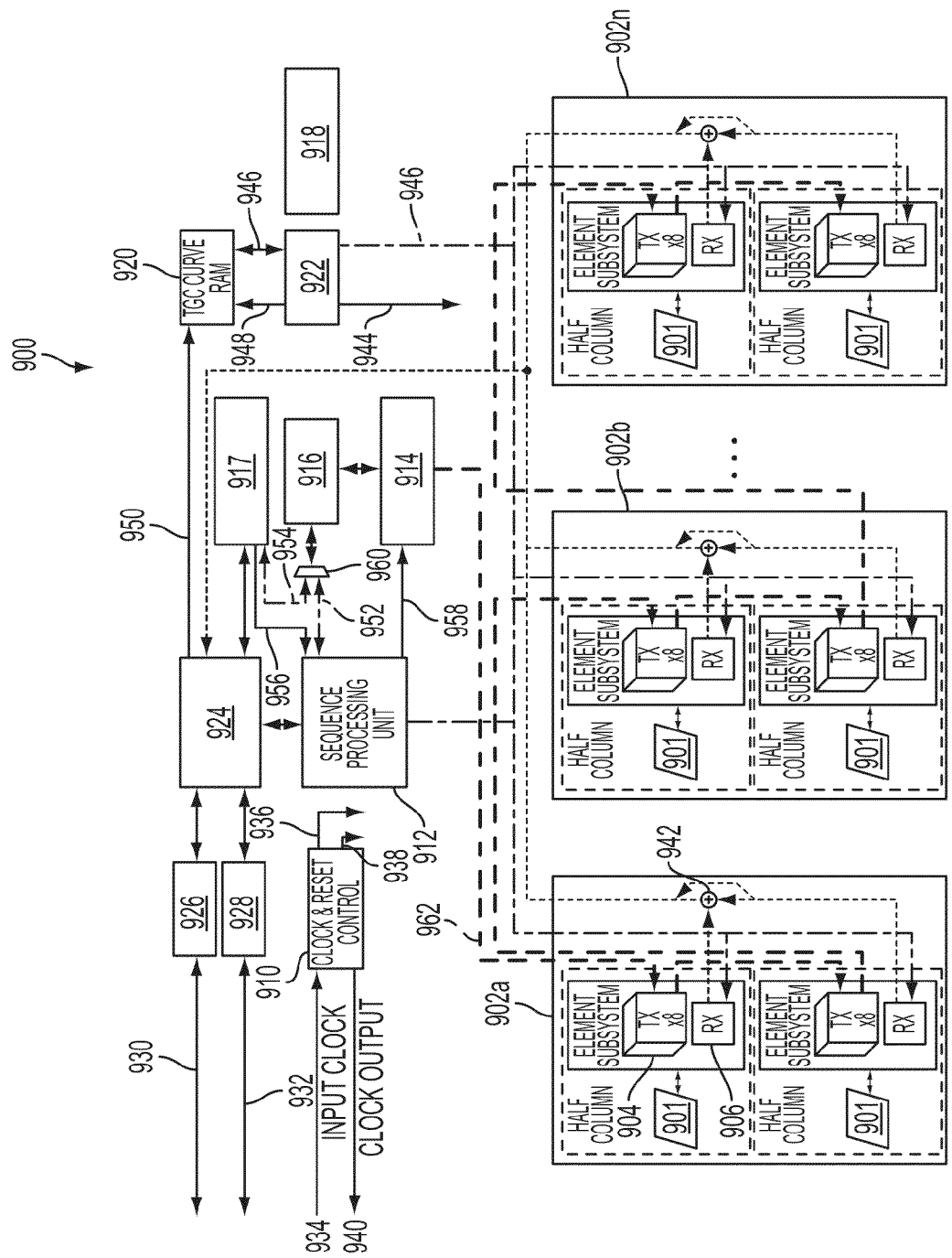
FIG. 9 illustrates a non-limiting detailed implementation of the ultrasound transducer probe of FIG. 7 in which the configuration of FIG. 8 is implemented.

FIG. 9 illustrates a non-limiting example of the control circuitry of an ultrasound transducer probe of the types described herein which may be used as a universal building block ultrasound transducer probe for tiling and interconnection with other such ultrasound transducer probes. Thus, the ultrasound transducer probe 900 represents a non-limiting detailed implementation of the circuitry of ultrasound transducer probe 700 of FIG. 7, and conforms to the configuration of FIG. 8 in that multiple ultrasound elements share a receive module.

The ultrasound transducer probe 900 includes a plurality of ultrasound elements 901 which, for purposes of illustration, are described as being arranged in columns. For example, the ultrasound elements 901 may be arranged in columns in the manner previously described in connection with ultrasound transducer probe 210 as shown in FIG. 5A. In the non-limiting example of FIG. 9, each occurrence of "901" represents eight ultrasound elements, such that each illustrated column includes 16 ultrasound elements.

Certain circuitry of the ultrasound transducer probe 900 is associated with respective columns of the ultrasound elements 901 and thus is described as being part of a column module, each of which is shown as being divided into two half-columns. Other circuitry is more generally associated with the plurality of ultrasound elements 901 rather than any particular column of ultrasound elements and thus may be considered separate from the column modules.

The ultrasound transducer probe 900 includes column modules 902a, 902b . . . 902n, where n is the total number of columns of ultrasound elements. As a non-limiting example, n may be 128, may be between 50 and 150, any value within that range, or any other suitable value. The column modules 902a . . . 902n may each include a subset of the ultrasound elements 901, one or more transmit circuitry modules 904 and one or more receive circuitry modules 906. In the non-limiting example shown, each column module 902a . . . 902n may include 16 ultrasound elements 901, two receive circuitry modules 906 coupled to respective groups of eight ultrasound elements 901 (i.e., one receive circuitry module per 8 ultrasound elements), and 16 transmit circuitry modules 904 coupled to respective ultrasound elements 901 (i.e., one transmit circuitry module 904 per ultrasound element 901). The receive circuitry modules 906 may be coupled to each ultrasound element 901 of a respective group of ultrasound elements 901 by a switch in the manner previously illustrated in FIG. 8, or in any other suitable manner. The transmit circuitry modules 904 are connected to each other in a daisy-chain configuration as illustrated by the arrows 962, which may represent a wired connection (e.g., a data line), and also connected to the excitation parameter loader 914, described further below.

The ultrasound transducer probe may operate by loading transmit parameters defining a sequencing operation into the transmit circuitry modules of the column circuitry. In some embodiments, the sequencing information may be pushed to each ultrasound element of the ultrasound transducer probe by pushing the sequencing information to the waveform generator associated with the ultrasound elements. The transmit parameters may be loaded in a daisy-chain configuration, being passed from one transmit circuitry module to the next, as indicated by the arrows 962. In some embodiments, the transmit parameters are loaded into the transmit circuitry modules when the ultrasound transducer probe is operating in a receive mode.

Control of the sequencing of transmit and/or receive functions performed by the ultrasound transducer probe 900 may be achieved with the sequence processing unit (SPU) 912, which may be a microcontroller or other suitable hardware. For example, the SPU 912 may provide a desired sequence of transmission and/or reception events.

Various components of the ultrasound transducer probe 900 may operate in conjunction with the SPU 912. For instance, an excitation parameter loader 914 is included and loads suitable control parameters into the transmit circuitry modules 904 in response to a control signal 958 from the SPU 912. A SPU memory 916 is also included to store the sequencing parameters for the SPU 912, including transmit and receive parameters and parameters for controlling other components (such as data interface components) of the ultrasound transducer probe. A program management unit (PMU) 917 may handle program loading into the SPU 912, and may be a dedicated piece of hardware. The PMU 917 and SPU 912 may communicate data and address information with the SPU memory 916 via control lines 954 and 952, respectively, with the help of a multiplexer 960. The PMU 917 may also provide a reset signal 956 to the SPU 912.

The SPU 912 may run a stored program to configure and sequence the actions of the ultrasound transducer probe 900. Thus, the details of an imaging mode of operation may be encoded into a reconfigurable stored program loaded into the SPU 912. As described previously, the PMU 917 may control loading of the program into the SPU 912. The PMU 917 may be directly accessible from the external device (e.g., a host computer) over the external data links 930 and 932 connected to the interface circuits 926 and 928, respectively. When commanded by the host computer, the PMU 917 may hold the SPU 912 in reset and take direct control of the SPU memory 916. Program code from the host computer may then be written directly into the SPU memory 916. After the program has been transferred, the PMU 917 may return the SPU memory 916 to the SPU 912 and release the SPU 912 from reset. The new program may then begin executing per the program's reset vector.

The SPU 912 may be loaded with a suitable program at any suitable times. In some embodiments, the SPU 912 may be loaded with a program at power-on and reset of the ultrasound transducer probe 900. In some embodiments, the stored SPU program may also be replaced during operation of the ultrasound transducer probe 900 as the host computer or other external device changes imaging modes. Thus, the SPU 912 may exhibit semi-autonomous operation. That is, The SPU 912 may operate without a constant stream of configuration data from the host computer, which may eliminate performance bottlenecks caused by latency and congestion on the external data links.

Various benefits may be realized by operation of the SPU 912 in the manner described. For example, when multiple instances of the ultrasound transducer probe 900 are tiled and interconnected, each may run its own unique copy of the SPU program. The programs may or may not be identical depending on what the host computer is trying to achieve. In this manner, coordinated operation of the multiple instances of the repeatable ultrasound building block may be achieved. Cascaded or common clocks and sync pulses may be used to coordinate execution between multiple such ultrasound transducer probes, described further below in connection with FIG. 14.

The operation of the SPU 912 as described may also provide flexibility to the ultrasound transducer probe 900. For example, the ultrasound transducer probe is not restricted to the imaging modes encoded on the chip during the design phase. Additional imaging modes can be achieved simply by changing the stored program for the SPU.

Moreover, verification of operation of the ultrasound transducer probe 900 may be relatively simple. That is, accuracy of operation may be verified by ensuring the SPU 912 can communicate with any external imaging hardware through the designated interfaces, without the need to verify the operation of many hardware state machines.

The timing of operation of the ultrasound transducer probe 900 may be controlled in any suitable manner. In the example shown, the ultrasound transducer probe 900 includes a clock and reset control circuit 910 for controlling the clocking of the circuitry (e.g., the transmit and receive circuitry modules). For example, the clock and reset control circuit 910 may receive an input clock 934 (e.g., from an external oscillator), and provide a global clock 936 and/or a global reset signal 938. An external clock 940 may also be provided as an output.

The ultrasound transducer probe 900 also includes a reference voltage/current circuitry module 918 to monitor and provide reference voltages/currents to the column circuitry. The reference voltage/current circuitry module 918 may take any suitable form.

The ultrasound transducer probe 900 also includes interface circuitry for communicating electrical signals between the ultrasound transducer probe and an external device (e.g., a tablet computer or other host computer). The interface circuitry includes a first interface circuit 926 and a second interface circuit 928, which may be any of the types previously described herein or any other suitable types of interface circuits. An external communication module 924 may facilitate communication between the ultrasound transducer probe 900 and any external device, and may be coupled to the interface circuits 926 and 928. The external communication module 924 may be hardware and may take any suitable form.

The external communication module 924 may also be used in providing data from the receive circuitry modules 906 to an external device. As shown by the arrows, each of the receive circuitry modules 906 may be configured to provide data to the external communication module 924. Different operating modes for doing so are possible. In one mode, each of the receive circuitry modules 906 may provide its data to the external communication module, i.e., data for each half-column may be separately provided to the external communication module 924. In another mode, data from the two half-columns forming a column may be provided to the external communication module 924 using the adders 942. In particular, the data from the receive circuitry modules 906 of the two half-columns of a column may be combined by the adder 942 of that column and then provided to the external communication module 924. Thus, the adders 942 may optionally be used, and in some embodiments may be bypassed as shown by the arrows.

A time gain control (TGC) circuit 922 and TGC RAM 920 may also be included in the ultrasound transducer probe 900 to provide TGC functionality. The TGC RAM 920 may store data of a TGC curve to be implemented by the TGC circuit 922. The TGC circuit 922 may be coupled to the receive circuitry modules 906 to adjust them suitably to provide TGC functionality. For instance, a global gain setting 944 may be provided to all the columns. The slave line 946 may be the slave of the SPU 912. The SPU may send the time gain control to the TGC circuit 922 which may then send out the TGC information via the global gain setting 944.

The TGC circuit 922 and the TGC RAM 920 may exchange data 946 and addresses 948 of the appropriate ultrasound elements 901 may be provided by the TGC circuit 922 to the TGC RAM 920. The TGC RAM 920 may also receive data from the external communication module 924 via line 950.

The transmit circuitry modules and receive circuitry modules of FIGS. 8 and 9 may take any suitable form and may include programmable circuitry in some embodiments. Non-limiting examples of transmit and receive circuitry modules are illustrated in FIG. 10.

Figure 10:
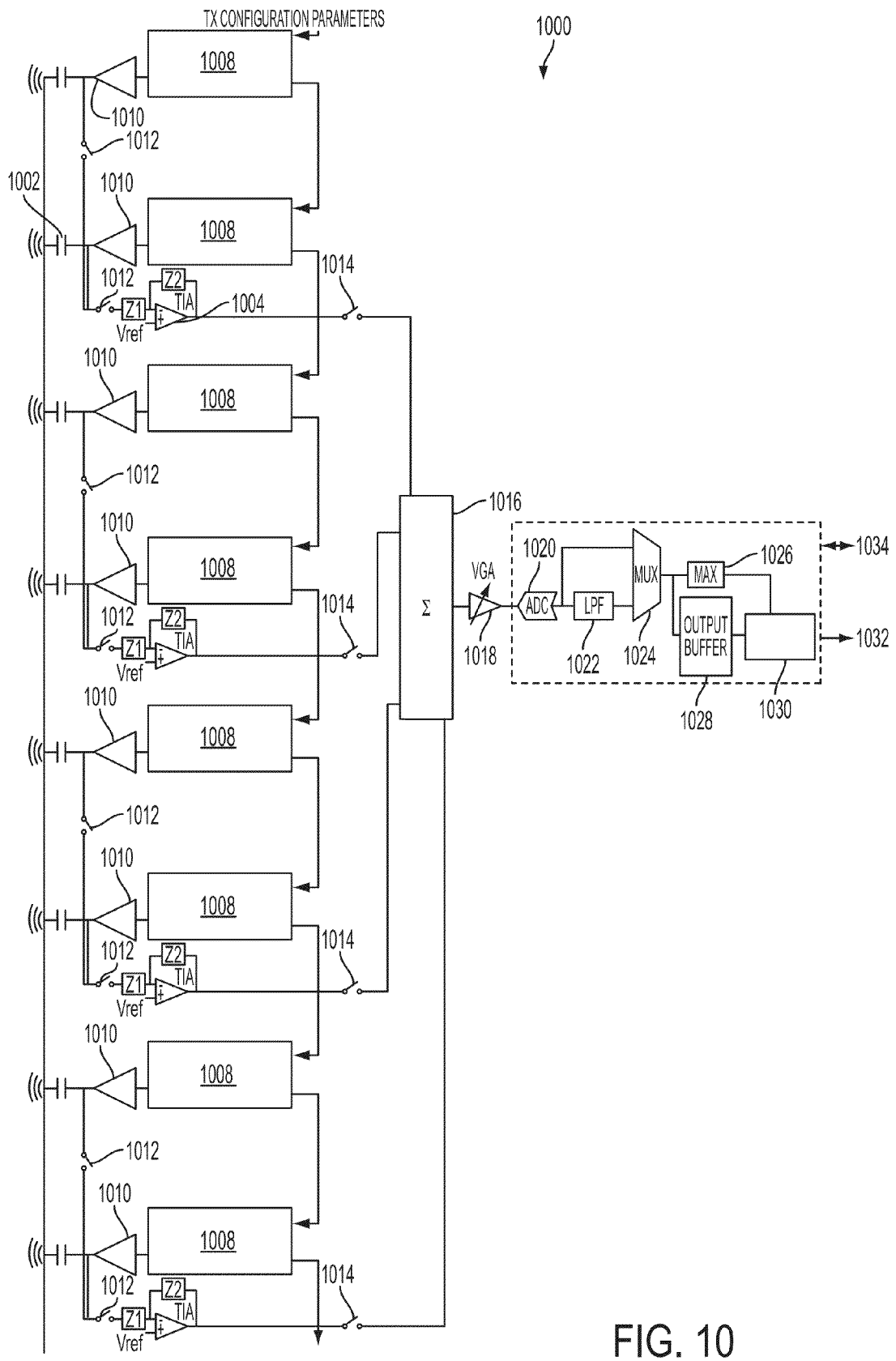
FIG. 10 illustrates the interconnection of transmit excitation modules and a receive module for a plurality of ultrasound elements arranged in a column, according to a non-limiting embodiment of the present application.

FIG. 10 illustrates a single half column of an ultrasound transducer probe which may represent an embodiment of a half column of the ultrasound transducer probe 900. As shown, the half column 1000 includes a plurality (eight in this example) of ultrasound elements 1002. Each ultrasound element 1002 is coupled to a respective transmit excitation module including a waveform generator 1008 and a pulser 1010. The ultrasound elements 1002 are switchably coupled to a single receive circuitry module via switches 1014. In some embodiments, each ultrasound element may be connected to its own receive circuitry module, rather than having multiple ultrasound elements share a receive circuitry module.

The waveform generator 1008 may be a programmable waveform generator. In some embodiments, the waveform generator 1008 may be configured to produce various kinds of waveforms, including continuous waves, impulses, coded excitations, and chirp waveforms. A non-limiting example of a suitable waveform generator is described further below in connection with FIG. 11. As illustrated, the waveform generators 1008 may be coupled in a daisy-chain configuration, such that the transmit parameters (labeled as "TX Configuration Parameters") controlling operation of the waveform generators may be passed from one waveform generator to the next.

The pulser 1010 may be any suitable type of pulser, non-limiting examples of which are described further below, for example in connection with FIG. 12. In some embodiments, the pulser 1010 may be a tri-level pulser. The pulser may be bipolar, configured to drive positive and negative voltages, although unipolar pulsers may be used in some embodiments.

In the example of FIG. 10, a transimpedance amplifier (TIA) 1004 may be coupled to two ultrasound elements 1002 via transmit/receive switches 1012, which may control whether the half-column is operating in a transmit mode or a receive mode. The TIA may be the implemented form of an LNA in some embodiments because current may be the quantity of interest in the receive circuitry module. For example, in those embodiments in which the ultrasound element 1002 is made up of one or more CMUTs or CUTs, the velocity of the CMUT or CUT membrane may be proportional to the magnitude of current provided from the CMUT or CUT.

As illustrated in FIG. 10, the ultrasound elements 1002 may be coupled to the receive circuitry module by switches 1014. In the illustrated embodiment, four switches 1014 are provided for the eight ultrasound elements 1002. However, in some embodiments each ultrasound element 1002 may be coupled via its own switch to the receive circuitry module. Any suitable number of ultrasound elements 1002 may share a switch 1014. In this manner, the ultrasound elements 1002 may be configured into various sub-arrays.

When the ultrasound transducer probe operates in a transmit mode, the switches 1014 may all be opened, disconnecting the ultrasound elements 1002 from the receive circuitry module. When the ultrasound elements 1002 operate in a receive mode, the switches 1014 may be closed in any suitable sequence to connect the ultrasound elements 1002 to the receive circuitry module and thus read a signal out from one or more of the ultrasound elements 1002. It should be appreciated that switches 1014 provide a degree of configurability in determining whether the outputs from the ultrasound elements 1002 are provided by two ultrasound elements at a time, eight ultrasound elements at a time, or some number in between.

The switches 1014 couple the ultrasound elements 1002 to a multiplexing or summing circuit 1016. The multiplexing or summing circuit 1016 may couple an ultrasound element 1002 to a variable gain amplifier (VGA) 1018. In some embodiments, the VGA 1018 may include a filter, such as a second order low-pass filter. The output of the VGA 1018 may be coupled to an analog-to-digital converter (ADC) 1020 to digitize the output signals of the ultrasound elements 1002.

The TIAs 1004 and VGA 1018 may be configured in combination to provide target noise characteristics in view of the configurable nature of the illustrated circuit. That is, use of the VGA 1018 in combination with the TIAs 1004 may account for the fact that the switches 1014 may be operated to alter whether a single ultrasound element 1002 is providing its output at any given time or whether all eight ultrasound elements 1002 are providing their outputs simultaneously. The illustrated configuration of TIAs 1004 and VGA 1018 may also reduce the amount of chip area compared to if a single TIA or VGA was provided for each ultrasound element. In some embodiments, the TIAs 1004 (or, more generally, the LNAs) and/or VGA 1018 may be powered down when not used (e.g., during transmit modes). By powering down the TIAs 1004 and/or VGAs 1018 during idle and/or non-transmit modes, overall power consumption of the device may be reduced.

The VGA 1018 may function to adjust the gain of the signals received from the ultrasound elements 1002 to provide a substantially constant power level over the duration of the receive time window. For a given excitation event, the signals received by the ultrasound elements 1002 may generally decrease in magnitude as time progresses. If the magnitude becomes too low, the signal may fall below the threshold of the ADC 1020. By providing a time varying gain, the VGA 1018 may prevent such behavior, thus allowing for ultrasound analysis of a wider region within a subject. The time varying gain profile implemented by the VGA 1018 may be provided by, for example, the TGC circuit 922 of FIG. 9.

Additional circuitry of the receive circuitry module 1006 may include a low pass filter (LPF) 1022, a multiplexer 1024, a maximum value detection circuit 1026, an output buffer 1028 and a re-quantizer 1030. Signals received by the receive circuitry module from one or more of the ultrasound elements 1002 may be digitized by the ADC 1020, then filtered by the LPF 1022, and re-quantized by the re-quantizer 1030. The LPF 1022 may be any suitable low pass filter for filtering a desired frequency range. In some embodiments, the LPF 1022 may be a decimating filter, and in some embodiments a ½ band decimating filter. Other types of low pass filters may alternatively be used.

The re-quantizer 1030 may reduce the amount of data to be sent externally from the ultrasound transducer probe. Any suitable re-quantizer for performing this function may be used. The re-quantizer may operate to discard data bits not of interest or not needed to produce ultrasound data of a desired quality. As a non-limiting example of the operation, the re-quantizer 1030 may determine a maximum data value from a set of received data. A count of the number of shifts (e.g., to the left) within the data set to get to a position at which the two most significant bits differ from those of the maximum data value may then be made. This determined count may be provided to an end user of the ultrasound transducer probe. Then, as the ultrasound data is sent externally from the ultrasound transducer probe, all the data values may be shifted (e.g., to the left) by the determined count and the upper N rounded bits may be sent. N represents an integer and may be set at a desired level (e.g., the upper five bits, upper seven bits, upper eight bits, or other suitable value) to achieve sufficient data reduction. It should be appreciated that this process of re-quantization is a lossy process, but that by suitable selection of N the ultrasound data sent externally from the ultrasound transducer probe may be of sufficiently high quality to enable desired applications (e.g., imaging applications) of the ultrasound transducer probe while providing data reduction.

The output 1032 of the receive circuitry module may represent the data from the ultrasound elements 1002 and may be provided, for example, to the external communication module 924 of FIG. 9. A parallel bus interface 1034 may also be provided and may, for example, communicate with the TGC circuit 922 of the ultrasound transducer probe in the manner previously described in connection with FIG. 9.

The circuitry of FIG. 10 may sample the signals received by the ultrasound element 1002 at any suitable frequency. According to an embodiment, quadrature sampling may be used, which may reduce the number of samples taken and allow more efficient operation.

The receive circuitry positioned downstream of the ADC 1020 may also be configured to perform cancellation of signals. For example, two pulse or three pulse cancellation techniques may be implemented. Other modes implementing techniques such as addition or averaging of signals, subtraction of signals, or bit shifting techniques may be used to facilitate cancellation of signals. Such cancellation may, for example, facilitate measurement of non-linear responses and scatterer velocities.

Figure 11:
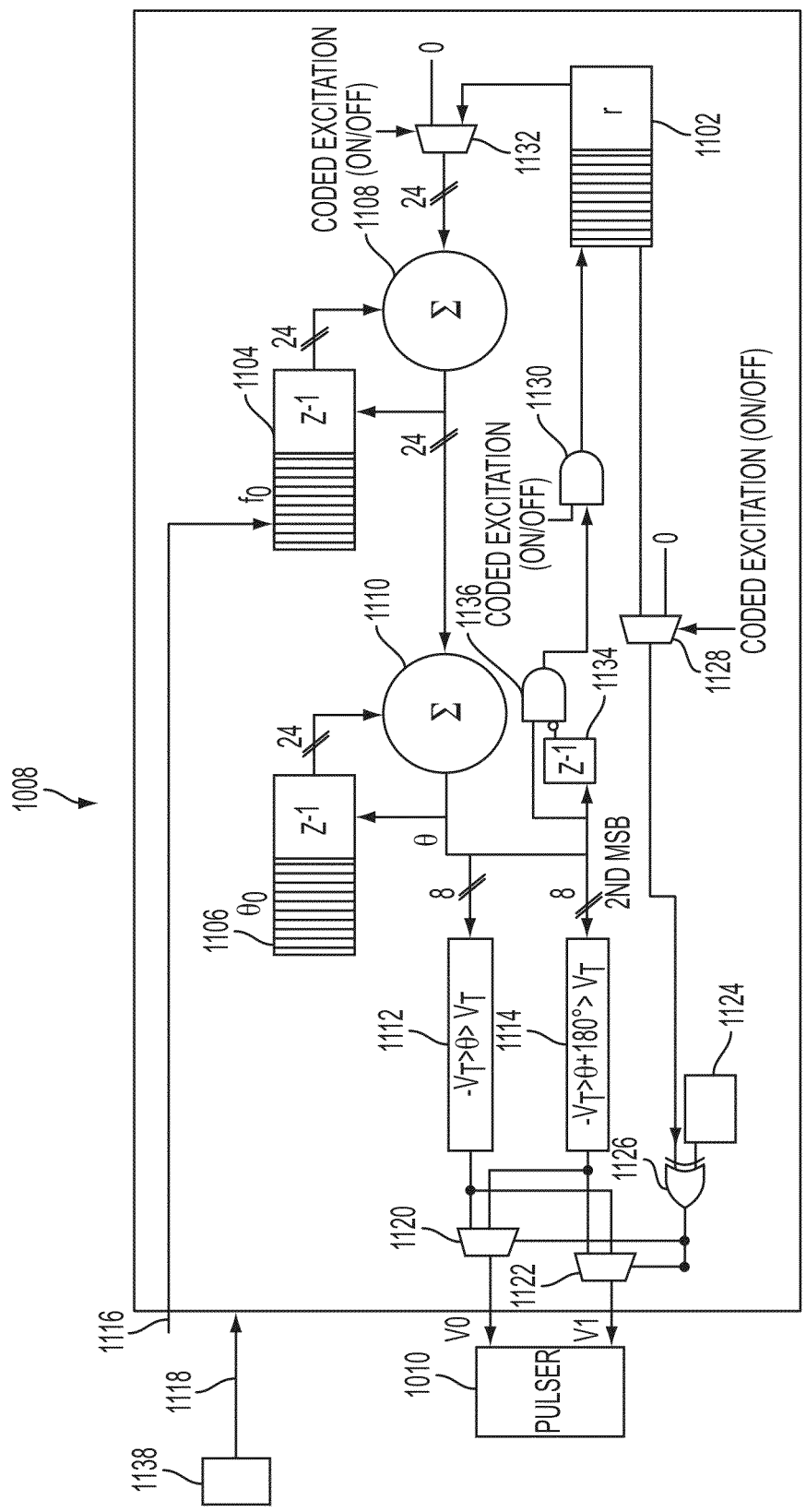
FIG. 11 illustrates an example of a programmable waveform generator of a type which may be used in an ultrasound transducer probe of the types described herein, according to a non-limiting embodiment of the present application.

FIG. 11 illustrates a non-limiting detailed example of the waveform generator 1008 which, as described, may be programmable in some embodiments and which may be configured to produce different kinds of waveforms, including impulses, continuous waves, chirp waveforms, and coded excitations. As shown, the waveform generator 1008 may include registers 1102, 1104, and 1106. Register 1102 may store one or more values relating to a desired rate of change of the frequency of the generated waveform, i.e., the chirp rate, r. Register 1104 may store one or more values relating to an initial frequency of the waveform, $f_0$. Register 1106 may store one or more values relating to an initial phase of the waveform, $\theta_0$. Thus, the waveform generator 1008 may be programmable, allowing for three degrees of freedom by allowing the registers 1102, 1104, and 1106 to be set. Additional degrees of freedom may be provided as described below. Summation circuits 1108 and 1110 may be provided to suitably sum the values from the registers 1102, 1104, and 1106 as shown. The combination of the summation block 1108 and register 1104 forms an accumulator, as does the combination of the summation block 1110 and register 1106. The values from registers 1104 and 1106 may be loaded into the respective summation blocks prior to operation. In some embodiments, the accumulators may also be configured as decrementers (e.g., to provide a chirp up and a chirp down). In some embodiments, the accumulated values may be reset with a reset operation, such as a bit shift or modulo operation.

The waveform generator 1008 further comprises comparison circuits 1112 and 1114. The comparison circuit 1112 compares the phase of the generated waveform to $\pm V_T$. Comparison circuit 1114 compares the inverse phase of the generated waveform ($\theta + 180°$) to $\pm V_T$. The outputs of comparison circuits 1112 and 1114 are provided to multiplexers 1120 and 1122, which provide output signals V0 and V1 to the pulser 1010. The output signals V0 and V1 may be binary signals. $V_T$ represents the value the sine wave, as represented by the phase, needs to achieve before triggering the pulser 1010 to transition. $V_T$ may be tunable, thus representing an additional degree of freedom.

The waveform generator 1008 includes multiple components providing the ability to generate coded excitations (e.g., binary coded excitations). As shown, a multiplexer 1128, multiplexer 1132 and AND gate 1130 all receive an indication of whether a coded excitation is to be generated. The multiplexers 1128 and 1132 receive the indication as a control signal and each have one input configured to receive a zero. The AND gate 1130 receives the indication as an input.

A flip bit circuit is also provided, including a flip bit register 1124 configured to store a flip bit that flips the output signals V0 and V1, which is provided to an input of a XOR gate 1126 that also receives the output of the multiplexer 1128. Thus, the flip bit, which may be a static bit, may provide for inversion of the waveform generator waveform. AND gate 1136 is also provided and has an inverting input as shown. The output of summation circuit 1110 is provided to one input of the AND gate 1136 and is also delayed by delay element 1134 and then provided to the inverting input of the AND gate 1136, the output of which is provided as an input to the AND gate 1130.

The illustrated configuration allows for the turning on and off of various components depending on whether coded excitation is to be performed. In operation, the registers 1102, 1104, and 1106 are loaded. The waveform generator 1008 receives a clock signal 1116, for example from a clock generation circuit (not shown in FIG. 11), and a transmit enable signal 1118, for example from a master timer (not shown in FIG. 11). The transmit enable signal 1118 may be a delayed transmit signal produced by a delay block 1138. The delay block 1138 may provide a coarse and/or fine delay, and thus may provide an additional degree of freedom. In some embodiments, the start time of a waveform and the waveform duration may be set, providing two degrees of freedom.

If coded excitation is to be performed, values from register 1102 may be fed through the multiplexer 1128 to the XOR gate 1126. Thus, the register 1102 may serve a dual purpose in providing values to set a chirp rate when a chirp is generated or to provide values to generate a binary coded excitation. When a coded excitation is to be generated, the output of multiplexer 1132 is the static value zero. The illustrated indication of the $2^{nd}$ most significant bit (MSB) provided to the input of AND gate 1136 indicates the frequency of coding to be performed. Any number of significant bits may be provided from the output of summation circuit 1110 to provide a desired frequency of coding, as the $2^{nd}$ MSB is an example.

Whether or not coded excitation is performed, the comparison circuits 1112 and 1114 may perform the described comparisons to generate the values of V0 and V1 which may then be provided to the pulser 1010.

Thus, it should be appreciated that the waveform generator 1008 is a programmable waveform generator which may be programmed to produce different kinds of waveforms by setting the registers 1102, 1104, and 1106 and controlling whether coded excitation is to be provided or not. In this manner, flexibility and versatility of the ultrasound transducer probe may be provided. High end imaging modalities may be implemented, taking advantage of the ability to generate continuous wave excitations, impulse excitations, coded excitations, and chirp excitations. Moreover, different kinds of waveforms may be generated for different ultrasound elements of an ultrasound transducer probe, or at different times of operation. In some embodiments, the same kind of waveform may be generated by two different waveform generators of the ultrasound transducer probe, but with different parameterizations, for example different amplitudes and/or delays (or any other characteristic of a waveform).

The registers of waveform generator 1008 may have any suitable sizes, as the exact sizes are not limiting of the various aspects of the present application. In some embodiments, the register sizes may be between approximately eight and approximately 32 bits, although other sizes may alternatively be implemented.

In some embodiments, Hadamard coding may be implemented in connection with waveform generation. Such coding may be used, for example, to facilitate apodization. The ultrasound transducer probe may include circuitry to implement the Hadamard coding.

Figure 12:
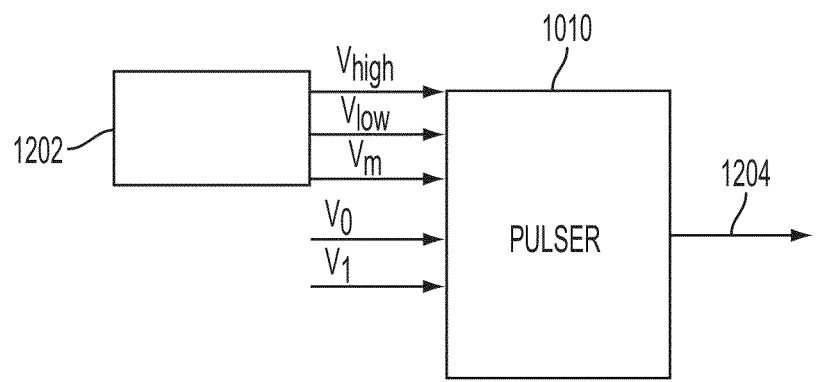
FIG. 12 illustrates a pulser of a type which may be used in an ultrasound transducer probe of the types described herein, according to a non-limiting embodiment of the present application.

FIG. 12 illustrates a non-limiting example of the pulser 1010. As previously described, in some embodiments the pulser 1010 may be a tri-level pulser. The pulser 1010 may receive five input signals, including Vhigh, Vlow, Vm, V0, and V1. As previously described, V0 and V1 may be provided by the waveform generator (e.g., waveform generator 1008), and may be binary signals. Vhigh, Vlow, and Vm may be provided by a voltage source 1202, for example by the voltage/current circuitry module 918. The pulser may provide an output signal 1204, which may be a bipolar signal (i.e., having positive and negative voltages) or a unipolar signal in some embodiments. FIG. 12 includes a table illustrating the output value of output signal 1204 as a function of the input values V0 and V1. The indicated output value "High Z" when V0 and V1 both have a value of 1 refers to disconnecting the pulser 1010 from the ultrasound elements (e.g., open-circuiting the connection between the pulser and the ultrasound element).

The pulser 1010 may provide any suitable output voltages for a particular application. In some embodiments, the pulser may output voltages between approximately 5 V and approximately 20 V (e.g., 7.5 V), between approximately 20 V and approximately 120 V, any range or value within such ranges, or any other voltage.

Figure 13:
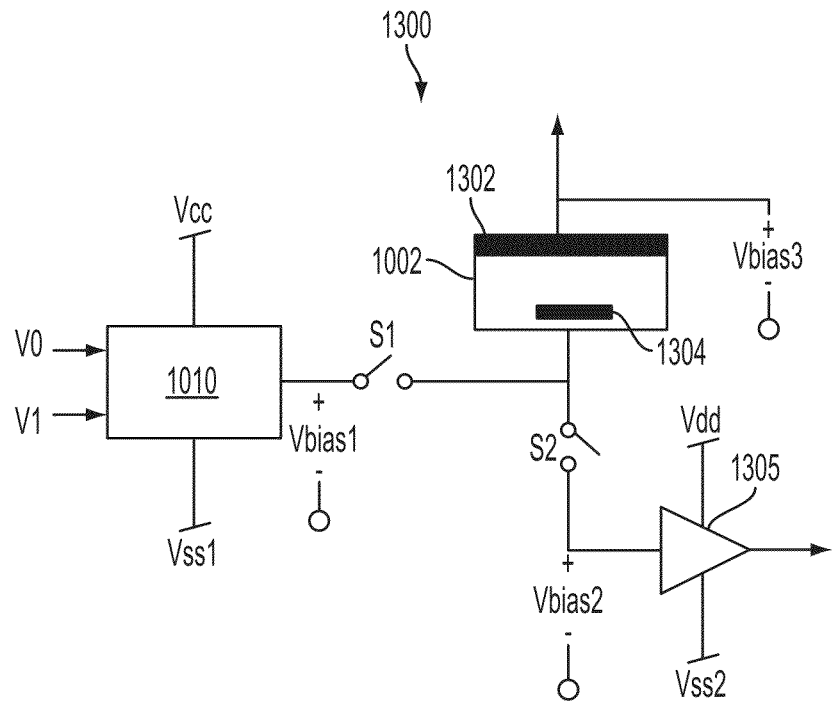
FIG. 13 illustrates an example of an ultrasound element coupled to a pulser and to an amplifier according to a non-limiting embodiment of the present application.

FIG. 13 illustrates a more detailed example of the configuration of a subcircuit including a pulser, an ultrasound element, and an amplifier (e.g., a LNA, such as a TIA) of an ultrasound transducer probe according to an embodiment of the present application, as may be used in the configuration of FIG. 10. The subcircuit 1300 includes the pulser 1010, ultrasound element 1002, and amplifier 1305. The pulser 1010 receives inputs V0 and V1 as previously described, as well as reference voltages Vcc and Vss1. The output of the pulser 1010 may be biased by a signal Vbias1.

The ultrasound element 1002 includes a first electrode 1302 facing a target subject (e.g., a medical patient). The first electrode 1302 may be configured to receive a voltage Vbias3. The ultrasound element 1002 further includes a second electrode 1304 that is distally positioned from the target subject. The second electrode 1304 may be coupled to the output of the pulser 1010 by the switch S1. The second electrode 1304 may also be coupled to the input of the amplifier 1305 by a switch S2. The input of the amplifier 1305 may also be biased by a bias signal Vbias2. The amplifier 1305 may receive reference voltages Vdd and Vss2.

The voltages illustrated in FIG. 13 may take various values depending on the manner of operation. According to some embodiments, Vbias1 and Vbias2 may be substantially equal, and have a value between approximately 30 V and approximately 90 V (e.g., 75 V). Vcc may be equal to Vbias1 plus some positive offset (e.g., Vcc=Vbias1+18 V). Vss1 may be equal to Vbias1 minus the offset (e.g., Vss=Vbias1−18 V). Vdd may be equal to Vbias1 plus a smaller positive offset than used for Vcc (e.g., Vdd=Vbias1+5 V), while Vss2 may be equal to Vbias1 minus this smaller offset (e.g., Vss2=Vbias1−5 V). Vbias3 may be grounded in this configuration, which may minimize the risk of electrically shocking the subject. Voltages other than those described above may be implemented.

According to some embodiments, Vbias1 and Vbias2 may be electrically grounded (e.g., set to 0 V). Vbias3 may bias the first electrode 1302, for example at a value between −30 V and −90 V (e.g., −75 V). Vcc and Vss1 may be set to approximately 18 V and −18 V, respectively, and Vdd and Vss2 may be set to approximately 5 V and −5 V, respectively. When Vbias3 is not grounded, the electrode 1402 may be covered with an insulating material to reduce the risk of shock. Voltages other than those listed may be implemented.

The generation of clock signals within an ultrasound transducer probe of the types described herein may be performed in a manner which facilitates tiling and coordinated operation of multiple instances of the ultrasound transducer probe. When ultrasound transducer probes are tiled and interconnected for coordinated operation, one of the ultrasound transducer probes may serve as a controller or master and the other probe(s) may serve as controlled probes. For example, considering FIG. 2C as an example, the ultrasound transducer probe 200 on the left side of the figure may serve as a master and the ultrasound transducer probe 200 on the right side of the figure may be controlled, at least with respect to clocking.

Figure 14:
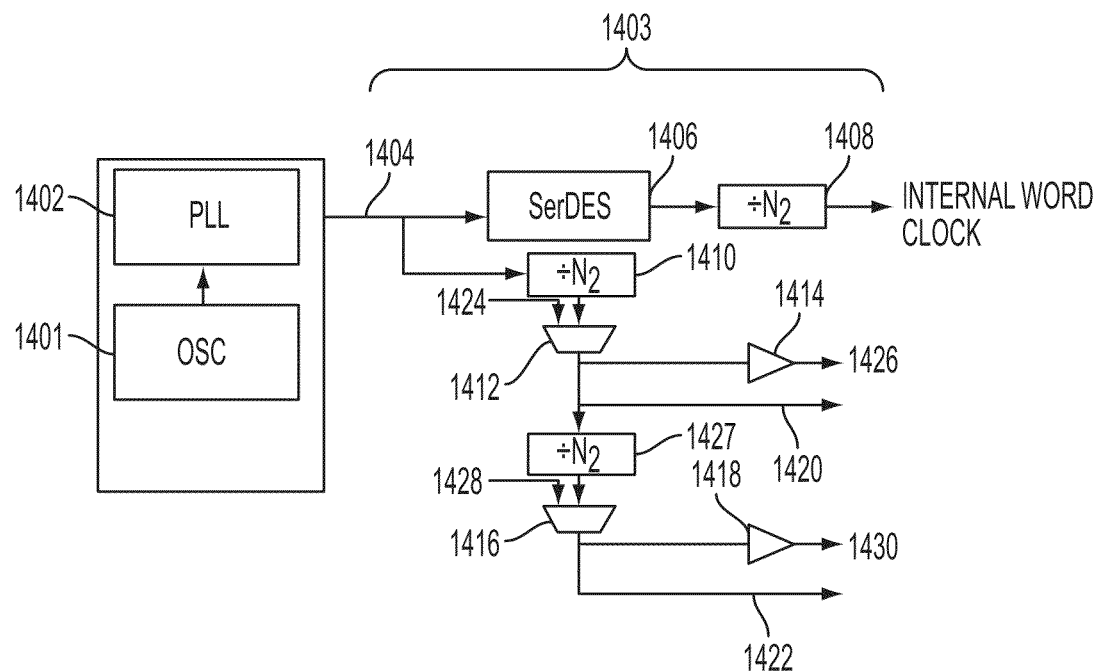
FIG. 14 illustrates a clock circuit of a type which may be used in an ultrasound transducer probe according to a non-limiting embodiment of the present application.

FIG. 14 illustrates an example of a manner of generating clock signals within an ultrasound transducer probe, and is generic to whether the probe is operating as a master probe or a controlled probe. As shown, the clock generation circuit 1403 may receive an external clock signal 1404 produced by an oscillator 1401 and phase-locked loop (PLL) 1402 located external to the ultrasound transducer probe. The clock signal 1404 may be a high frequency clock signal (e.g., between approximately 1.5 GHz and approximately 6 GHz, approximately 2.5 GHz, approximately 5 GHz or any other suitable frequency).

In the illustrated embodiment, the clock generation circuit 1403 may divide the clock signal 1404 by a desired amount and distribute the divided signal(s). For example, as shown, the clock generation circuit 1403 may include a SerDES module 1406, the output of which may be provided to a first division circuit 1408. The output of division circuit 1408 may represent a word clock in some embodiments, such as an internal USB word clock to be used internally on the ultrasound transducer probe. The clock signal 1404 may also be provided to a second division circuit 1410, the output of which may be provided to a multiplexer 1412. The multiplexer 1412 also receives an external digital clock signal 1424, which may represent a digital clock signal provided by another ultrasound transducer probe, for example when the illustrated probe is operating as a controlled probe.

The output of multiplexer 1412 may be used to produce both an internal digital clock signal 1420 to be used within the ultrasound probe and an external digital clock signal 1426 representing the output of buffer 1414. The external digital clock signal 1426 may be provided to another controlled ultrasound transducer probe as its external digital clock signal 1424.

The output of multiplexer 1412 may also be provided to a third division circuit 1427, the output of which may be provided to a multiplexer 1416. The multiplexer 1416 also receives an external ADC clock signal 1428 which may be provided by another ultrasound transducer probe when the illustrated ultrasound transducer probe is part of a tiled set of ultrasound transducer probes and is operated as a controlled probe within the set.

The output of multiplexer 1416 may serve as an internal ADC clock 1422 for clocking ADCs of the ultrasound transducer probe. The output of the multiplexer 1416 may also be sent to a buffer 1418 to produce an external ADC clock signal 1430 to be sent to other controlled ultrasound transducer probes.

Thus, it should be appreciated that the configuration of FIG. 14 allows for clocking signals to be sent from one ultrasound transducer probe to another ultrasound transducer probe in a manner that allows for coordinated operation. An alternative manner for providing such coordinate operation is to have a respective PLL on each ultrasound transducer probe. A lower frequency clock than clock 1404 may be provided to the PLLs of the ultrasound transducer probes and each transducer probe may derive its own clock signals from the distributed lower frequency clock.

Figure 15:
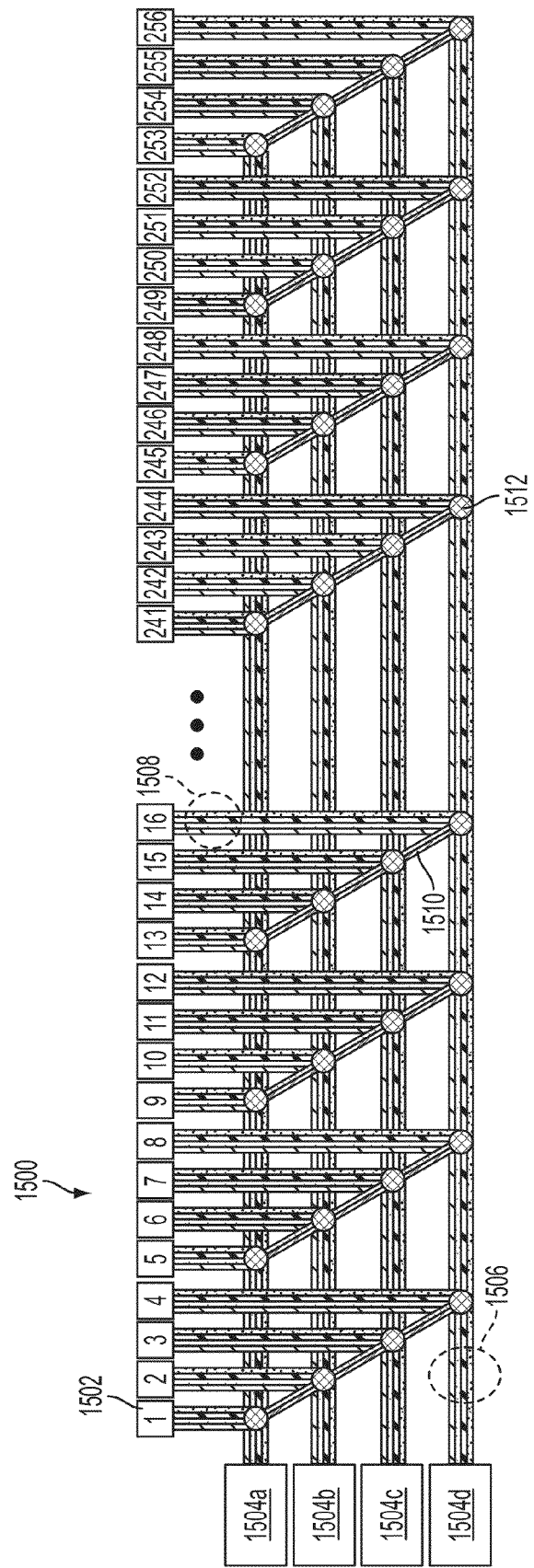
FIG. 15 illustrates a mesh which may be used to offload data from an ultrasound transducer probe according to a non-limiting embodiment of the present application.

Configurability of ultrasound transducer probes according to aspects of the present application may also be provided through configuration of the circuitry for offloading data from the ultrasound transducer probe to an external device. FIG. 15 illustrates a non-limiting example utilizing a mesh configuration.

The mesh 1500 includes receiver channels 1502 and external links 1504a-1504d. The illustrated embodiment includes 256 receiver channels, which may be utilized with an ultrasound transducer probe including 16×128 ultrasound elements with the columns of ultrasound elements being configured such that there are two receiver channels per column, for example as described in connection with FIG. 9. The external links 1504a-1504d may correspond to the previously described interfaces (e.g., interfaces 208a and 208b). In the illustrated example, the external links 1504b-1504d may represent higher speed links, and the external link 1504a may be used as either a higher speed link or a lower speed link (e.g., a USB link).

The mesh 1500 is configurable to shift data horizontally and/or diagonally to send the data external to the ultrasound transducer probe via one or more of the external links 1504a-1504d. As shown, the receiver channels 1502 are connected to nodes 1512 by signal paths 1508, which may include any number of signal lines (e.g., four as a non-limiting example). Data can be shifted horizontally from a node 1512 to an external link 1504a-1504d by signal paths 1506 and/or shifted diagonally to another node 1512 by signal paths 1510. The signal paths 1506 and 1510 may include any suitable number of lines. In some embodiments, the signal paths 1506 include four lines and the signal paths 1510 include two lines. Further detail is illustrated in FIG. 16.

Figure 16:
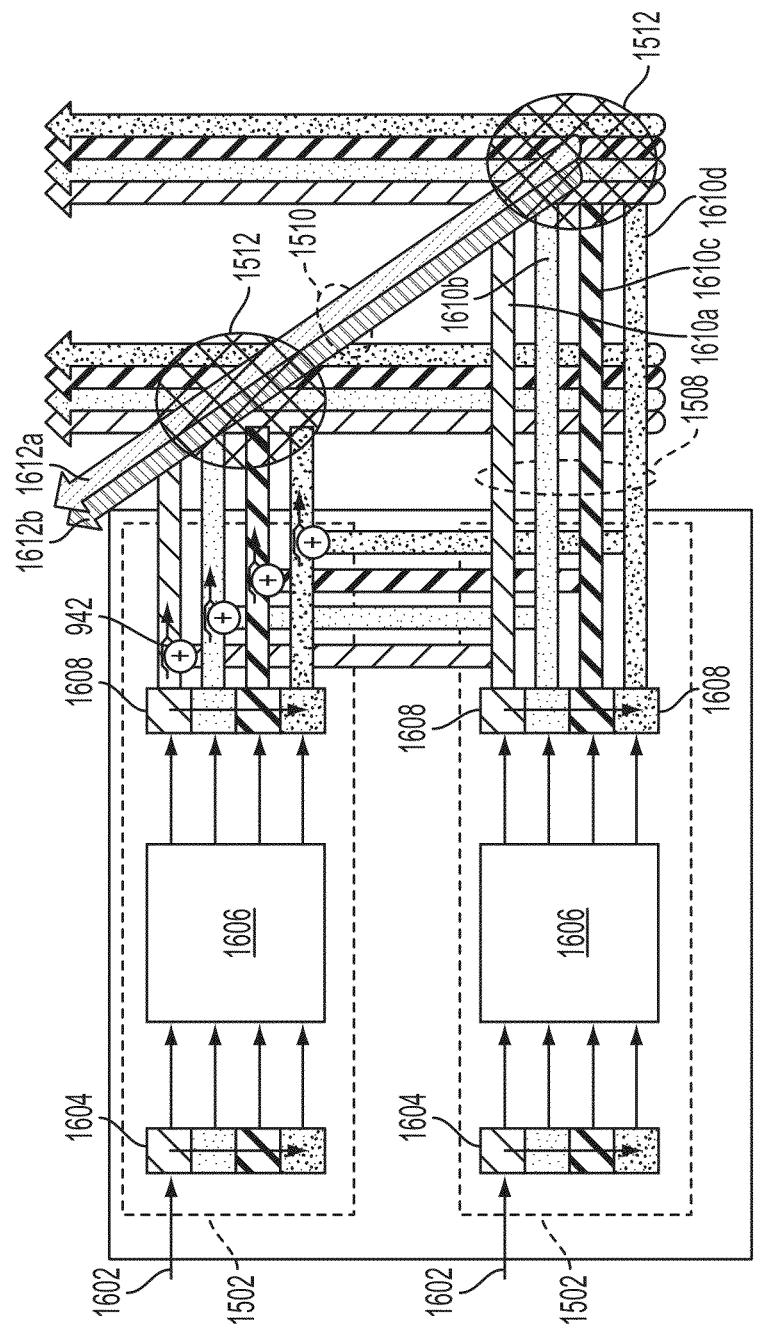
FIG. 16 is a detailed view of part of the mesh of FIG. 15, according to a non-limiting embodiment of the present application.

Two receiver channels 1502 are shown in FIG. 16 as being connected to respective nodes 1512. Data 1602 may be provided to shift registers 1604 which output parallel data to sampling RAM 1606, which in turn provides the data to shift registers 1608. The shift registers 1604 and 1608 may shift the data in the direction indicated by the arrows in FIG. 16. The signal paths 1508 may include four signal lines 1610a-1610d, and the data may be output from the shift registers 1608 to one or more of the signal lines 1610a-1610d to go to the nodes 1512. As previously described in connection with FIG. 9, in one mode of operation the data from two half-columns (e.g., the two illustrated receiver channels 1502 in FIG. 16) may be summed via adders 942. In such operation, the data may be provided to only one of the two nodes 1512 shown in FIG. 16.

The signal paths 1510 interconnecting the nodes 1512 to allow diagonal data shifting may include any suitable number of lines. In the embodiment illustrated, two lines 1612a and 1612b make up the signal paths 1510 but alternatives are possible.

Figure 17:
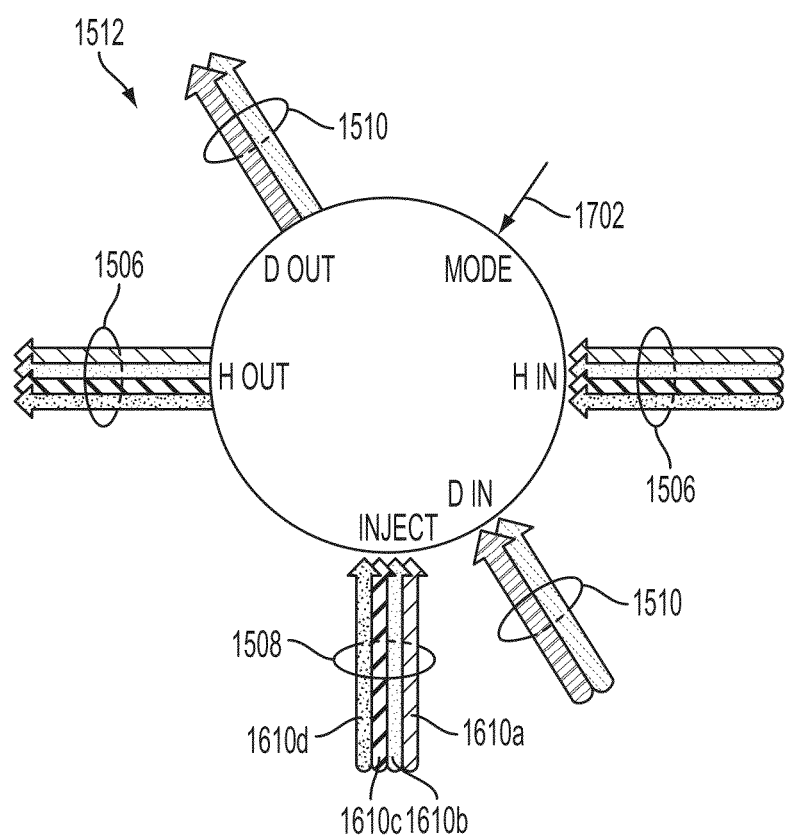
FIG. 17 illustrates a node configuration for the mesh of FIG. 15.

The nodes 1512, which may be shift registers in some embodiments, may be controllable to offer flexible operation depending on a desired operating mode. An example is shown in FIG. 17. The data from the receiver channels may be injected to the node at an input "INJECT." A mode control signal 1702 may be provided to a MODE input. The nodes 1512 may be controlled by, for example, the external communication module 924 of FIG. 9, which may provide the mode control signal 1702. The value of the mode control signal 1702 may dictate whether data is shifted horizontally through the node 1512 via the H IN and H OUT ports or whether the data is shifted diagonally via the D IN and D OUT ports. Whether horizontal and/or diagonal shifting is performed may depend on how many of the external links 1504a-1504d are to be used in operation.

For example, if all four external links 1504a-1504d are to be used (e.g., when the amount of data sent externally and frame rate are to be maximized in some embodiments), diagonal shifting and the associated data aggregation may be omitted. The data may be provided by the receiver channels to the respective nodes 1512 and shifted horizontally along lines 1506 to the respective external links 1504a-1504d.

By contrast, if only a single external link 1504a is to be utilized, whether it be a higher speed link or a lower speed link, data from the receiver channels coupled to nodes 1512 not on the horizontal signal path 1506 connected to external link 1504a may be shifted by the nodes 1512 diagonally to the horizontal signal path 1506 connected to external link 1504a. The data may then be shifted horizontally to the external link 1504a.

Figure 18A:
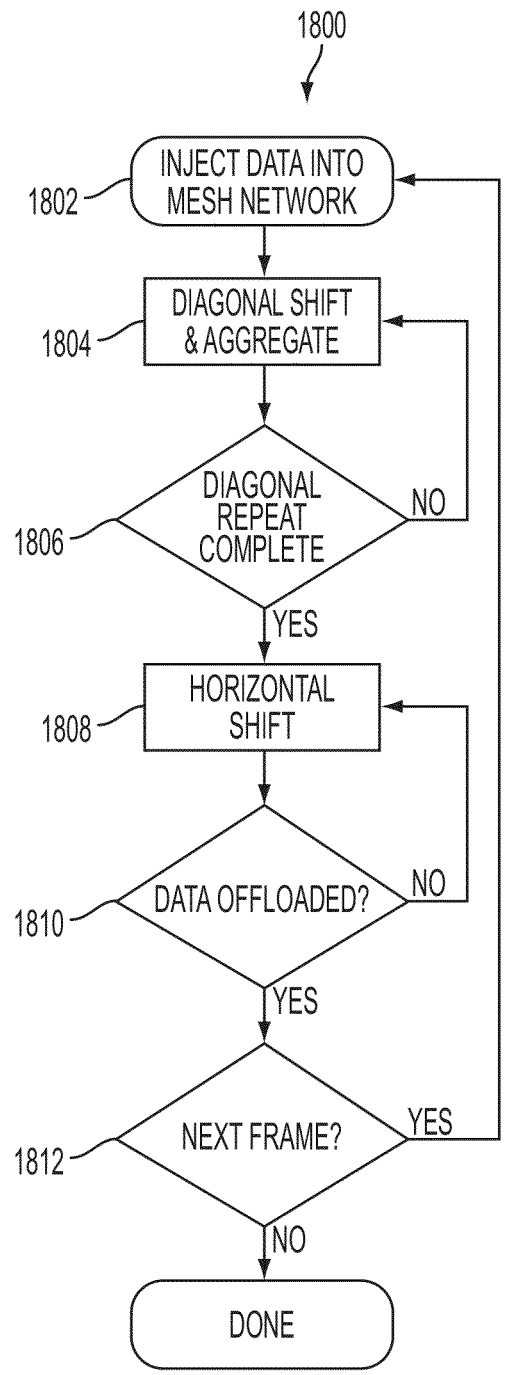
FIGS. 18A and 18B illustrate flowcharts of alternative manners of operating the mesh of FIG. 15, according to a non-limiting embodiment of the present application.
Figure 18B:
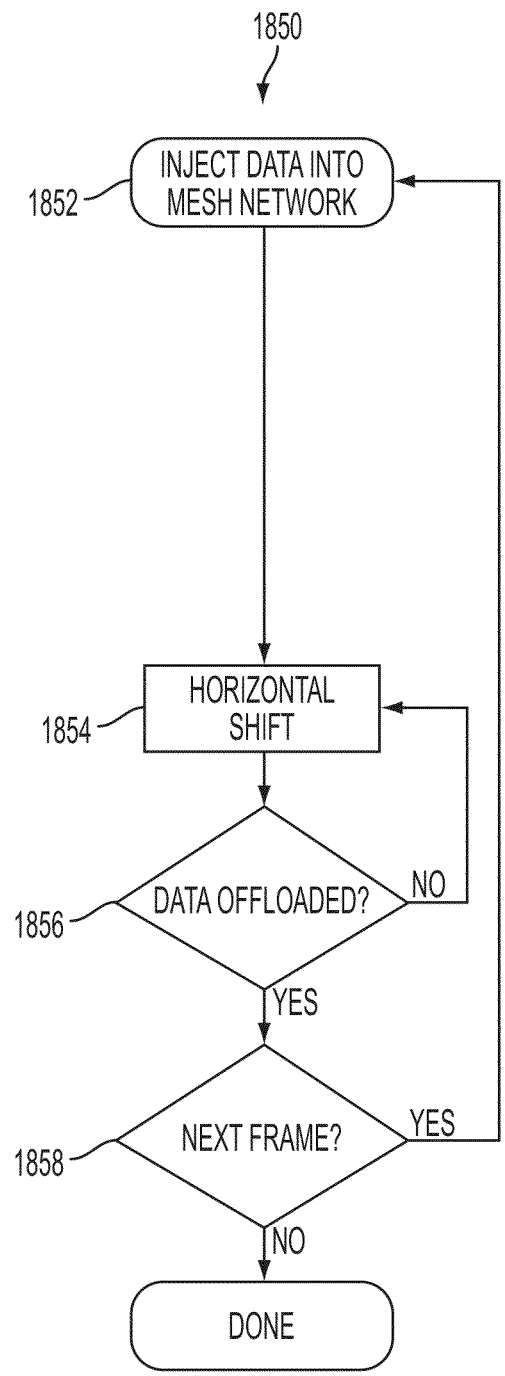

Two non-limiting examples of modes of operation of the mesh 1500 are shown in FIGS. 18A and 18B. The method 1800 of FIG. 18A illustrates a manner of operation using only one or two of the external links 1504a-1504d, rather than all four. At stage 1802, data is injected from the receiver channels 1502 into the mesh network. At stage 1804, the data is diagonally shifted and aggregated by the nodes 1512. At stage 1806 a determination is made whether the diagonal shifting is complete, or whether diagonal shifting needs to be repeated to shift the data to the horizontal signal paths connected to the external links being used. If the diagonal shifting is not complete, the method returns to stage 1804. If the diagonal shifting is complete, the method proceeds to stage 1808 to horizontally shift the data down the signal paths 1506 connected to the external links being utilized.

At stage 1810 a determination is made whether the data has been offloaded from the ultrasound transducer probe. If not, the method returns to stage 1808 for further horizontal shifting. If yes, the method moves to stage 1812 at which a determination is made whether there is a next frame to be processed. If yes, the method returns to stage 1802. If not, the method is completed.

The method 1850 of FIG. 18B may be implemented when all four external links 1504a-1504d are used. In such an embodiment, no diagonal shifting from the nodes 1512 may need to be performed. The method 1850 begins at stage 1852 by injecting data from the receiver channels into the mesh network. At stage 1854 the data is horizontally shifted by the nodes 1512. At stage 1856 a determination is made whether the data has been offloaded from the ultrasound transducer probe. If not, the method returns to stage 1854. If so, the method proceeds to stage 1858 to determine whether a next frame needs to be processed. If so, the method returns to stage 1852. If not, the method is completed.

Thus, the circuitry configuration for offloading data from an ultrasound transducer probe may also be configurable. The described configurability may facilitate the use of the ultrasound transducer probe in a variety of applications with different requirements such as data frame rates, amount of data, and speed of operation.

Thus, it should be appreciated from the foregoing discussion that several aspects of the architecture of an ultrasound transducer probe according to embodiments of the present application, including probe geometry and circuitry positioning and programmability, may facilitate use of an ultrasound transducer probe as either a standalone ultrasound transducer probe or as a repeatable unit to tile and interconnect with other such ultrasound transducer probes in a larger ultrasound device. Further features of the architecture may facilitate operation of the ultrasound transducer probe(s) for particular applications, as now described.

High Voltage Circuitry

Aspects of the present application provide for integration of ultrasonic transducers with circuitry on a single substrate, such as a CMOS substrate or chip. The ultrasonic transducers may be used for ultrasound imaging applications, HIFU, or both. In some embodiments, the ultrasonic transducers may operate at voltages higher than those conventionally used for CMOS integrated circuitry, e.g., higher than voltages typically supported by deep and ultra-deep submicron CMOS circuitry. For example, such ultrasonic transducers may operate at voltages between 20 V and 120 V, between 30 V and 80 V, between 40 V and 60 V, at any voltage within those ranges, or at any other suitable voltages, depending on the application. HIFU applications typically utilize higher voltages than ultrasound imaging applications. In some embodiments, submicron nodes may refer to nodes that are smaller than approximately 1 micron. In some embodiments, deep submicron nodes may refer to nodes that are smaller than approximately 0.3 microns. In some embodiments, ultra-deep submicron nodes may refer to nodes that are smaller than approximately 0.1 micron.

Thus, in those embodiments in which ultrasonic transducers are integrated with circuitry on a single substrate it may be desirable for such circuitry to be configured to sustain or withstand voltages in the ranges listed above, for example by supporting those higher-than-typical voltages at deep submicron nodes of the integrated circuitry. The circuitry may be configured in some embodiments to account for typical limits on the operating voltage of NMOS and PMOS devices in CMOS circuits arising due to: (1) gate oxide breakdown, and (2) source and drain (diffusion) breakdown.

To increase the diffusion breakdown limit to enable operation at higher voltages, suitable doping of the source and drain regions of any field effect transistor (FET) may be implemented. For example, lowering doping levels in the source and drain regions may increase the diffusion breakdown voltage. In some embodiments doping levels below $10^{17}$ dopants/$cm^3$ may be implemented.

With respect to gate oxide breakdown, which can arise as either gate-to-drain breakdown or gate-to-source breakdown, the maximum electric field applied across those points should be reduced. The standard gate-to-drain interface is a Lightly Doped Drain (LDD). The LDD may, for example, be doped to reduce the electric field but may be minimized in size to keep device length large enough to maintain gate control.

Aspects of the present application provide CMOS circuit designs suitable for use in ultrasound transducer probes of the types described herein and which exhibit breakdown voltages greater than those of conventional CMOS circuits. According to an aspect of the present application, mask logic operations and device layout are selected to provide suitable CMOS circuits for sustaining high voltages at deep submicron nodes.

CMOS circuitry may, for example, be turned into high-voltage CMOS circuitry by changing the diffusion scheme. For example, a mask-aligned source and drain using N-type well and P-type well regions may be employed. For NMOS implementations, the diffusion may be changed to an N-type well source/drain configuration with P-type substrate. For PMOS implementations, the diffusion may be changed to a P-type well source/drain configuration with N-type well and deep N-type well features. The sources and drains may be defined by Shallow Trench Isolation (STI). Alternatively, to sustain even larger voltages, the source and drain regions may be defined by gap space and thermal diffusion.

Examples of CMOS circuit layouts and associated structures that may be used to implement high-voltage CMOS circuits according to the various embodiments set forth herein are shown in FIGS. 19-28B. Specifically, FIGS. 19-22 illustrate examples of MOS transistor configurations which may sustain high voltages. FIGS. 23-28B illustrate examples of circuits which may utilize such transistors and be employed in ultrasound transducer probes of the types described herein.

Figure 19:
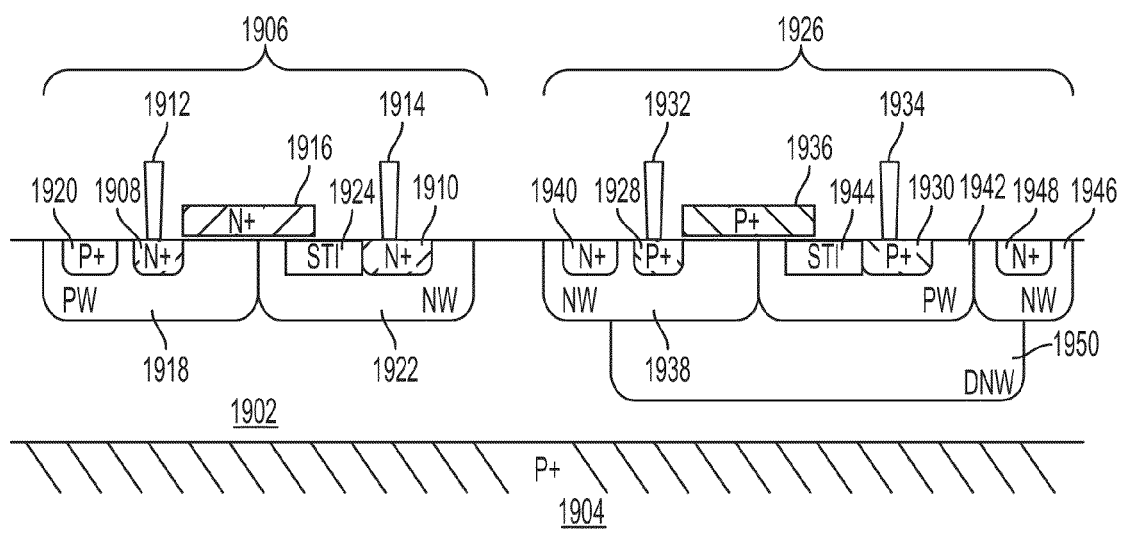
FIGS. 19-22 illustrate complementary metal oxide semiconductor (CMOS) transistor layouts for supporting high voltage operation, according to non-limiting embodiments of the present application.

FIG. 19 shows an example of a high voltage NMOS transistor and PMOS transistor layout that may be used in some embodiments to provide high voltages at deep submicron nodes. The illustrated example includes an epitaxial wafer formed of a P-type substrate 1902 with a P+ doped region 1904, on which the transistors may be formed. The substrate 1902 may have a low doping (e.g., on the order of $10^{15}$ dopants/$cm^3$) while the P+ doped region 1904 may have a higher doping, for example on the order of $10^{19}$ dopants/$cm^3$. Although an epitaxial wafer is shown, it should be appreciated that high voltage NMOS and PMOS transistors may be formed on bulk wafers according to aspects of the present application, and thus the illustration of an epitaxial wafer is not limiting. For example, the doped region 1904 may be excluded in some embodiments.

The NMOS transistor 1906 includes N+ source and drain regions 1908 and 1910, respectively. A source contact 1912 contacts the source region 1908 and a drain contact 1914 contacts the drain region 1910. An N+ gate 1916 is also included. The source region 1908 is formed in a P-type well (designated "PW") 1918 which has a P+ contact region 1920 serving as a body contact for the transistor. The drain region 1910 is formed in an N-type well (designated "NW") 1922. STI region 1924 is also included in the N-type well 1922.

Various features of the illustrated transistor 1906 may contribute to the ability to sustain high voltages. The configuration of the N-type well 1922 and the P-type substrate 1902 may contribute to the transistor 1906 having a large junction breakdown voltage. The N-type well 1922 and the P-type well 1918 may be lightly doped, and thus the region under the gate 1916 may be a LDD, thereby reducing the electric field between the gate 1916 and the source region 1908 and drain region 1910.

The PMOS transistor 1926 may also be configured to sustain high voltages. As shown, the PMOS transistor 1926 includes P+ source and drain regions 1928 and 1930, respectively. A source contact 1932 contacts the source region 1928 and a drain contact 1934 contacts the drain region 1930. A P+ doped gate 1936 is also included.

The source region 1928 is formed in an N-type well 1938 which includes an N+ contact region 1940 serving as a body contact for the transistor. The drain region 1930 is formed in a P-type well 1942, in which is also formed STI region 1944. An N-type well 1946 with a N+ contact region 1948 serving as a body contact for the transistor, as well as a deep N-type well (designated "DNW") 1950, are also included as shown. The deep N-type well 1950 provides isolation from the substrate 1902. A deep well may have a depth between approximately 1 micron and 8 microns.

The configuration of P-type well 1942 and N-type well 1938 contribute to the transistor 1926 being able to support high voltages without experiencing junction breakdown. The N-type well 1938 and the P-type well 1942 may be lightly doped, and thus the region under the gate 1936 may be a LDD, thereby reducing the electric field between the gate 1936 and the source region 1928 and drain region 1930.

Figure 20:
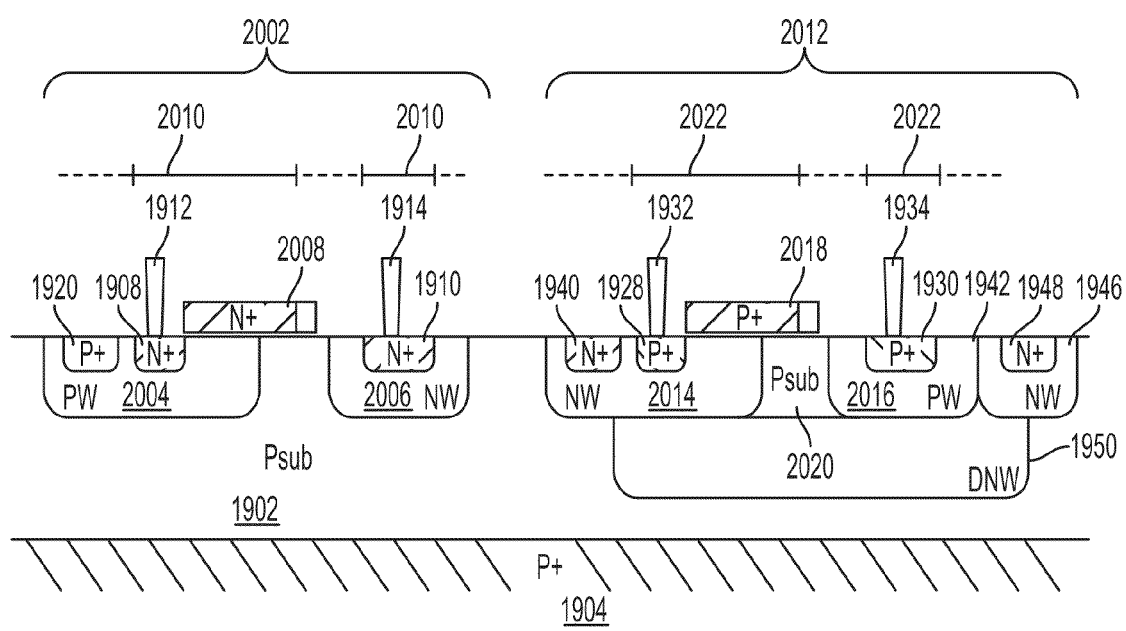

FIG. 20 shows an alternative configuration for an NMOS transistor and PMOS transistor, both of which can support high voltages. Compared to the configuration of NMOS transistor 1906, the NMOS transistor 2002 includes a P-type well 2004 and N-type well 2006 which do not touch. The P-type well 2004 may be a thermally diffused well, and likewise the N-type well 2006 may be a thermally diffused well.

The spacing indicated by reference number 2010 represents an example of a mask defining the N+ doping implant region for the transistor 2002. It should be appreciated that only part of the gate 2008 is doped N+.

The PMOS transistor 2012 differs from PMOS transistor 1926 in that the N-type well 2014 and P-type well 2016 do not touch each other as do the N-type well 1938 and P-type well 1942. Thus, a portion 2020 of the P-type substrate is disposed between the N-type well 2014 and the P-type well 2016. The N-type well 2014 may be thermally diffused. Likewise, the P-type well 2016 may be thermally diffused.

The spacing indicated by reference 2022 represents an example of a mask defining the P+ doping implant region of the transistor 2012. It should be appreciated that only part of the gate 2018 is doped P+.

Figure 21:
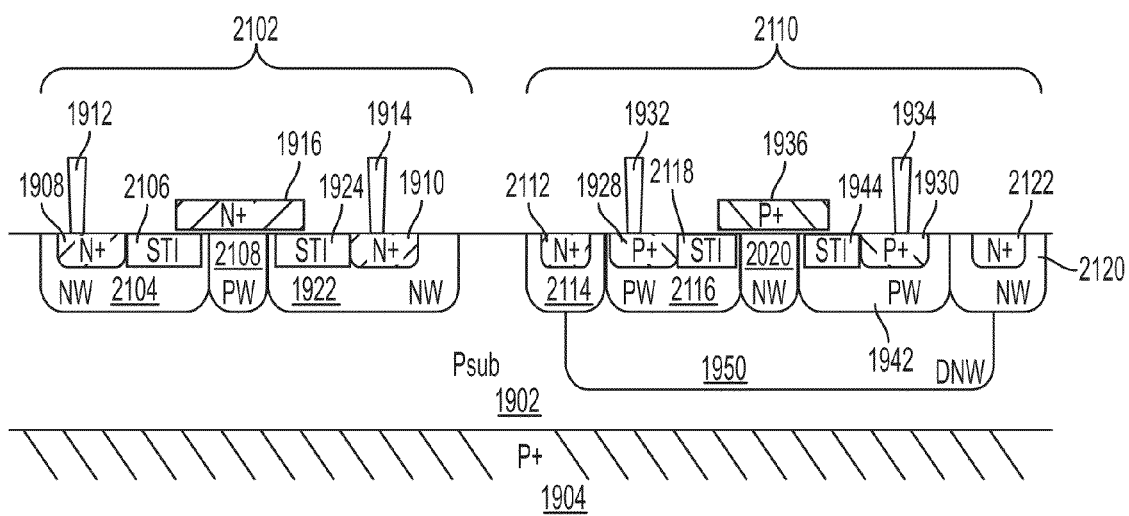

FIG. 21 shows an example of a high voltage NMOS and PMOS bidirectional or cascoding layout that may be used in some embodiments as part of an ultrasound transducer probe. The NMOS transistor 2102 includes an N-type well 2104 in which is formed STI region 2106 in addition to the source region 1908. The N-type well 2104 and N-type well 1922 do not touch, but rather are separated by P-type well 2108. The N-type well 2104 represents a well for the source region 1908 and also a source gate extension. In this embodiment, the N-type well 1922 functions as a well for the drain region 1910 and also as a gate extension. A body contact for the NMOS transistor 2102 is not explicitly shown but may be included and may be formed, for example, by a P-type well with a P+ diffusion region.

The PMOS transistor 2110 includes an N-type well 2114 with a N+ contact region 2112 adjacent a P-type well 2116 in which is formed the source region 1928 and STI region 2118. The N+ contact region 2112 serves as a body contact for the transistor. An N-type well 2020 separates P-type well 2116 from P-type well 1942. The P-type well 2116 represents a well for the source region 1928 and also a gate extension. P-type well 1942 operates as a well for the drain region 1930 and also as a gate extension.

The PMOS transistor 2110 also includes an N-type well 2120 and N+ contact region 2122 serving as a body contact for the transistor.

Figure 22:
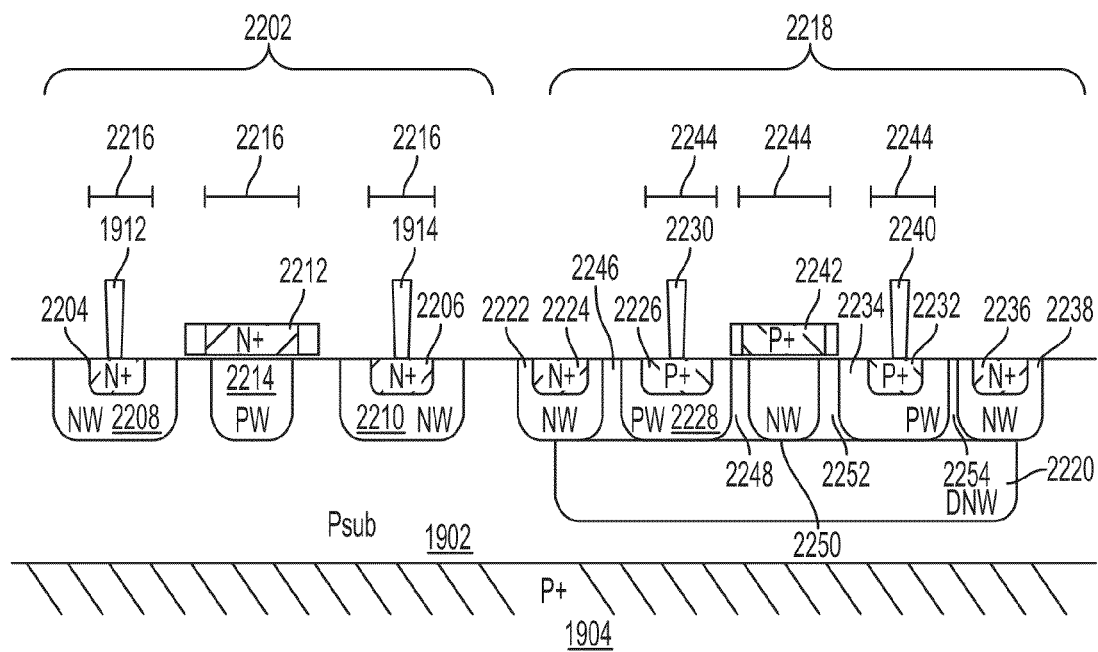

FIG. 22 shows an example of an alternative high voltage NMOS and PMOS bidirectional or cascoding layout that may be used in some embodiments, and which may sustain higher voltages than those applicable to the layout of FIG. 21. The NMOS transistor 2202 includes N-type wells 2208 and 2210. An N+ source region 2204 is formed in the N-type well 2208. An N+ drain region 2206 is formed in the N-type well 2210. The N-type wells 2208 and 2210 are separated by a P-type well 2214 and by the P-type substrate 1902. The P-type well 2214 is optional and may increase the threshold voltage at which the transistor 2202 breaks down. The N-type wells 2208 and 2210 may be thermally diffused.

The pattern illustrated by reference 2216 represents an example of a mask pattern for the N+ implant region. As shown, only part of the gate 2212 is doped N+.

A body contact for the NMOS transistor 2202 is not explicitly shown but may be included and may be formed, for example, by a P-type well with a P+ diffusion region.

The PMOS transistor 2218 includes a deep N-type well 2220 formed in the P-type substrate 1902. N-type wells 2222, 2250 and 2238 may be formed in the deep N-type well 2220. An N+ contact region 2224 serving as a body contact for the transistor may be formed in the N-type well 2222. Similarly, an N+ contact region 2236 serving as a body contact for the transistor may be formed in the N-type well 2238. N-type well 2250 represents an optional well which may increase the threshold voltage at which the transistor 2218 breaks down.

The transistor 2218 also includes P-type wells 2228 and 2234. A source region 2226 may be formed in the P-type well 2228 and a drain region 2232 may be formed in the P-type well 2234. A source contact 2230 contacts the source region 2226 and a drain contact 2240 contacts the drain region 2232. The transistor 2218 also includes P-type wells 2246, 2248, 2252, and 2254.

The pattern represented by reference 2244 is an example of a mask pattern for the P+ implant process for forming transistor 2218. As shown, only part of the gate 2242 is doped P+.

The ultrasound transducer probes described herein may implement various types of circuit components, at least some of which may be constructed using the high voltage designs described in connection with FIGS. 19-22 in those embodiments in which the ultrasound transducer probes are to operate with high voltages. Various non-limiting examples are now provided.

Figure 23:
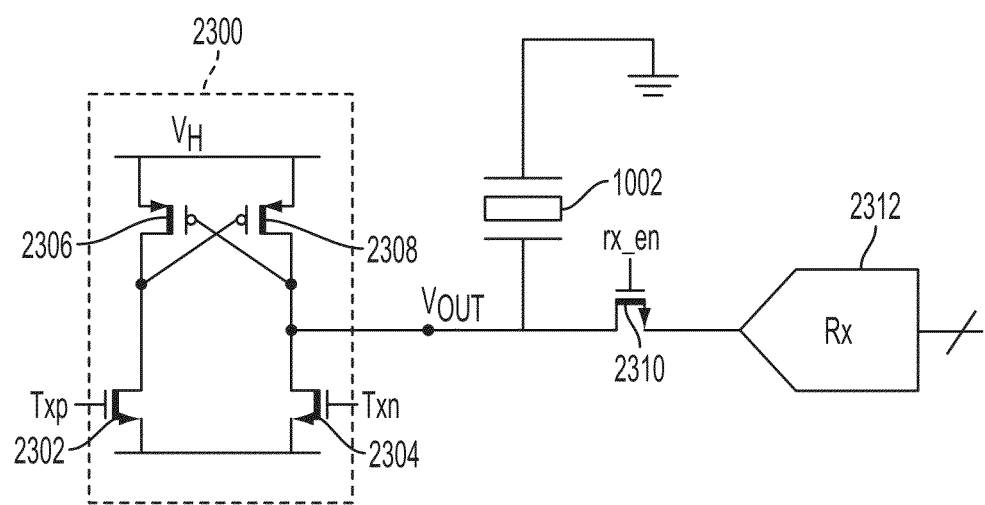
FIGS. 23, 24A, 24B, 25A, and 25B illustrate pulsers which are configured to support high voltage operation and which may be used in ultrasound transducer probes of the types described herein, according to various non-limiting embodiments of the present application.

FIG. 23 illustrates an example of a pulser using a high voltage NMOS and PMOS layout with a high voltage switch that may be used in some embodiments as an isolation switch. As shown, the pulser 2300 comprises four transistors 2302, 2304, 2306 and 2308. Transistors 2302 and 2304 are NMOS transistors and transistors 2306 and 2308 are PMOS transistors, though it should be appreciated that substantially the same pulser may be constructed by suitably reversing the polarities. The transistors may have thick gate oxides as indicated by the heavy black lines representing the gates, and thus such transistors may be high voltage transistors capable of withstanding the voltages of the magnitudes previously described.

The transistors 2302 and 2306 are connected in series between a high voltage VH and a reference potential, such as GND. Likewise, transistors 2304 and 2308 are connected in series between the voltage VH and the reference potential. Transistors 2302 and 2304 are controlled by respective enable signals Txp and Txn.

The output Vout of the pulser may be provided to an electrode of an ultrasound element, for example ultrasound element 1002. A second electrode of the ultrasound element 1002 may be connected to a reference potential, such as electrical ground. The ultrasound element 1002 may be connected to a receive circuitry module 2312 of the types previously described herein via a transistor switch 2310. The transistor switch 2310 may be a high voltage transistor switch and may be controlled by an enable signal rx_en to isolate the receive module 2312 from the high voltage.

The pulser 2300 may be disabled by setting Txp=0, Txn=1. Then, the value of Txn may be set to Txn=0. The PMOS transistors 2306 and 2308 will hold state as long as the Vout node stays within the low voltage rails of the circuit.

Figure 24A:
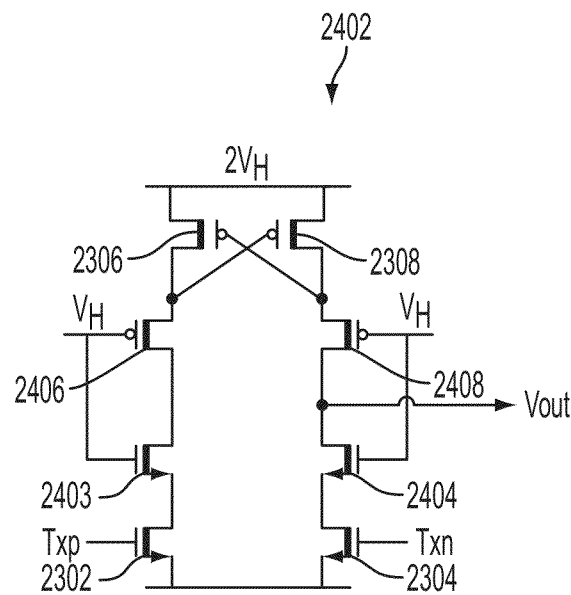
Figure 24B:
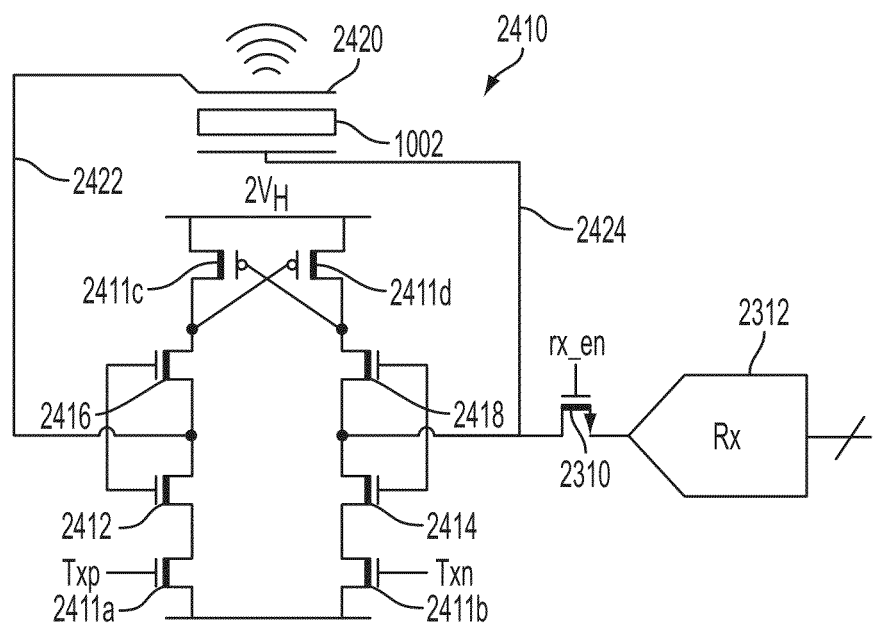

FIGS. 24A and 24B illustrate pulser configurations which may be used to support voltages two times and four times as great as the voltage supported by the pulser 2300, respectively. To produce a pulser which can sustain twice the voltage VH, i.e., to sustain 2VH, the pulser 2402 of FIG. 24A may be used. As shown, the pulser 2402 additionally comprises NMOS transistors 2403 and 2404, as well as PMOS transistors 2406 and 2408. The gates of transistors 2403 and 2406 are tied together and configured to receive the voltage VH, as are the gates of transistors 2404 and 2408.

To produce a pulser which can sustain four times the voltage VH, i.e., to sustain 4VH, the pulser 2410 shown in FIG. 24B may be used. The pulser 2410 includes NMOS transistors 2411a and 2411b and PMOS transistors 2411c and 2411d. In addition, the pulser 2410 comprises NMOS transistors 2412, 2414, 2416, and 2418. None of the illustrated transistors has a thick gate oxide. Transistors 2412 and 2416 are connected in series with their gates electrically tied together. Likewise, transistors 2414 and 2418 have their gates electrically tied together. An ultrasound element 2420 has a first terminal 2422 connected between transistors 2416 and 2412 and a second terminal 2424 connected between transistors 2414 and 2418. The terminals 2422 and 2424 are driven with an H-bridge circuit.

Figure 25A:
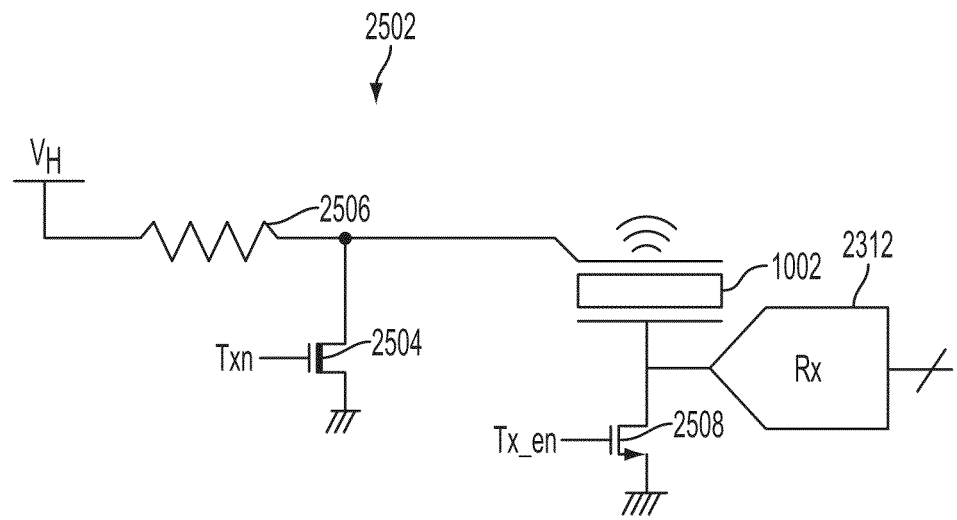
Figure 25B:
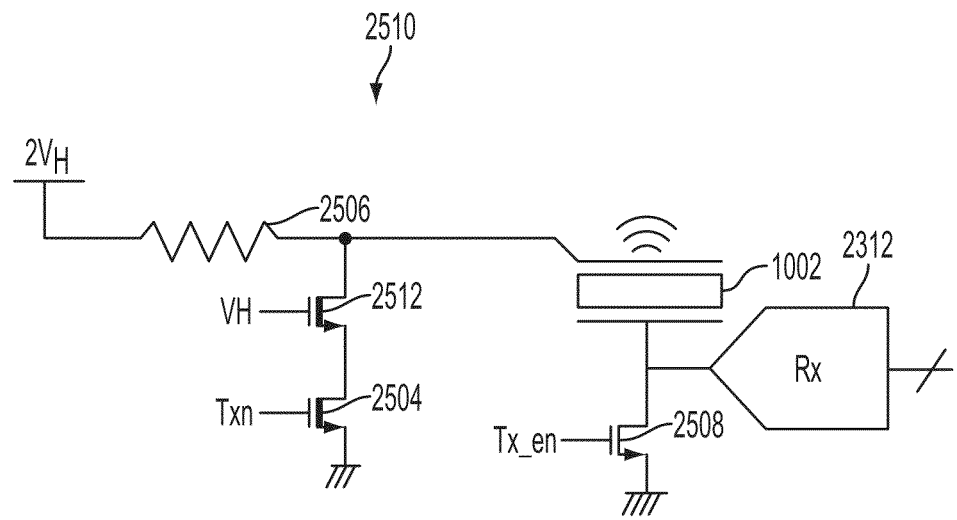

FIGS. 25A-25B show examples of pulser circuits that can sustain high voltages but which do not utilize a receive isolation switch. The pulser 2502 of FIG. 25A includes an NMOS transistor 2504 having a thick gate oxide and controlled by an input signal Txn. The drain of the transistor 2504 is coupled to a first electrode of an ultrasound element 1002 and also to a resistor 2506, which has its other terminal configured to receive the high voltage VH. The transistor 2504 operates as a high voltage NMOS pull down device. The resistor 2506 may be defined by an N-type well in a P-type substrate or by nonsilicided polysilicon on field oxide (FOX), as non-limiting examples.

The first electrode of the ultrasound element 1002 in FIG. 25A is connected to the resistor 2506 and may be automatically biased when the ultrasound element is operated in a receive mode. The second electrode of the ultrasound element 1002 is directly connected to receive circuitry module 2312 in FIG. 25A. Such a configuration may produce lower parasitics than the structures of FIGS. 24A and 24B. The second electrode of the ultrasound transducer probe is also connected to ground via an NMOS transistor 2508 actuated with transmit enable signal Tx_en.

FIG. 25B illustrates another example of a pulser which lacks a receive isolation switch. The pulser 2510 includes a cascaded transistor arrangement with transistors 2504 and 2512. The cascaded arrangement allows the pulser 2510 to sustain twice the voltage (2VH) sustained by the pulser 2502 of FIG. 25A. Transistor 2512 is controlled by voltage VH.

Figure 26A:
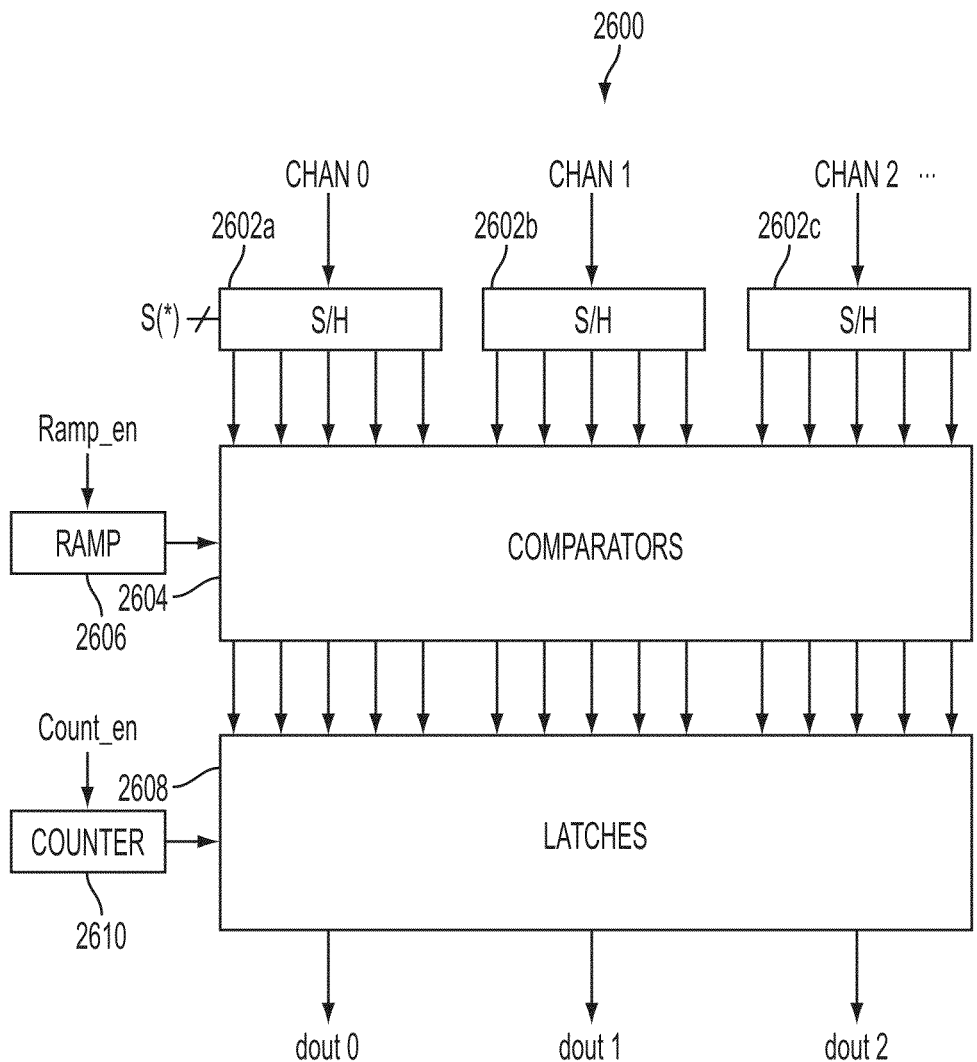
FIG. 26A illustrates an analog-to-digital converter (ADC) configured to support high voltage operation and which may be used in an ultrasound transducer probe according to a non-limiting embodiment of the present application.

FIG. 26A shows an example of a time-interleaved single slope ADC that, in some embodiments, may be employed as one or more of the ADCs of an ultrasound transducer probe referenced herein, for example as ADC 1020. In the illustrated example, N parallel ADCs are used for one channel to take alternating samples such that the sampling frequency of each ADC is much lower than the Nyquist criterion. Such single slope ADCs may, for example, allow large-scale sharing of resources, such as bias, ramp, and gray counter. Such an ADC approach may thus provide a highly scalable, low power option.

As shown, the ADC 2600 may include a plurality of sample & hold circuits 2602a, 2602b, 2602c . . . corresponding to different receive channels of an ultrasound transducer probe. The sample and hold circuits may receive a plurality of switching signals, illustrated collectively as S(*) via a switch signal input bus. The switching signals may control the sample and hold circuits to generate multiple (in this case five) samples per receive channel. The five samples per receive channel may be output from the sample and hold circuits to a comparator block 2604, which may also receive a ramp signal from a ramp circuit 2606. The ramp circuit 2606 is enabled by a signal ramp_en.

The comparator block 2604 compares the sampled values from the sample and hold circuits to the ramp signal and generates five corresponding output values provided in parallel per receive channel. The outputs of the comparator block 2604 are provided to latches 2608, which are latched by a counter 2610. The counter 2610 is enabled by a signal count_en. The latches 2608 output digital signals corresponding to the respective channels, i.e., dout0 for channel 0, dout1 for channel 1, dout2₂ for channel 2, etc. The digital signals represent serial digital outputs.

Figure 26B:
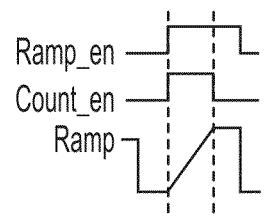
FIG. 26B is a timing diagram illustrating various signals relating to the operation of the ADC of FIG. 26A.

FIG. 26B illustrates a timing diagram for the signal ramp_en, count_en, and ramp (the output of the ramp circuit 2606). As shown, the ramp_en and count_en signals may transition high at approximately the same time, triggering an increase in the ramp signal. The count_en signal may then transition low at which time the ramp signal plateaus. When the ramp_en signal subsequently transitions low the ramp signal does the same.

Figure 27:
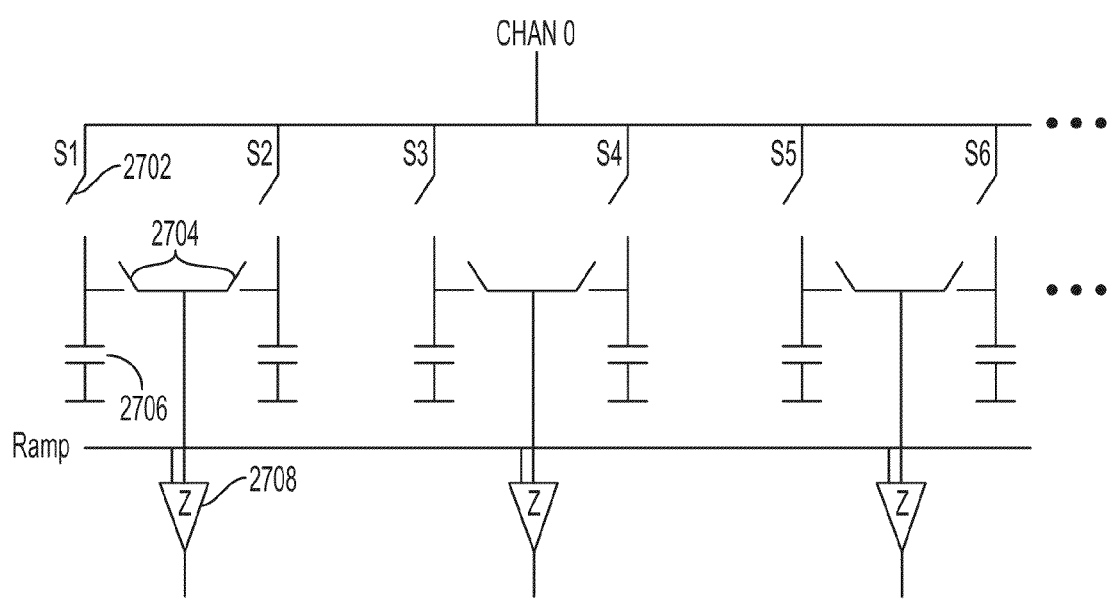
FIG. 27 illustrates a sample and hold circuit configured to support high voltage operation and which may be used in an ultrasound transducer probe according to a non-limiting embodiment of the present application.

FIG. 27 expands on the sample and hold circuits and comparators of FIG. 26A. In particular, FIG. 27 illustrates a portion of a single sample and hold circuit (e.g., sample and hold circuit 2602a) and the corresponding comparators 2604. The data from the receive channel (receive channel 0 in this case) is provided to a set of switches 2702 controlled by respective switching signals S1-S6. In some embodiments, a total of ten such switches may be provided to produce the five samples from the sample and hold circuit 2602a, but only six are shown for simplicity. The switches 2702 capture samples of the signal from channel 0 on respective capacitors 2706.

Switches 2704 may also be provided and are closed in any specified sequence to provide the values from the capacitors 2706 to an input of the comparators 2708. The comparators 2708 also receive the ramp signal of FIG. 26A. The outputs of the comparators 2708 correspond to the outputs of comparator block 2604 of FIG. 26A.

Figure 28A:
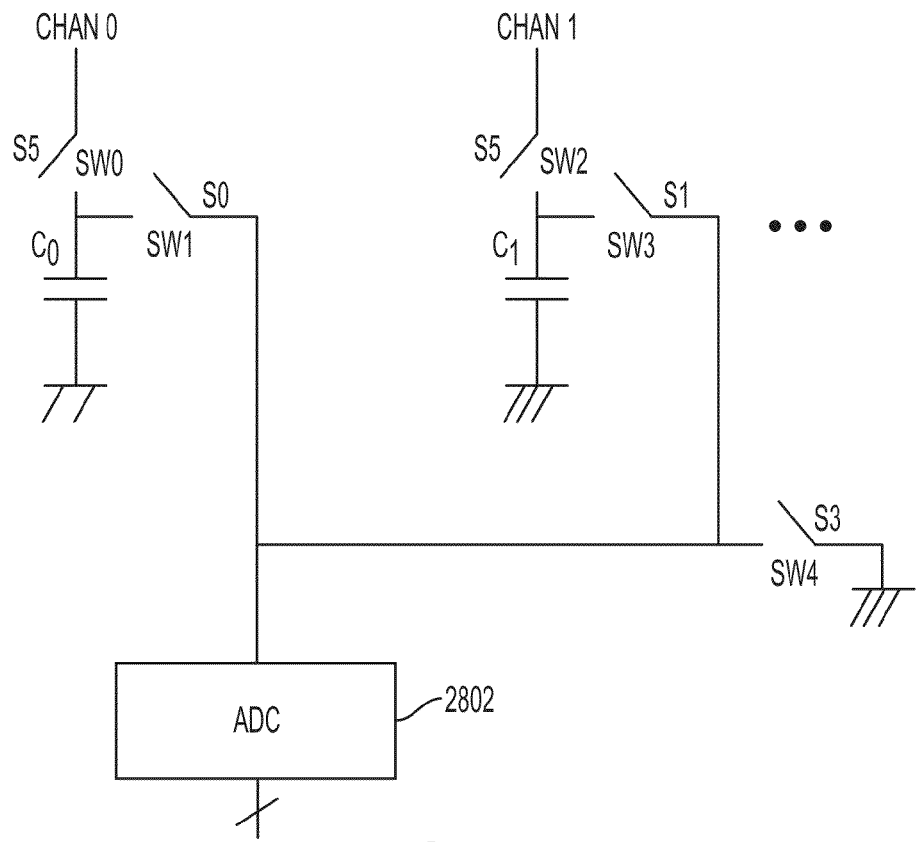
FIG. 28A illustrates a time-shared ADC which may be used in an ultrasound transducer probe according to a non-limiting embodiment of the present application.

FIG. 28A shows an example of a time shared high speed ADC that, in some embodiments, may be employed as one or more of the ADCs referenced herein for use in an ultrasound transducer probe, for example as ADC 1020. Such an ADC may, for example, employ a pipelined, successive-approximation-register (SAR), or flash architecture. Because a single high speed ADC having such an architecture may be used to sample N channels, such an ADC may significantly reduce area requirements.

As shown, the ADC 2802 may be configured to receive data from a plurality of channels (i.e., receive channels of an ultrasound transducer probe) including channel 0 and channel 1. A capacitor C0 may be coupled between a switch SW0, controlled by signal S5, and ground. Switch SW1, controlled by signal S0, may be operable to connect the ADC 2802 suitably to receive data from channel 0.

Channel 1 may be coupled to the ADC 2802 via switches SW2 and SW3, controlled by signals S5 and S1, respectively. A capacitor C1 may be coupled between the switch SW2 and a reference voltage, such as ground. A switch SW4, controlled by signal S3, may also be provided to connect the input of the ADC 2802 directly to the reference voltage, e.g., ground.

Figure 28B:
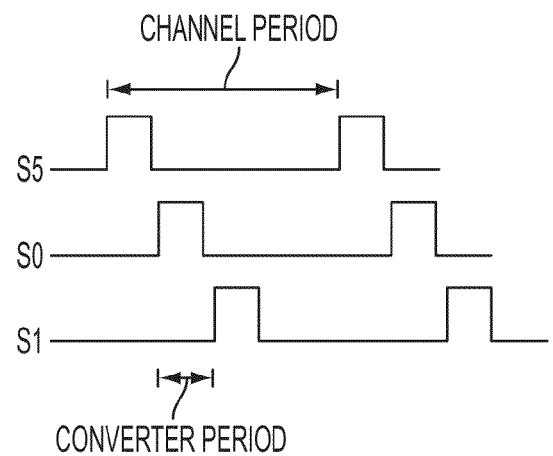
FIG. 28B illustrates a timing diagram of the operation of the ADC of FIG. 28A.

FIG. 28B illustrates an exemplary timing diagram for operation of switches SW0, SW1, SW2, and SW3. A channel period is defined as having a duration from the beginning of one pulse of the signal S5 to the beginning of a second pulse. A converter period is defined as the beginning of one pulse of the signal S0 to the beginning of the next pulse of signal S1.

The high voltage CMOS circuitry described herein may be configured to drive voltages higher than those conventionally attainable with CMOS circuitry, and to provide high voltages at deep submicron nodes. In some embodiments, voltages up to approximately 10 V may be supported or driven, up to approximately 20 V may be supported or driven, up to approximately 30 V may be supported or driven, up to approximately 40 V may be supported or driven, up to approximately 50 V may be supported or driven, up to approximately 60 V may be supported or driven, voltages between 20 V and 120 V may be supported or driven, between 30 V and 80 V, between 40 V and 60 V, or any other suitable voltage within those ranges, or other suitable voltages, as non-limiting examples.

Figure 29A:
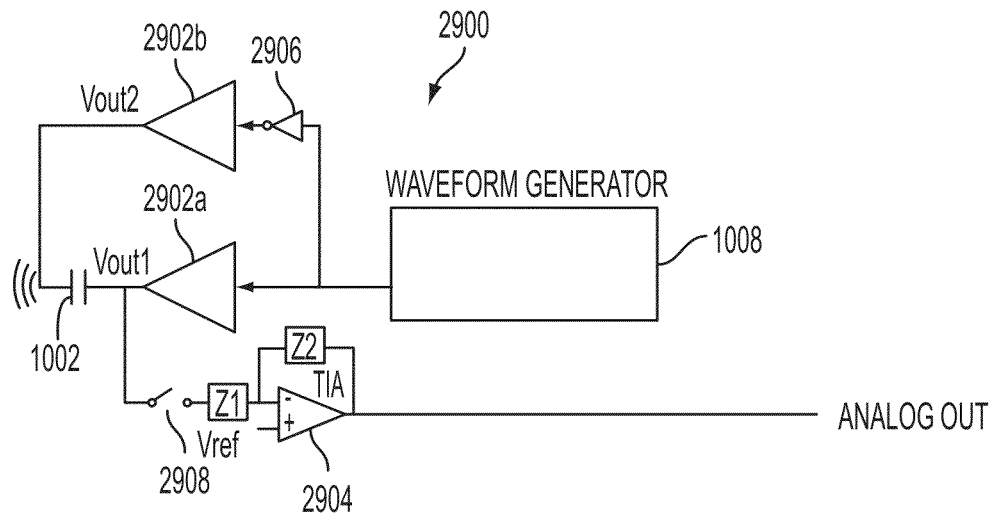
FIG. 29A illustrates a circuit configuration including two pulsers coupled to an ultrasound element, according to a non-limiting embodiment of the present application.

As described previously, embodiments of the present application provide an ultrasound transducer probe having one or more pulser circuits. When operating an ultrasound transducer probe at high voltages, such as those described in connection with FIGS. 19-28B, having a single pulser connected to an ultrasound element may create difficulties by requiring the pulser to create very large voltage swings. For instance, the pulser configuration of FIG. 10 may require the pulser to create very large voltage swings if the ultrasonic transducers are to be operated at high voltages. To address this potential drawback of the circuit configuration of FIG. 10, an alternative configuration utilizing two pulsers per ultrasound element may be used in some embodiments. FIG. 29A illustrates an example.

As shown, the circuit 2900 includes the ultrasound element 1002, the waveform generator 1008 and two pulsers 2902a and 2902b. Pulser 2902a is coupled to a first electrode of the ultrasound element 1002 and pulser 2902b is coupled to a second electrode of the ultrasound element 1002. An inverting amplifier 2906 is coupled to the input of the pulser 2902b to provide an inverted version of the waveform from waveform generator 1008. The circuit 2900 also includes a TIA 2904 and impedances Z1 and Z2. A T/R switch 2908 couples the TIA 2904 to the ultrasound element 1002.

By utilizing the pulser configuration of FIG. 29A, each of the two pulsers need only generate half the voltage swing that would be generated by the pulser in FIG. 10. Such a configuration may be advantageous in those embodiments in which the ultrasonic transducers of the ultrasound transducer probe are not electrically tied together (e.g., do not all share a common electrode). The configuration of FIG. 29A may be less advantageous in those embodiments in which the ultrasonic transducers of the ultrasound transducer probe are electrically tied together and biased together (e.g., when a common electrode, such as a top electrode, of the ultrasonic transducers is used to bias the transducers together).

Figure 29B:
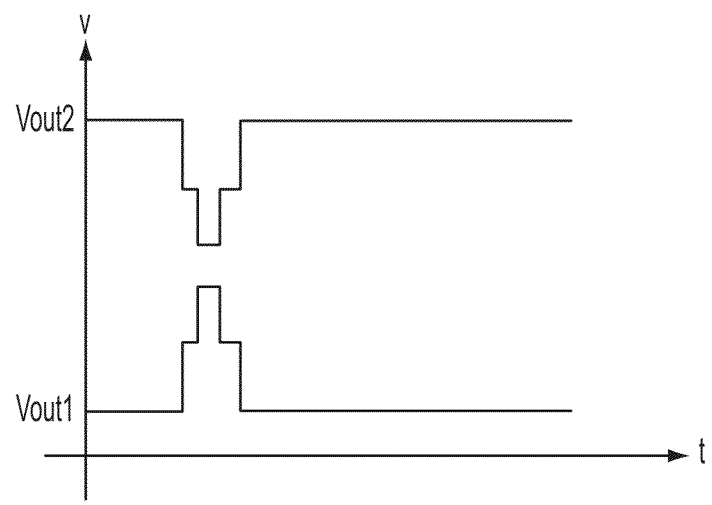
FIG. 29B is a timing diagram of the operation of the pulsers of FIG. 29A.

The operation of the pulsers 2902a and 2902b can be further understood by reference to FIG. 29B. FIG. 29B illustrates the operation of signals Vout1 and Vout2, corresponding to the output voltages of pulsers 2902a and 2902b, respectively, as a function of time. As shown, each of the two pulsers need exhibit approximately half the voltage swing between Vout1 and Vout2 to effectively create a voltage swing from Vout1 to Vout2. The pulsers 2902a and 2902b may be tri-level pulsers of the types previously described herein, and thus each may exhibit three voltage levels in the output signal as shown in FIG. 29B.

Operating Modes

According to some aspects of the present application, the ultrasound transducer probes described herein may be used for ultrasound imaging, and when so used may be configured to operate in various imaging modes. Some embodiments provide for 2D and 3D imaging. When 2D ultrasound imaging is performed, alternative manners may be utilized. According to one manner of 2D operation, the ultrasound transducer probe may collect a time domain signal echo across one dimension of the arrangement of ultrasonic transducers. An alternative method may involve collecting ultrasound intensity data across two dimensions of the arrangement of ultrasonic transducers, but not measuring a time dimension. In some embodiments, a spectral domain signal may be used. In some embodiments, tomographic imaging may be utilized. The mode may be selected by a user in some embodiments. Non-limiting examples of imaging modes which may be utilized are now described.

One example of an imaging mode which may be exhibited is B-mode imaging. Plane wave imaging, virtual source imaging, all-pairs imaging, and focused beam imaging are all examples of B-mode imaging which may be implemented according to various embodiments.

Another imaging mode which may be used is M-mode imaging. This includes single line and multi-line M-mode imaging according to some embodiments.

Doppler imaging may also be performed with the ultrasound transducer probes according to various embodiments. Pulsed and vector flow Doppler imaging are examples of Doppler modes which may be implemented.

Shear wave imaging is another example of an imaging mode which may be implemented.

Harmonic imaging is another example of an imaging mode which may be implemented. Pulse inversion, 3-pulse inversion, and coded excitation operating schemes are enhancements to harmonic imaging which may also be implemented.

Verberation flow imaging (V-flow) may also be used in some embodiments.

The ability to exhibit such varied imaging modes may be due at least in part to the configurability of the ultrasound transducer probes. The transmit operation of an ultrasound transducer probe of the types described herein may be flexible. For example, the transmit operation may be controlled by parameters which are selectable, such as the parameters of a programmable waveform generator of the types described herein. For instance, the delay, amplitude, length, initial phase, initial frequency, and/or ramp rate of a desired excitation may be programmed into a waveform generator. In some embodiments, the parameterization may be substantially or fully arbitrary. Control over the start and stop of transmit operations may be provided in any suitable manner, such as with an enable signal. The transmit voltages may be adjustable.

The receive operation of ultrasound transducer probes of the types described herein may also be flexible, exhibiting significant configurability. For example, as described in connection with FIGS. 9 and 10, the manner in which signals are read out from ultrasound elements may include electrically tying multiple ultrasound elements to common receive circuitry, or alternatively each ultrasound element may have its own dedicated receive circuitry. Thus, the amount of ultrasound data generated by an ultrasound transducer probe may be selectable.

The use of external links for communicating between an ultrasound transducer probe and an external device may be configurable according to aspects of the present application and may be selected based on an intended imaging mode. For example, the maximum number of available links may be utilized in embodiments in which it is desirable to maximize data output from the ultrasound transducer probe, and may allow for large quantities of data to be offloaded from the ultrasound transducer probe without averaging or other data reduction processing. Alternatively, fewer than the maximum number of links available may be utilized in embodiments in which maximum data is not needed. For example, half the links or only a single link may be utilized. In such embodiments, averaging of data may be implemented to facilitate offloading of a sufficient amount of data to support desired end user applications, such as ultrasound imaging.

The data format processed by the ultrasound transducer probe may also be configurable. For example, full waveforms may be processed in some embodiments. Alternatively, peak values may be processed, which may allow for a reduction in the data processing requirements of the ultrasound transducer probe.

Various additional parameters of the ultrasound transducer probe operation may be configurable. Such parameters include the receive window, channel subselection, the TGC configuration, data reduction parameters such as averaging or data dropping parameters, pulse repetition intervals, event sequencing intervals, quantizer configurations, and filter taps, among others.

Thus, it should be appreciated that the architecture of the ultrasound transducer probe in terms of the ultrasound transducers and control circuitry may facilitate use of the ultrasound transducer probe in a variety of modes of operation for a variety of applications. Accordingly, ultrasound transducer probes according to one or more aspects of the present application may represent sophisticated and versatile ultrasound devices configurable to create an ultrasound transducer probe geometry of choice.

Moreover, as has been described previously, for example in connection with FIGS. 2A-2G, ultrasound transducer probes serving as repeatable units that are capable of being tiled are provided. Such transducer probes may be fabricated, in some embodiments, by tiling and dicing together multiple instances of an ultrasound transducer probe to create an ultrasound transducer probe capable of exhibiting desired imaging functionality. In some embodiments, individual instances of an ultrasound transducer probe may be diced and subsequently tiled and interconnected suitably to form an ultrasound transducer probe with desired imaging functionality. Therefore, flexibility in the ultrasound device achieved and the imaging capabilities of that ultrasound device are provided by the simple and flexible manner of fabricating multiple instances of a repeatable ultrasound unit.

Transducer

The ultrasonic transducers of ultrasound transducer probes of the types described herein may be any suitable ultrasonic transducers, and in some embodiments may have features which facilitate creation of stand-alone ultrasound transducer probes exhibiting a high degree of integration. In some embodiments, the ultrasonic transducers may be compatible with a CMOS substrate, thus allowing them to be monolithically formed on a CMOS substrate with CMOS ICs. In this manner, an integrated device (e.g., an ultrasound system-on-a-chip) may be formed.

In some embodiments, the ultrasonic transducers may be CMOS ultrasonic transducers (CUTs). A CUT may, for example, include a cavity formed in a CMOS wafer, with a membrane (or diaphragm) overlying the cavity, and in some embodiments sealing the cavity. Electrodes may be provided to create a transducer cell from the covered cavity structure. The CMOS wafer may include integrated circuitry to which the transducer cell may be connected. The transducer cell and CMOS wafer may be monolithically integrated, thus forming an integrated ultrasonic transducer cell and IC on a single substrate (the CMOS wafer).

CUTs are not the only type of ultrasonic transducer which may allow for integration of the transducer with an IC. In some embodiments, the ultrasonic transducers may be capacitive micromachined ultrasonic transducers (CMUTs).

Not all embodiments are limited to employing CUTs or CMUTs in an ultrasound transducer probe of the types described herein. Some aspects of the present application apply to ultrasound transducer probes irrespective of the type of ultrasonic transducer implemented.

According to an aspect of the present application, ultrasonic transducers are formed above a thick top metal layer of a CMOS substrate. Ultrasound transducer probes according to aspects of the present application may include an arrangement of ultrasonic transducers on a CMOS substrate. The arrangement of ultrasonic transducers may span a distance which is relatively long in terms of signal transmission properties, which may run a risk of exhibiting relatively high impedances, and thus performance degradation. The problem may be enhanced if the ultrasound transducer probe comprises a CMOS substrate which is wider than it is tall (e.g., a wide aspect ratio substrate), which, as previously described, may be used in some embodiments. Use of a thick top metal layer of the CMOS substrate for power and ground signal distribution may at least partially mitigate the difficulties associated with long signal paths on the CMOS substrate. A metal layer may be "thick" when having a thickness greater than approximately 0.5 microns, for example having a thickness between approximately 0.5 microns and approximately 10 microns. A thick top metal layer may be referred to in some embodiments as an ultra-thick redistribution layer.

When a thick top metal layer of the CMOS substrate is reserved for power and ground signal distribution, an ultrasonic transducer formed above such a thick top metal layer may be connected to the thick top metal layer using vias or other suitable structures. CUTs and CMUTs often employ two or more electrodes. Connection of the electrode(s) of the ultrasonic transducer to the thick top metal layer may be made with one or more vias.

While some aspects of the present application implementing a metal layer for power and ground signal distribution utilize a thick top metal layer for such distribution, not all aspects are limited in this respect. For example, a top metal layer which is not necessarily thick may be employed in some embodiments. Moreover, the metal layer need not be the top metal layer in all embodiments. Various examples of ultrasonic transducers according to aspects of the present application are now illustrated and described. Each is described as including a top metal layer, which may be thick in any of the illustrated embodiments.

Transducer Example 1

Several examples of ultrasonic transducers integrated with a CMOS substrate and formed above a (top) metal layer of the CMOS substrate are now described. FIG. 30A illustrates a first example. The device 3000 includes a CMOS substrate 3002 on which is formed an ultrasonic transducer (e.g., a CUT) 3004.

The CMOS substrate 3002 represents a non-limiting example of a suitable CMOS substrate, and it should be appreciated that alternative CMOS substrates may be utilized. In the example of FIG. 30A, the CMOS substrate 3002 includes a semiconductor substrate 3006, which may be a silicon substrate (e.g., a bulk silicon wafer), or any other suitable semiconductor substrate. An insulating layer 3008, for example of $SiO_2$, is on the semiconductor substrate 3006. A conductive layer 3010 is on the insulating layer 3008 and covered by a second insulating layer 3012. The conductive layer 3010 may be a metallization layer in some embodiments, and may be patterned as shown to form a plurality of signal lines. For example, the conductive layer 3010 may be formed of aluminum with bottom and top liner layers. The insulating layer 3012 may be $SiO_2$ or any other suitable insulating material.

A top metal layer 3014 is included with the CMOS substrate 3002, having a thickness $T_m$. The top metal layer 3014 may be a thick metal layer in some embodiments, and in such embodiments the thickness $T_m$ may be between approximately 0.5 microns and approximately 10 microns, between approximately 2 microns and approximately 5 microns, any range or value within such ranges, or any other suitable value for providing decreased resistivity to facilitate functioning of the top metal layer 3014 as a signal distribution layer. The top metal layer 3014 may be patterned to create an island 3017, described further below. In addition, stress relieving openings or cuts may optionally be formed in the top metal layer 3014.

In some embodiments, the top metal layer 3014 may have liner layers above and below, such as liners 3013a and 3013b. For example, the top metal layer 3014 may be formed of aluminum with a TiN liner above and below. In some embodiments, a liner may be a multi-layer structure, for example being formed of two or more metals. As a non-limiting example, liner 3013b may include a first layer of titanium nitride (TiN) and a second layer of silicon oxynitride (SiON). SiON may be used in some embodiments as a top layer of a metallization layer since it may serve as an anti-reflective coating for photolithography purposes. Any liner included below and/or above the top metal layer may be a thin film.

The CMOS substrate 3002 further comprises an insulating layer 3016. The insulating layer 3016 may be formed of any suitable insulating material, a non-limiting example of which is $SiO_2$.

The ultrasonic transducer 3004 includes several components. A membrane 3018 overlies a cavity 3020 in the CMOS substrate 3002. In some embodiments, the membrane 3018 seals the cavity 3020, for instance providing a vacuum. A conductive layer 3030 formed of any suitable conductive material to provide electrical connection to a bottom side of the membrane 3018 is also provided. As a non-limiting example, the conductive layer 3030 may be formed of a thin film, for example being formed of TiN.

The cavity 3020 overlies an electrode 3022 which may be considered a bottom electrode of the ultrasonic transducer 3004. The electrode 3022 may be formed of any suitable conductive material. In some embodiments, the electrode 3022 may be formed of a thin film material, such as TiN. In some embodiments, TiN may be used as an etch stop for etching the cavity 3020 in the CMOS substrate 3002. Alternatives are possible.

The sidewalls of the cavity 3020 are formed by conductive spacers 3024, which may perform various functions. For example, the conductive spacers 3024 may at least partially define the depth of the cavity 3020. The conductive spacers, sometimes in combination with other structures, may electrically connect the membrane 3018 to the top metal layer 3014. The conductive spacers 3024 may be formed of any suitable conductive material. In some embodiments, the conductive spacers 3024 may be formed of TiN, although other conductive materials may alternatively be used.

The device 3000 also includes multiple vias, disposed in the insulating layer 3016. Three such vias 3026a-3026c are illustrated. The vias 3026a-3026c may be formed of any suitable conductive material, a non-limiting example of which is tungsten (W). The vias 3026a and 3026c may provide electrical connection between the top metal layer 3014 and conductive contacts 3028a-3028b, respectively, on which the conductive spacers 3024 are disposed. The conductive contacts 3028a-3028b may be formed of any suitable conductive material, a non-limiting example of which is TiN. The via 3026b electrically connects the electrode 3022 to the island 3017 of the top metal layer 3014.

As shown, additional insulating layers 3032 and 3034 are included in the device 3000. The insulating layer 3034 may substantially cover the bottom electrode 3022 and may provide electrical insulation. Insulating layers 3032 and 3034 may be formed of any suitable insulating material, a non-limiting example of which is $SiO_2$.

Additional structures of the device 3000 may provide electrical connection between the substrate 3006 and the electrode 3022. For instance, vias 3007 and 3009 may connect the electrode 3022 to the substrate 3006 by way of the conductive layer 3010. The vias 3007 and 3009 may be formed of any suitable conductive materials, a non-limiting example of which is tungsten.

The device 3000 may have any suitable dimensions. For example, the cavity 3020 may have a depth DC between approximately 0.05 microns and approximately 10 microns, between approximately 0.1 microns and approximately 5 microns, between approximately 0.5 microns and approximately 1.5 microns, any depth or range of depths in between, or any other suitable depth.

The width WC of the cavity 3020 may be between approximately 5 microns and approximately 500 microns, between approximately 20 microns and approximately 100 microns, may be approximately 30 microns, approximately 40 microns, approximately 50 microns, any width or range of widths in between, or any other suitable width. In some embodiments, the width may be selected to maximize the void fraction, i.e., the amount of area consumed by the cavity compared to the amount of area consumed by surrounding structures. The width dimension may also be used to identify the aperture size of the cavity, and thus the cavities may have apertures of any of the values described above or any other suitable values.

It can be seen from FIG. 30A that the electrode 3022 may not be as wide as the cavity 3020. Such a configuration may be desirable when the sidewalls of the cavity are formed of a conductive material, to prevent electrical breakdown between the bottom electrode 3022 of the ultrasonic transducer and the cavity sidewalls. However, not all embodiments are limited in this respect, as ultrasonic transducers usable in ultrasound transducer probes of the present application may have bottom electrodes that are as wide as, or wider than, the cavity.

The membrane thickness T1 (e.g., as measured in the direction generally parallel to the depth DC) may be less than 100 microns, less than 50 microns, less than 40 microns, less than 30 microns, less than 20 microns, less than 10 microns, less than 5 microns, less than 1 micron, less than 0.1 microns, any thickness or range of thicknesses in between, or any other suitable thickness. The thickness may be selected in some embodiments based on a desired acoustic behavior of the membrane, such as a desired resonance frequency of the membrane.

In some embodiments, the cavity dimensions and/or the membrane thickness of any membrane overlying the cavity may impact the frequency behavior of the membrane, and thus may be selected to provide a desired frequency behavior (e.g., a desired resonance frequency of the membrane). For example, it may be desired in some embodiments to have an ultrasonic transducer with a center resonance frequency of between approximately 20 kHz and approximately 200 MHz, between approximately 1 MHz and approximately 10 MHz, between approximately 2 MHz and approximately 5 MHz, between approximately 50 kHz and approximately 200 kHz, of approximately 2.5 MHz, approximately 4 MHz, any frequency or range of frequencies in between, or any other suitable frequency. For example, it may be desired to use the devices in air, gas, water, or other environments, for example for medical imaging, materials analysis, or for other reasons for which various frequencies of operation may be desired. The dimensions of the cavity and/or membrane may be selected accordingly.

Also, it should be appreciated that the cavity 3020, and more generally the cavities of any embodiments described herein, may have various shapes, and that when multiple cavities are formed not all cavities need have the same shape or size. For example, when considering a top view of the cavity 3020, the cavity may have a square aperture, a circular aperture (e.g., as in FIG. 5B), a hexagonal aperture, an octagonal aperture, or any other suitable shape.

It should be appreciated from FIG. 30A that an ultrasonic transducer may be integrated with a CMOS substrate and that electrical contact may be made between upper and lower electrodes of the ultrasonic transducer and a top metal layer of the CMOS substrate with one or more vias. Also, the top metal layer (e.g., top metal layer 3014) of the CMOS substrate may be suitably patterned or segmented as shown to provide electrical isolation between the bottom electrode 3022 and the conductive layer 3030 of the ultrasonic transducer. For example, the island 3017 may provide electrical isolation between the electrode 3022 and the conductive layer 3030.

As previously described, the conductive layer 3010 may be patterned to form a plurality of signal lines. The top metal layer 3014 may, in some embodiments, shield the signals lines from the ultrasonic transducer 3004. Such a configuration may facilitate transmission of signals on the CMOS substrate 3002.

It should be appreciated that device 3000 illustrates an example of a device including embedded conductive structures in a CMOS substrate providing electrical connection to the membrane of an ultrasonic transducer. For example, vias 3026a-3026c are embedded in the CMOS substrate and form at least part of respective electrical paths from conductive layers of the CMOS substrate 3002 to electrodes of the ultrasonic transducer 3004.

Transducer Fabrication Example

Figure 37:
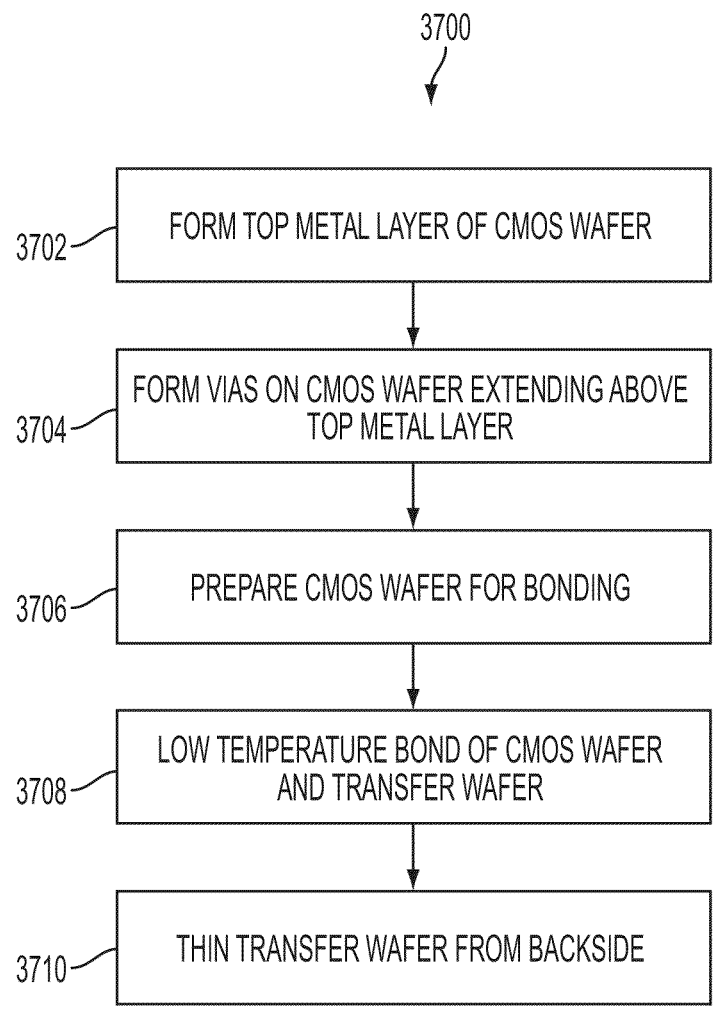
FIG. 37 illustrates a block diagram of a process for fabricating an ultrasonic transducer on a CMOS wafer, according to a non-limiting embodiment of the present application.

Various processes may be used to form devices including ultrasonic transducers integrated with a CMOS substrate of the types described herein. FIG. 37 is a flow chart illustrating an example. The method 3700 includes stage 3702 at which a CMOS wafer is processed to form a top metal layer, which optionally may be a thick top metal layer.

At stage 3704, the CMOS wafer may be processed to form one or more vias extending above the top metal layer. Such vias may be used to provide electrical connection between the top metal layer and an electrode of a subsequently formed ultrasonic transducer.

At stage 3706, the CMOS wafer may be prepared for wafer bonding with a transfer wafer. Such preparation may involve, for example, planarization and surface treatment.

At stage 3708, the CMOS wafer and the transfer wafer may be bonded using a low temperature bonding process. The transfer wafer may include one or more layers forming a membrane of an ultrasonic transducer of the bonded device. In some embodiments, the bonding may seal one or more cavities in the CMOS wafer.

At stage 3710, the transfer wafer may be thinned from the backside to leave the desired membrane.

It should be appreciated that variations on the method 3700 are possible. For example, stage 3704 may be performed after wafer bonding in some embodiments.

A process for fabricating the device 3000 consistent with the method 3700 is now illustrated and described, beginning with FIG. 30B. It will be appreciated that various processing steps may be performed prior to the stage illustrated in FIG. 30B to arrive at the illustrated structure. For instance, insulating layer 3008 may be formed on the semiconductor substrate 3006 and then patterned to allow formation of via 3007, for example by deposition of tungsten. Conductive layer 3010 may then be formed and patterned. According to an embodiment, the conductive layer 3010 may be formed of aluminum and may include bottom and top liner layers, for example of TiN, SiON, both, or any other suitable liner material. According to an embodiment, a layer of TiN and a layer of SiON may be formed on the top surface of conductive layer 3010. The conductive layer 3010 may be patterned as shown, for example to form a plurality of wiring lines.

Subsequently, insulating layer 3012 may be formed, for example by suitable deposition and planarization. The insulating layer 3012 may then be patterned and filled with conductive material (e.g., tungsten) to form via 3009. An etch back step or other planarization step may then be performed to provide a substantially planar upper surface.

The liner 3013a may then be deposited, followed by deposition of the top metal layer 3014. The liner 3013b may then be deposited.

As shown in FIG. 30B, the top metal layer 3014 may then be patterned to form a plurality of openings 3015, thus defining the island or other segment 3017. The patterning may involve any suitable etch technique for a (thick) metal layer, and as shown may involve etching through the entire thickness of the top metal layer 3014. The island 3017 may be electrically isolated from other segments of the top metal layer 3014 so that the island 3017 may be used to make contact to an electrode of the ultrasonic transducer 3004 as shown in FIG. 30A.

Referring to FIG. 30C, the insulating layer 3016 may then be formed by depositing an insulating material to fill the openings 3015, for example using a high density plasma (HDP) deposition (e.g., HDP deposition of $SiO_2$). The insulating material may then be planarized and patterned to form openings which may be filled with a conductive material to create vias 3026a-3026c. The conductive material deposited to fill the openings in the insulating layer 3016 to form the vias 3026a-3026c may be deposited conformally, for example using chemical vapor deposition (CVD).

The conductive material may then be etched back to have an upper surface substantially even with an upper surface of the insulating layer 3016, thus completing the structure shown in FIG. 30C.

As shown in FIG. 30D, a conductive layer may be deposited and patterned to form the bottom electrode 3022 and the conductive contacts 3028a-3028b. Any suitable deposition or formation technique may be used to form the conductive layer, and any suitable etching technique may be used to pattern the conductive layer to achieve the structure illustrated in FIG. 30D. In some embodiments, the conductive material used to form electrode 3022 and conductive contacts 3028a-3028b is a material suitable for thin film deposition, such as TiN. The illustrated manner of forming the bottom electrode 3022 and conductive contacts 3028a-3028b from a common conductive layer may represent a valuable process simplification in some embodiments compared to if separate depositions were used to form those structures.

Next, referring to FIG. 30E, insulating layer 3032 may be formed, for example by depositing an insulating material conformally on the structure of FIG. 30D, to cover the bottom electrode 3022 and conductive contacts 3028a-3028b. Then, the insulating layer 3032 may be etched back using any suitable etch technique or planarization technique, for example chemical mechanical polishing (CMP), such that the insulating layer 3032 has an upper surface below the upper surfaces of the electrode 3022 and conductive contacts 3028a-3028b, as shown. As previously described, the insulating layer 3032 may be formed of any suitable insulating material, a non-limiting example of which is $SiO_2$.

Then, insulating layer 3034 may be deposited conformally and etched back to provide a desired thickness. The insulating layer 3034 may cover the bottom electrode 3022 and conductive contacts 3028a-3028b at this stage of processing. The thickness of insulating layer 3034 may assume any suitable value for covering the bottom electrode 3022 to provide electrical insulation between the bottom electrode 3022 and the conductive layer 3030 of FIG. 30A in the event that the conductive layer 3030 comes into contact with the bottom electrode 3022.

Referring now to FIG. 30F, openings may be formed in the insulating layer 3034 above the conductive contacts 3028a-3028b using any suitable patterning technique. The conductive spacers 3024 may then be formed by depositing a conductive material, planarizing, and patterning the conductive material, as an example. The conductive spacers 3024 may be formed to have a desired thickness for the cavity 3020 shown in FIG. 30A.

Surface treatment may then be performed as appropriate to prepare the CMOS substrate for bonding to a transfer wafer.

Figure 30G:
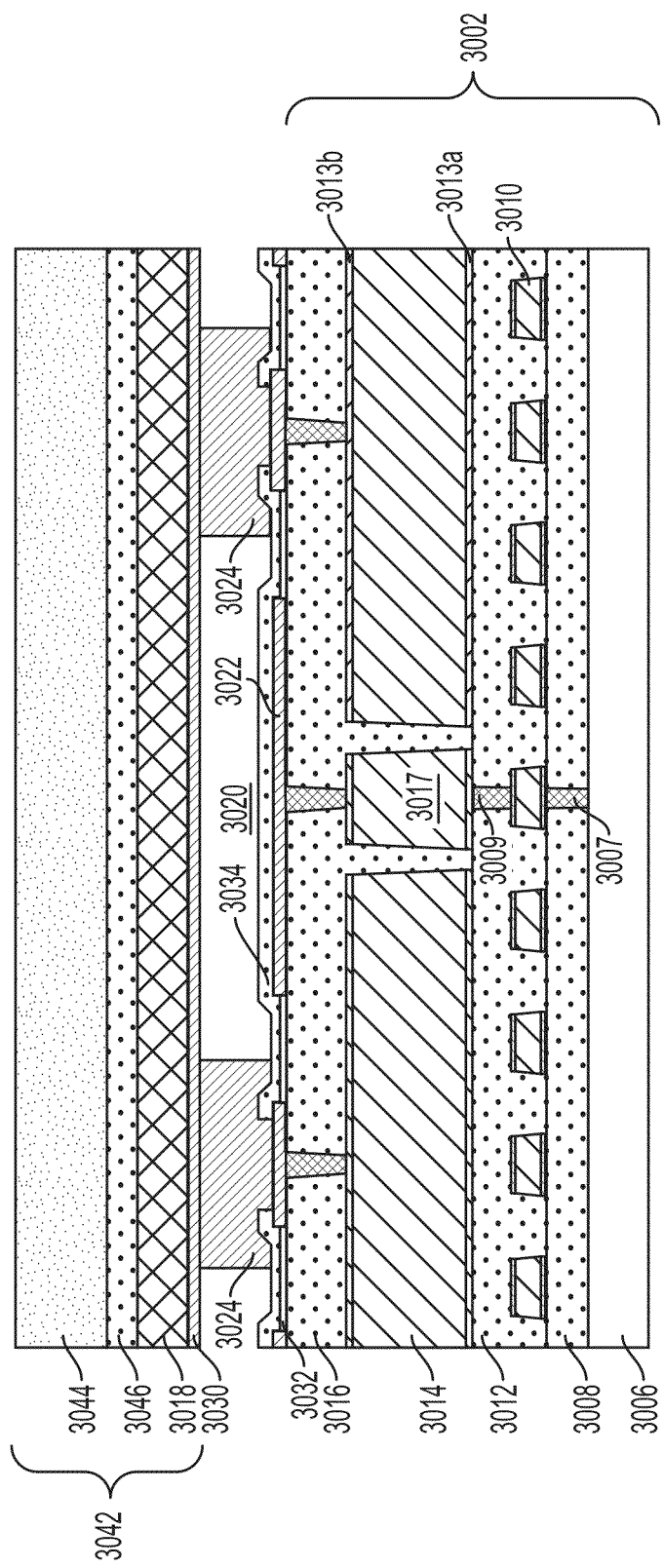

Referring to FIG. 30G, a wafer 3042 may be bonded with the CMOS substrate 3002 to cover, and in some instances seal, the cavity 3020. The wafer 3042 may be considered a second wafer, in addition to the CMOS wafer, and may also be referred to as a transfer wafer or handle wafer in some embodiments since it may, for example, transfer a membrane to the CMOS substrate. It should be appreciated, therefore, that fabrication of ultrasonic transducers may involve wafer level processing, including wafer level bonding, which may facilitate cost effective fabrication of large numbers of the ultrasonic transducers.

The wafer 3042 may include the membrane 3018 and conductive layer 3030, and thus may function as a transfer wafer to transfer the membrane 3018 to the CMOS substrate 3002. The wafer 3042 may additionally include a substrate or other base layer 3044 and an insulating layer 3046.

Non-limiting examples of suitable transfer wafers are described further below. In general, the second wafer may be any suitable type of wafer, such as a bulk silicon wafer, a silicon-on-insulator (SOI) wafer, or an engineered substrate including a polysilicon or amorphous silicon layer (e.g., membrane 3018) with an insulating layer between a single crystal silicon layer (e.g., substrate 3044) and the polysilicon or amorphous silicon layer. For example, the substrate 3044 may be a bulk silicon substrate and the insulating layer 3046 may be $SiO_2$. The insulating layer 3046 may represent a buried oxide (BOX) layer. The membrane 3018 may be single crystal silicon, polysilicon, or amorphous silicon, as non-limiting examples, and in some embodiments may be doped to provide desired conductivity. In some embodiments, the membrane 3018 may be degeneratively doped, and in some embodiments may be P+ doped. As previously described, the conductive layer 3030, when included, may be formed of TiN as a non-limiting example.

The bonding process used for bonding the CMOS substrate 3002 and the wafer 3042 may be a low temperature bonding process suitable to preserve structures such as silicon circuitry on the CMOS substrate. For example, the bonding may not exceed 450° C. In some embodiments, the temperature of the bonding process may be between approximately 200° C. and 450° C., between approximately 300° C. and approximately 400° C., less than 250° C., any temperature(s) within those ranges, any other temperature described herein for low temperature bonding, or any other suitable temperature. Thus, damage to the metallization layers on the CMOS substrate, and any ICs on the CMOS substrate, may be avoided.

The completed device 3000 of FIG. 30A may be achieved from the structure of FIG. 30G by removing the substrate 3044 and insulating layer 3046. For instance, in some embodiments, the wafer 3042 may be thinned from the backside. Such thinning may be performed in stages. For example, mechanical grinding providing coarse thickness control (e.g., 10 micron control) may initially be implemented to remove a relatively large amount of the bulk wafer (e.g., substrate 3044). In some embodiments, the thickness control of the mechanical grinding may vary from coarse to fine as the thinning process progresses. Then, CMP may be performed on the backside, for example to get to a point close to the membrane 3018. Next, a selective etch, such as a selective chemical etch, may be performed to stop on the membrane 3018. In some embodiments, the membrane 3018 itself may be thinned. Other manners of thinning are also possible.

While FIG. 30A illustrates a non-limiting example of an embodiment of an ultrasonic transducer formed above a top metal layer of a CMOS substrate and suitable for use in ultrasound transducer probes according to one or more embodiments of the present application, it should be appreciated that alternative configurations are possible. Various alternative devices and the processes for fabricating such devices are now described.

Transducer Example 2

Figure 31A:
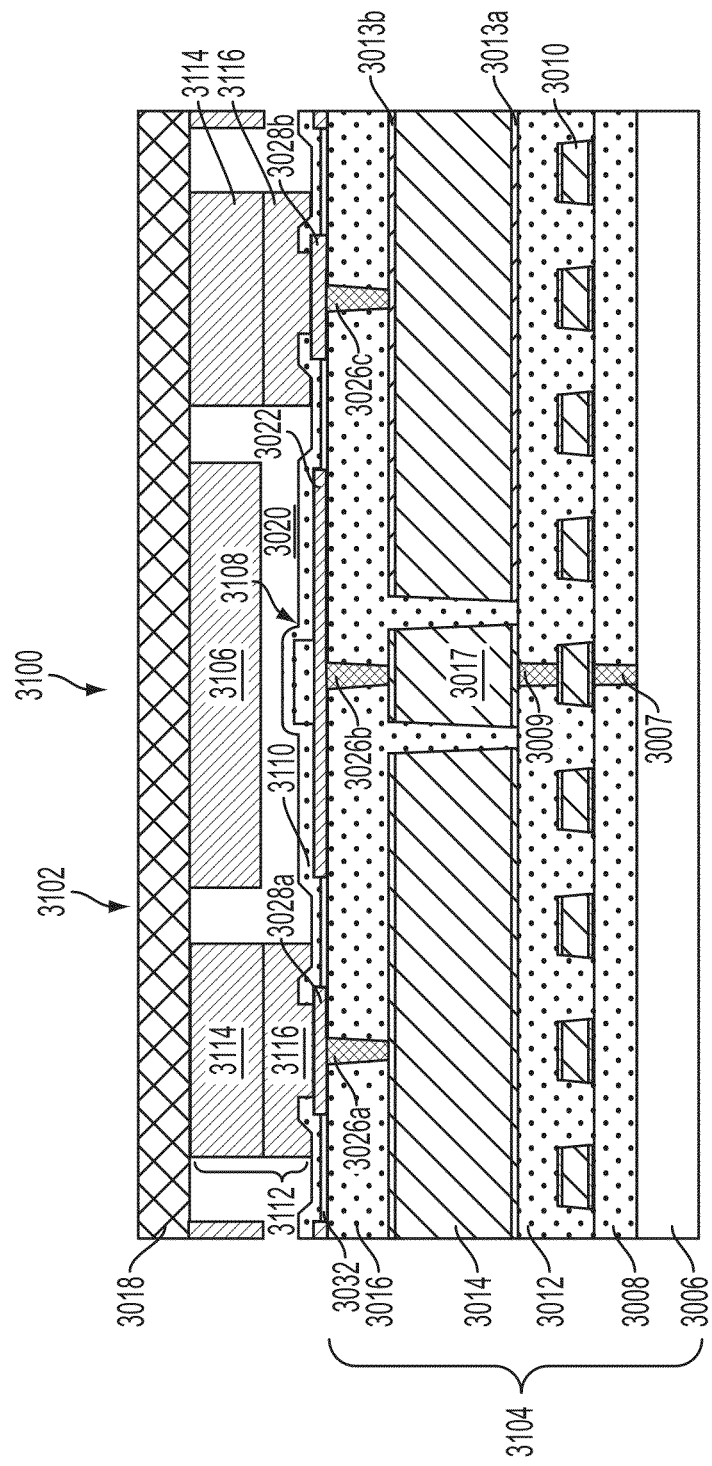
FIGS. 31A-31B illustrate a device including an ultrasonic transducer integrated with a CMOS substrate, formed above a top metal layer of the CMOS substrate, and having a piston membrane and membrane stop, and a method of fabricating the device, according to a non-limiting embodiment of the present application.

FIG. 31A illustrates a device 3100 including an ultrasonic transducer 3102 formed above a top metal layer of a CMOS substrate 3104 and including various optional features in addition to those of the device 3000. For example, the ultrasonic transducer 3102 has a piston configuration. Namely, the ultrasonic transducer 3102 includes a piston membrane including the membrane 3018 with a thick center portion 3106. The piston configuration of the ultrasonic transducer 3102 may be desirable in some embodiments to provide beneficial operating characteristics of the ultrasonic transducer. For example, use of a piston configuration as shown may provide better frequency operation, power characteristics, or other operating characteristics in at least some embodiments. The thickness of the center portion 3106 may be any suitable value for providing such desired operating characteristics. For example, the thickness of the center portion 3106 (including the thickness of membrane 3018) may be between 1 micron and approximately 100 microns, between approximately 10 microns and approximately 50 microns, any value within such ranges, or any other suitable values.

The center portion 3106 may be formed of any suitable material. As a non-limiting example, the center portion 3106 may be formed of TiN. However, other conductive, semiconductor, or insulating materials may be used. In some embodiments, it may be desirable for the center portion 3106 to be formed of a different material than membrane 3018 to allow for the piston membrane to exhibit target behavior with respect to characteristics such as flexibility, capacitive operation, and robustness, among other possible characteristics relevant to operation of the transducer.

In addition, the device 3100 includes a membrane stop 3108. In some embodiments, the membrane stop, which may be formed of any suitable material, such as an insulating material (e.g., $SiO_2$), may function as an isolation post and may provide various benefits. Membrane stops may effectively alter the depth of a cavity such that a membrane may contact the bottom of the cavity (referred to as collapse) more easily, and may alter the frequency behavior of an ultrasonic transducer. Namely, when the membrane is pulled down far enough, it makes contact with the bottom of the cavity. Such operation may be advantageous since having the membrane hit or contact the bottom of the cavity can dampen certain resonant modes, thereby broadening the frequency response of the transducer. However, there is a "charge trapping" effect, in which charge may end up deposited on the electrodes of the transducer, thereby altering the operating characteristics of the transducer (e.g., increasing the necessary bias voltage), and causing hysteresis. Membrane stops may provide the benefit of "bottoming out" the membrane, while substantially reducing the charge trapping effect and problems with hysteresis. Ultrasonic transducers with membrane stops may be more reliable after collapse than ultrasonic devices lacking such membrane stops. Moreover, because the membrane stop may prevent the membrane from contacting the bottom-most part of the cavity, insulation need not be formed on the bottom surface of the cavity in all embodiments, which can therefore reduce processing steps and time in fabricating an ultrasonic transducer. However, the insulator on the bottom surface of the cavity may be used in case of unanticipated contact between the membrane and the bottom of the cavity (despite any membrane stop) and/or to prevent electrical discharge across the cavity.

Membrane stops may be formed in different locations of an ultrasonic transducer. For example, membrane stops may be formed on the bottom of a cavity of an ultrasonic transducer. In some embodiments, membrane stops may be formed on the bottom of a membrane of the ultrasonic transducer (e.g., on the bottom side of a membrane transferred from a transfer wafer). In other embodiments, membrane stops may be formed on both the bottom of a cavity and the bottom of a membrane of an ultrasonic transducer.

The membrane stop 3108 may control how far the membrane 3018 can move relative to the bottom electrode 3022, and may have any suitable thickness for providing such control. For example, the membrane stop 3108 may have a thickness between approximately 5% and 30% of the cavity depth, between approximately 10% and 20% of the cavity depth, or any value within such ranges. An insulating layer 3110, for example formed of $SiO_2$, may substantially cover the membrane stop 3108 in addition to the bottom electrode 3022.

The ultrasonic transducer 3102 also differs from the ultrasonic transducer 3004 in that the conductive spacers 3024 are replaced by conductive spacers 3112 that are formed by multiple distinct portions 3114 and 3116. The conductive spacers 3112 provide electrical connection from the membrane 3018 to the top metal layer 3014 together with the conductive contacts 3028a-3028b and the vias 3026a and 3026c. The portions 3114 and 3116 may be formed of TiN or other suitable conductive materials.

It should be appreciated that the device 3100 therefore represents another example of a device configuration including embedded conductive structures in a CMOS substrate providing electrical connection to the membrane of an ultrasonic transducer.

An example of a process for fabricating the device 3100 is now described. The process may proceed in substantially the same manner as that previously described in connection with device 3000 up to the formation of insulating layer 3032. Then, an insulating layer may be conformally deposited and patterned to form membrane stop 3108. Next, insulating layer 3110 may be deposited and patterned to form openings above the conductive contacts 3028a and 3028b.

A conductive material may then be deposited, patterned and planarized as appropriate to form portion 3116 of the conductive spacers 3112. Surface treatment may be performed as appropriate to prepare the CMOS substrate for bonding to a transfer wafer.

Figure 31B:
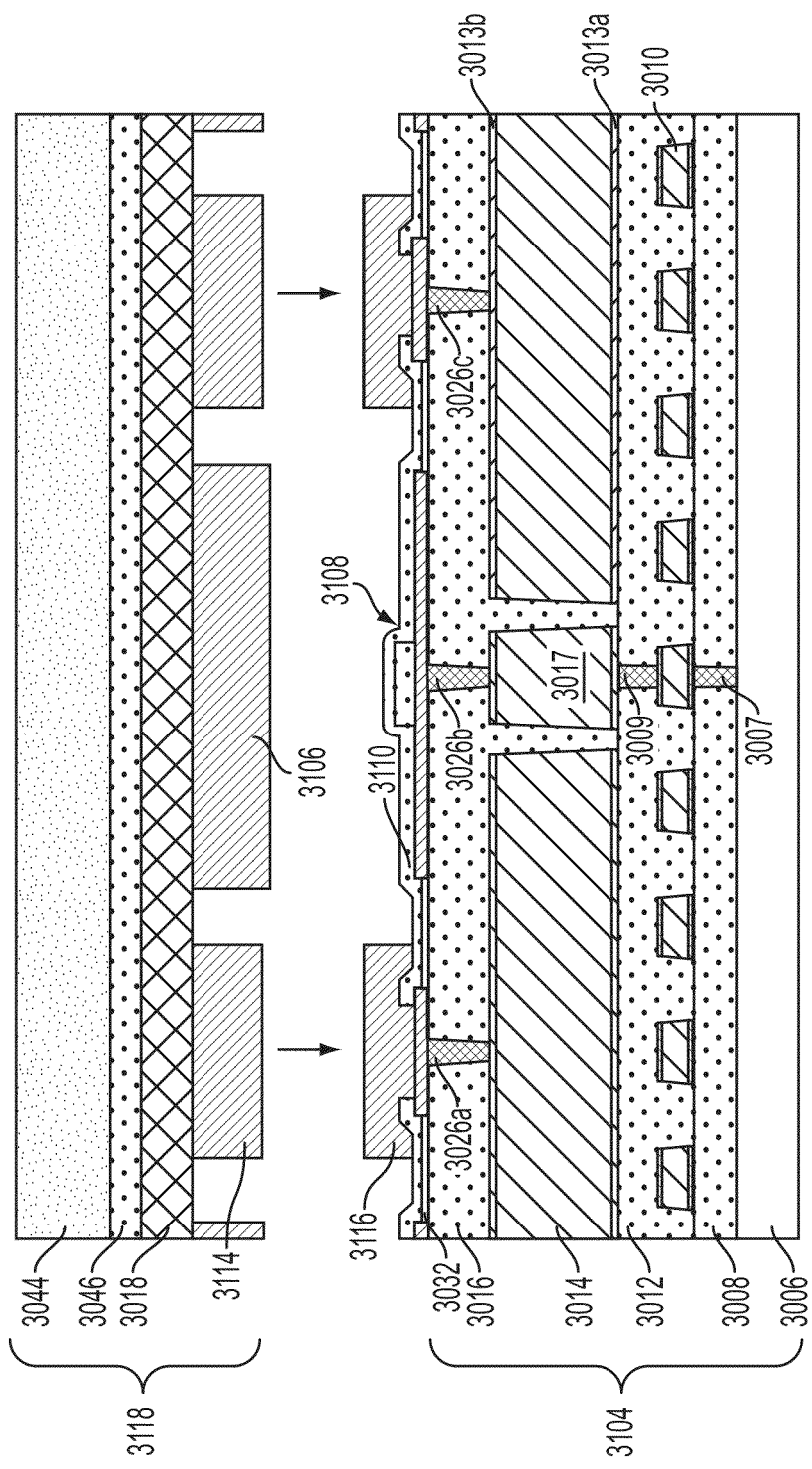

Subsequently, as shown in FIG. 31B, a transfer wafer 3118 may be aligned and bonded with the CMOS substrate 3104. The transfer wafer 3118 may include the portion 3114 and the center portion 3106 of the piston membrane. The bonding may be any type described herein, such as a low temperature bonding.

Then, the wafer 3118 may be processed in any suitable manner to remove the substrate 3044 and insulating layer 3046. For example, any of the techniques described with respect to processing of such layers of the transfer wafer 3042 may be utilized. In this manner, the final structure illustrated in FIG. 31A may be achieved.

Thus, it should be appreciated from FIG. 31A that an embodiment of the present application provides an ultrasonic transducer formed above a top metal layer of a CMOS substrate, in which embedded conductive structures in the CMOS substrate provide electrical contact to the membrane of the ultrasonic transducer.

Transducer Example 3

Figure 32A:
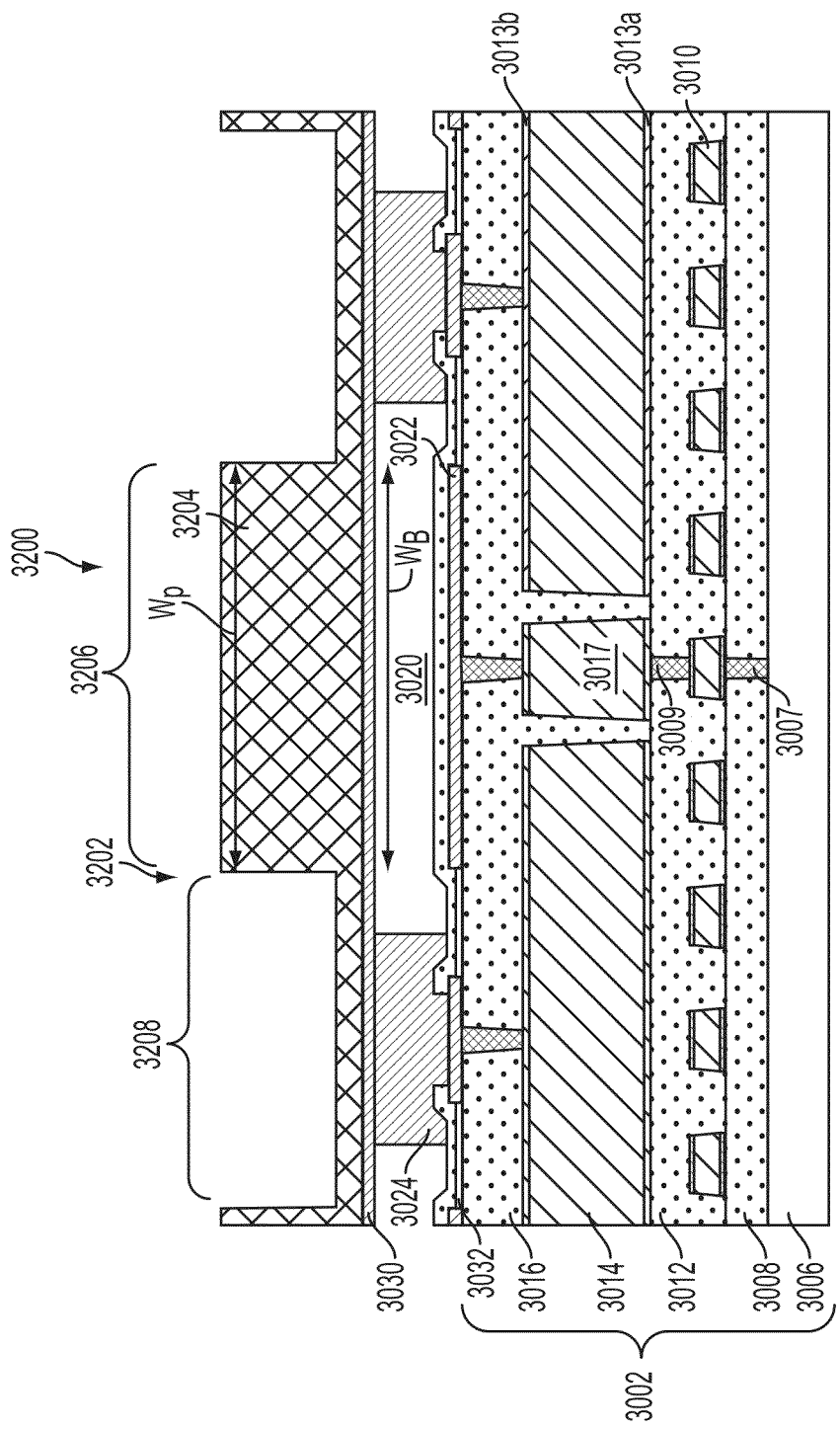
FIGS. 32A-32B illustrate another device including an ultrasonic transducer integrated with a CMOS substrate, formed above a top metal layer of the CMOS substrate, and having a piston membrane, and a method of fabricating the device, according to a non-limiting embodiment of the present application.
Figure 32B:
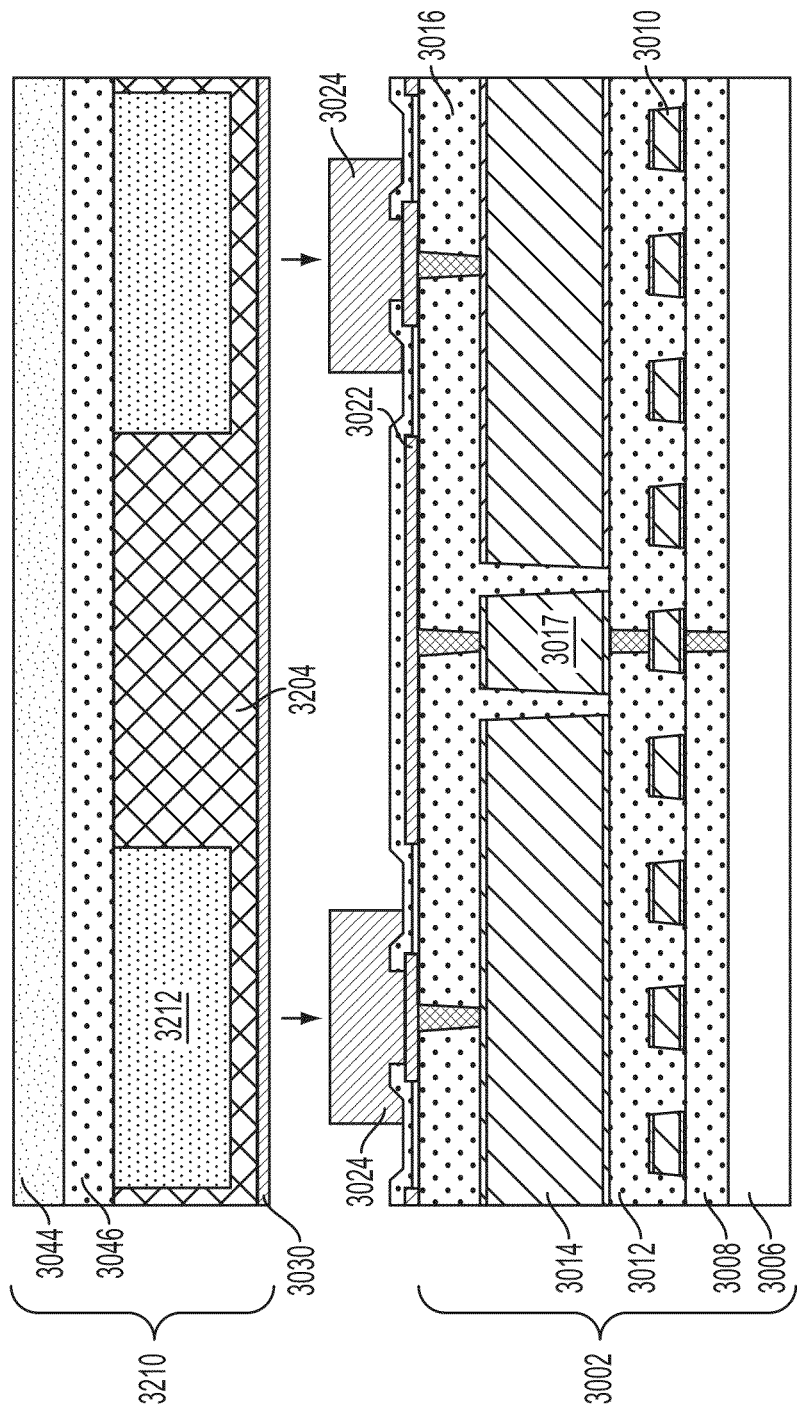

FIG. 32A illustrates an example of another device 3200 having an ultrasonic transducer 3202 formed above the top metal layer 3014 of the CMOS substrate 3002. As shown, the ultrasonic transducer 3202 has a piston membrane configuration. The device 3200 is another example of a device including conductive features embedded in the CMOS substrate to provide electrical connection to the membrane of an ultrasonic transducer.

As shown, the piston membrane 3204 includes a center region 3206 and a peripheral region 3208. The center region 3206 may be thicker than the peripheral region 3208, as illustrated, with the relative thicknesses of the two regions assuming any suitable value to provide desired operation of the ultrasonic transducer 3202.

The piston membrane 3204 may be formed of any suitable material. As a non-limiting example, the piston membrane 3204 may be formed of silicon, which may be doped in some embodiments to provide desired electrical conductivity. For example, in those embodiments in which the piston membrane 3204 is formed of silicon, the silicon may be doped with a positive dopant, such as phosphorus. As also shown, the center region 3206 may have a width Wp substantially corresponding to the width Wb of the bottom electrode 3022, which may provide beneficial capacitive behavior of the ultrasonic transducer. However, alternative configurations are possible.

An example of a process for fabricating the device 3200 is now described. The process may proceed in substantially the same manner as that previously described in connection with formation of device 3000 up through the point illustrated in FIG. 30F. Then, instead of bonding to the transfer wafer 3042 of FIG. 30G, the CMOS substrate may be aligned and bonded with the transfer wafer 3210. The transfer wafer 3210 may include the substrate 3044, the insulating layer 3046, the conductive layer 3030, and an additional insulating layer 3212. The wafer 3210 may also include the piston membrane 3204.

The insulating layer 3212 may be formed of any suitable material. As a non-limiting example, the insulating layer 3212 may be formed of $SiO_2$ or any other suitable dielectric insulating material. In some embodiments, the insulating layer 3212 may be formed via tetraethyl orthosilicate (TEOS), though alternative processes may be used.

The bonding of CMOS substrate 3002 and transfer wafer 3210 may involve any suitable bonding process. For instance, a low temperature bonding process of the types described herein may be utilized.

Subsequently, substrate 3044, insulating layer 3046, and insulating layer 3212 may be removed in any suitable manner to arrive at the structure of FIG. 32A. For example, wafer grinding, etching techniques, or any other suitable removal techniques may be used, such as those described previously for thinning of a wafer, such as wafer 3042.

Devices 3000-3200 represent non-limiting examples of devices including ultrasonic transducers having conductive sidewalls. Several examples of ultrasonic transducers formed on CMOS substrates and having non-conductive sidewalls are now illustrated and described.

Transducer Example 4

Figure 33:
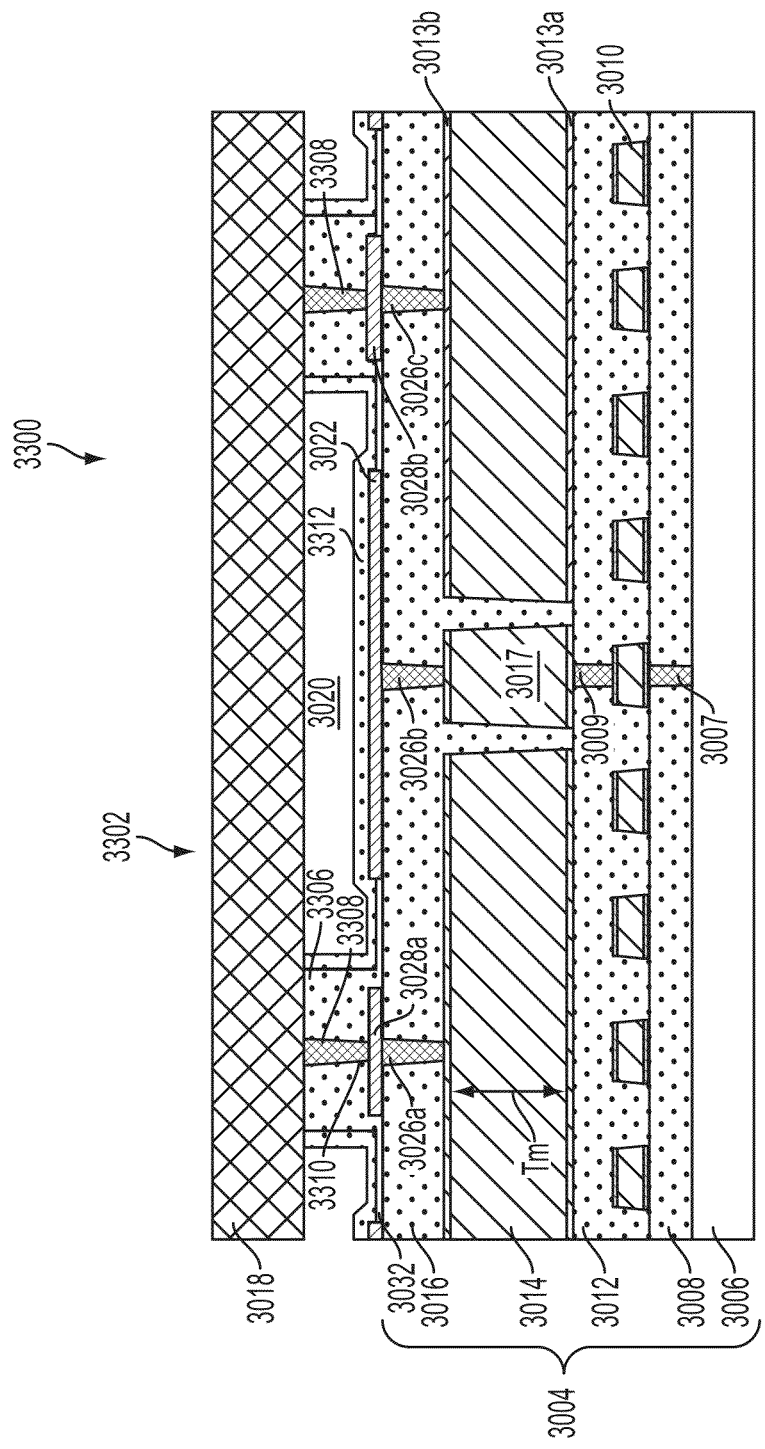
FIG. 33 illustrates another device including an ultrasonic transducer integrated with a CMOS substrate, formed above a top metal layer of the CMOS substrate, and having non-conductive cavity sidewalls, according to a non-limiting embodiment of the present application.

FIG. 33 illustrates a device 3300 including an ultrasonic transducer 3302 formed above a top metal layer of a CMOS substrate 3304. Non-conductive spacers 3306 define a standoff of the membrane 3018 from the bottom of the cavity 3020. Conductive vias 3308 are formed in the non-conductive spacer 3306. A suitable liner 3310 is included to prevent migration of the via material into the non-conductive spacer 3306. For example, the liner 3310 may be formed of TiN or any other suitable conductive lining material. The vias 3308 may be formed of a suitable conductive material, a non-limiting example of which is tungsten. The ultrasonic transducer 3302 also includes an insulating layer 3312 covering the bottom electrode 3022. The non-conductive spacers 3306 and insulating layer 3312 may both be formed of $SiO_2$, as a non-limiting example.

As shown, the membrane 3018 makes direct contact with an upper surface of the via 3308. Thus, an electrical path from the membrane 3018 to the top metal layer 3014 is provided by a combination of via 3308, conductive contact 3028a, and via 3026a.

An example of a process for fabricating the device 3300 is now described. The process may proceed in substantially the same manner as that previously described in connection with the formation of device 3000 up through the point illustrated in FIG. 30D.

Subsequently, an insulating layer may be deposited or otherwise formed and planarized in preparation of forming non-conductive spacers 3306. The insulating layer may be conformally deposited to cover the surface of the CMOS substrate, and then may be patterned to create trenches or other openings for the vias 3308. Then, the liner 3310 may be deposited in the trenches and the trenches filled with conductive material to form the vias 3308. A planarization or etch back may optionally be performed. The insulating layer deposited to form the non-conductive spacers 3306 may then be suitably patterned to form the non-conductive spacers.

Then, insulating layer 3312 may be deposited and the structure may be planarized and treated in preparation for bonding, to remove the insulating layer 3312 from the upper surfaces of the non-conductive spacers 3306. Next, a transfer wafer similar to the transfer wafer 3042, but lacking conductive layer 3030, may be aligned with and bonded to the CMOS substrate 3304. The substrate 3044 and insulating layer 3046 may then be removed to achieve the device 3300.

Transducer Example 5

Figure 34:
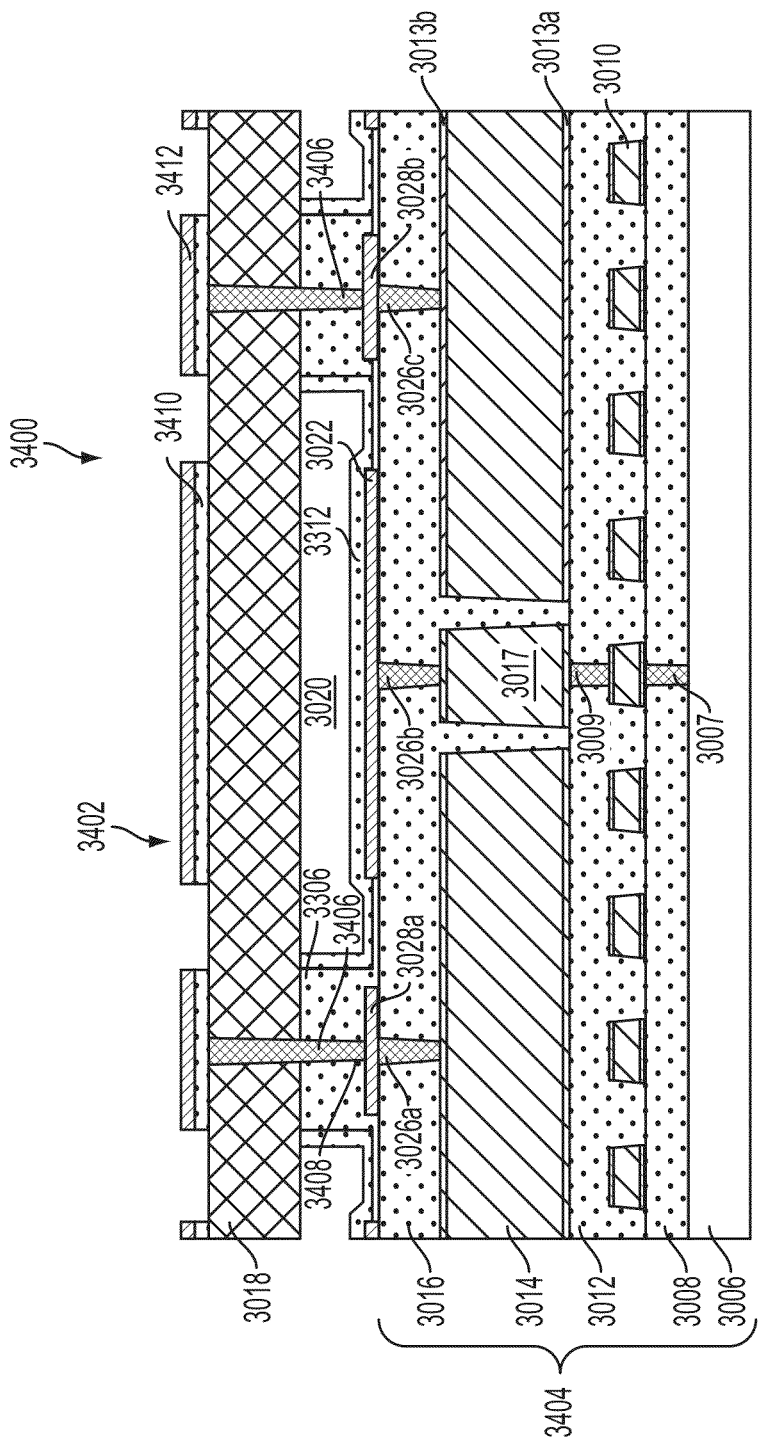
FIG. 34 illustrates another device including an ultrasonic transducer integrated with a CMOS substrate, formed above a top metal layer of the CMOS substrate, and having a conductive via passing through a membrane of the ultrasonic transducer, according to a non-limiting embodiment of the present application.

Another example of a device including an ultrasonic transducer above a top metal layer of a CMOS substrate is illustrated in FIG. 34. As shown, the device 3400 includes an ultrasonic transducer 3402 integrated with a CMOS substrate 3404. Vias 3406, which may be formed of tungsten or other suitable conductive material, pass through the membrane 3018 and the non-conductive spacers 3306 to make contact with the conductive contacts 3028a-3028b. A liner 3408 may be provided and may be the same as previously described liner 3310.

The device 3400 further includes layers 3410 and 3412 which may serve multiple functions in the illustrated embodiment. For instance, the layers 3410 and 3412 may passivate the upper surface of the via 3406. Additionally, the layers 3410 and 3412 may be patterned as shown to create a piston membrane in combination with membrane 3018. The thicknesses of layers 3410 and 3412 may be selected to provide desired operating characteristics to the ultrasonic transducer 3402.

The layers 3410 and 3412 may be formed of any suitable materials, and in some embodiments are formed of insulating materials. For example, layer 3410 may be $SiO_2$ and layer 3412 may be silicon nitride ($Si_3N_4$) according to a non-limiting example. However, alternative passivation materials may be used.

An example of a process for fabricating the device 3400 is now described. The process may proceed in substantially the same manner as that previously described in connection with fabrication of device 3300 except that formation of the vias 3308 may be omitted. Thus, the membrane 3018 may be bonded with the CMOS substrate 3404 without vias in place connecting the membrane 3018 to the conductive contacts 3028a and 3028b. The bonding may be a low temperature bond, for example of the types described previously herein.

Then, after the bonding, the membrane 3018 and non-conductive spacers 3306 may be etched to form trenches which may be lined with liner 3408 and filled with conductive material to form vias 3406. The upper surface of the structure may be planarized as appropriate and layers 3410 and 3412 may be deposited and patterned to arrive at the device 3400.

Transducer Example 6

Figure 35:
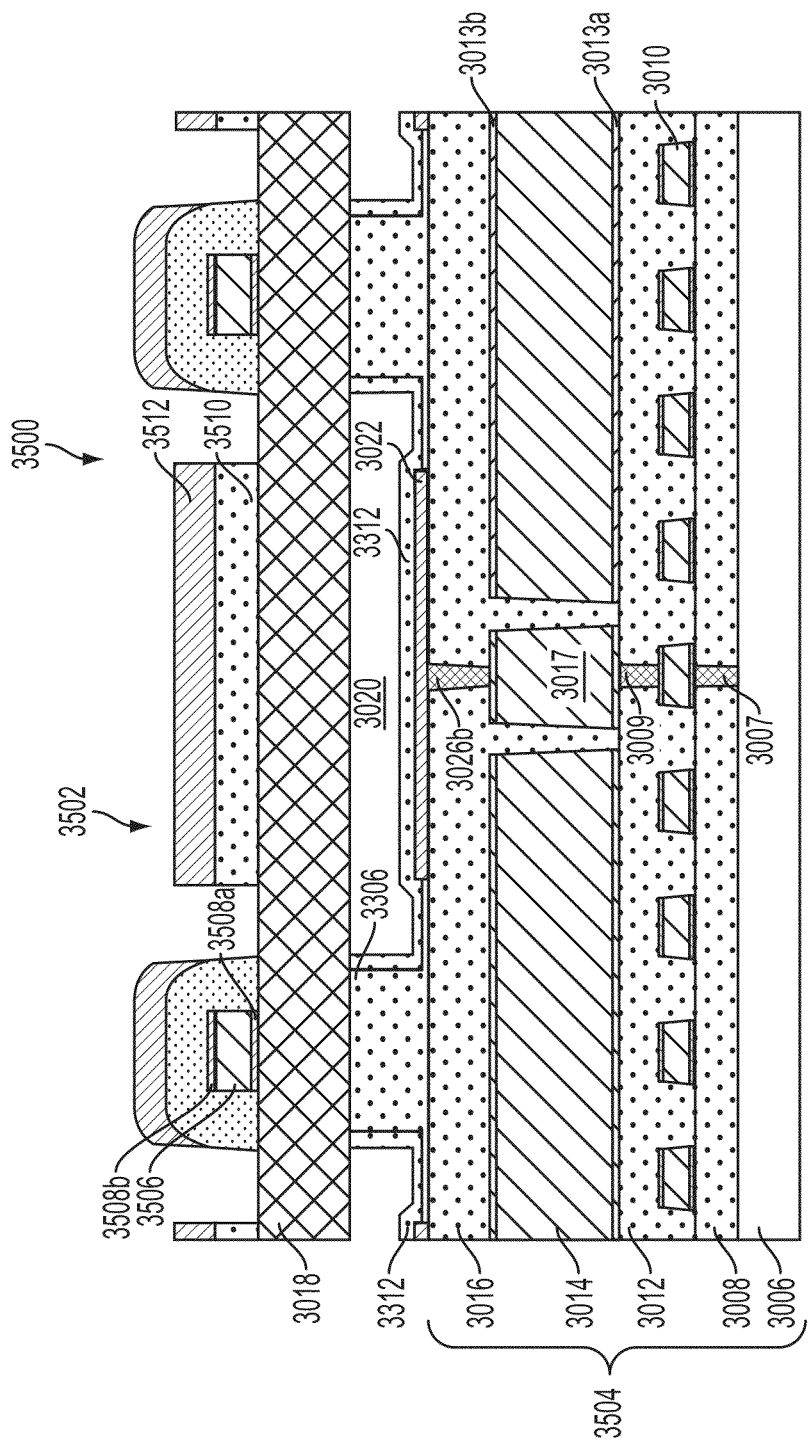
FIG. 35 illustrates another device including an ultrasonic transducer integrated with a CMOS substrate, formed above a top metal layer of the CMOS substrate, and having a topside conductive contact, according to a non-limiting embodiment of the present application.

FIG. 35 illustrates a further example of an ultrasonic transducer integrated with a CMOS substrate and formed above a top metal layer of the CMOS substrate. The device 3500 includes ultrasonic transducer 3502 integrated with CMOS substrate 3504. Device 3500 includes electrical access to the topside of membrane 3018. Namely, contacts 3506 are provided on the topside of the membrane 3018. The contacts may include a metal (e.g., aluminum) or other conductive material, and may include bottom and top liners 3508a and 3508b, respectively. In some embodiments, the liners 3508a and 3508b may be the same as liners 3013a and 3013b.

The contacts 3506 may be passivated with layers 3510 and 3512. Layer 3510 may be the same material as previously described layer 3410 but may be thicker. Layer 3512 may be the same material as previously described layer 3412 but may be thicker. Layers 3510 and 3512 may be patterned as shown to form a piston membrane configuration in combination with membrane 3018.

An example of a process for fabricating the device 3500 is now described. A transfer wafer including the membrane 3018 may be aligned with and bonded to the substrate 3504. Then the transfer wafer may be thinned as desired (e.g., to remove any bulk substrate and buried oxide layer) and the contacts 3506 formed. Layers 3510 and 3512 may then be deposited and patterned in the manner previously described in connection with layers 3410 and 3412 to arrive at the device 3500.

It should be appreciated from the foregoing discussion of examples of ultrasonic transducers integrated with CMOS substrates that the processes used to fabricate such devices may be low temperature processes. The temperatures of all steps performed involving the CMOS substrate once circuit structures are formed on the substrate, including wafer bonding to a transfer wafer, anneals, or other steps, may be kept below temperatures which would cause damage to such circuit components.

Various examples of ultrasonic transducers integrated with a CMOS substrate have been described. It should be appreciated that such devices may have any suitable dimensions. Non-limiting examples of suitable dimensions have been described at least in connection with FIG. 30A, for example for the dimensions of the cavity of the ultrasonic transducer and the thickness of the membrane overlying the cavity. Such dimensions may apply to any of the examples of ultrasonic transducers described herein.

Transfer Wafers

Various examples of transfer wafers have been described herein for use with various embodiments. In some embodiments, traditional SOI wafers may be used, having a silicon bulk wafer as a handle layer, buried oxide layer, and monocrystalline silicon layer. However, as previously described, some embodiments implement alternative types of transfer wafers, including transfer wafers having polysilicon or amorphous silicon layers, for example when such materials are to be used as the membrane 3018. Applicants have appreciated that transfer wafers having such materials may be implemented in some embodiments instead of traditional SOI wafers, and that such alternative types of transfer wafers may be fabricated with significantly less effort and cost than required to form traditional SOI wafers.

Wafers Including Multiple Ultrasonic Transducers

The examples of FIGS. 30A, 31A, 32A, 33, 34, and 35 illustrate a single ultrasonic transducer integrated with a CMOS substrate. It should be appreciated, however, that the ultrasound transducer probes described herein may include more, and in some cases many more, ultrasonic transducers integrated with a CMOS substrate. For example, a single substrate (e.g., a single CMOS wafer) may have tens, hundreds, thousands, tens of thousands, hundreds of thousands, or millions of CUTs formed therein. Formation of such large numbers of ultrasonic transducers on a single substrate may be facilitated by use of the wafer-level processes described herein.

When multiple ultrasonic transducers are formed on a CMOS substrate, they may optionally be electrically interconnected in various manners to form a desired device. For example, multiple ultrasonic transducers may be electrically tied by way of the top metal layer 3014 previously described. Other manners of providing electrical interconnection are also possible.

Forms of Integration of Ultrasonic Transducers with Substrates and Circuitry

While various aspects and embodiments have been described as providing monolithically integrated ultrasonic transducers and CMOS wafers having ICs formed therein, not all aspects and embodiments are limited in this respect. For example, some aspects of the present application may also apply to flip-chip bonded and multi-chip configurations. For example, making electrical contact to the bottom side of a membrane may be performed in flip-chip bonded configurations. Other aspects may also apply to non-monolithic devices.

Figure 36:
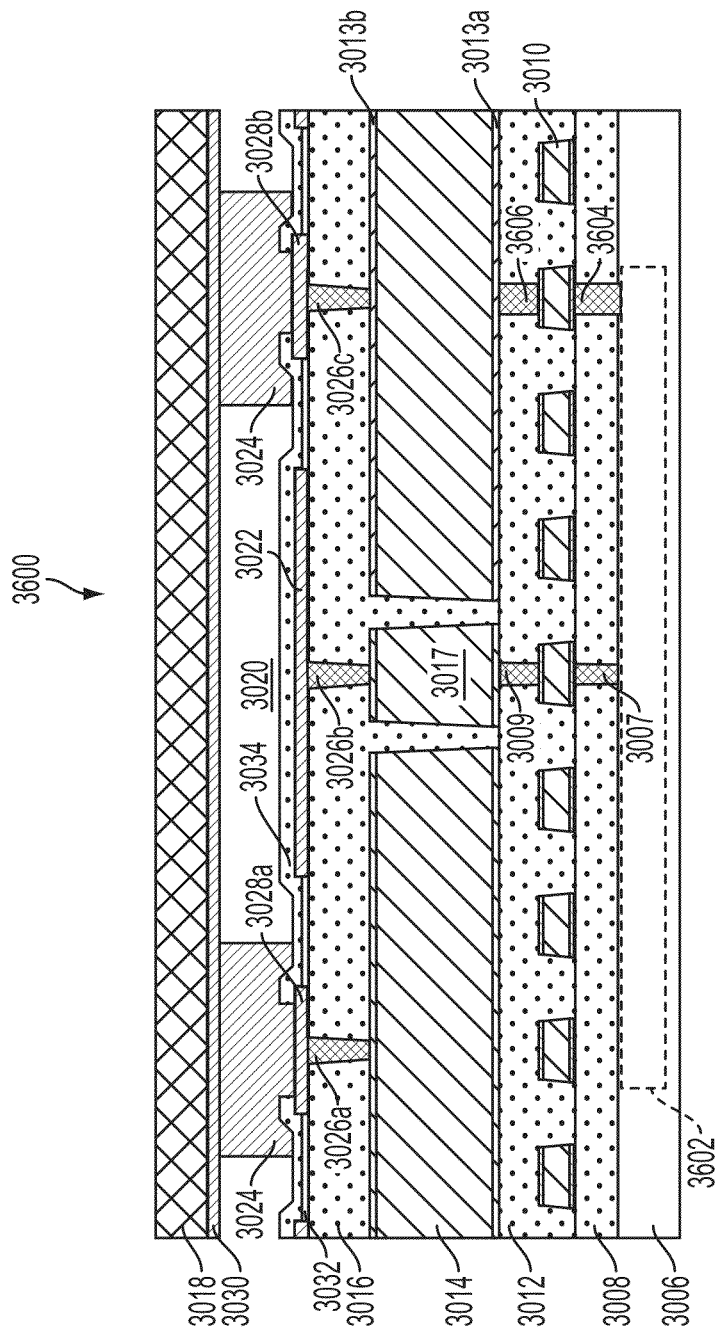
FIG. 36 illustrates a device including the ultrasonic transducer of FIG. 30A connected to an integrated circuit in the CMOS substrate, with the integrated circuit disposed beneath the ultrasonic transducer.

As described previously, an aspect of the present application provides an ultrasonic transducer cell integrated with CMOS circuitry where the circuitry is disposed beneath the transducer. FIG. 36 illustrates a non-limiting example of a such a device, using the ultrasonic transducer of FIG. 30A.

As shown, the device 3600 may include the ultrasonic transducer of FIG. 30A with the addition of an integrated circuit 3602. The integrated circuit may be formed in the substrate 3006 of the CMOS wafer. For example, the substrate may be a bulk silicon wafer, and the integrated circuit 3602 may include one or more active silicon circuit elements (e.g., MOS transistors having doped source and drain regions in the silicon), capacitors, resistors, or other circuit components. The integrated circuit 3602 may be suitable to operate the ultrasonic transducer in transmit and/or receive modes.

As shown, both the electrode 3022 and the conductive contacts 3028a and 3028b may be connected to the integrated circuit 3602, for example by respective vias. For instance, the electrode 3022 may be connected to the integrated circuit 3602 by vias 3007, 3009, and 3026b. The conductive contact 3028b may be connected to the integrated circuit 3602 by vias 3604, 3606, and 3026c. The via connecting the electrode 3022 may, for example, directly contact a doped source/drain terminal of a MOS transistor in the substrate 3006.

As shown in FIG. 36, in some embodiments local connection may be made to the membrane of an ultrasonic transducer rather than global connection. For example, conductive contacts 3028a and 3028b provide for local connection to the membrane 3018 of the illustrated ultrasonic transducer.

In some embodiments, the membrane of the ultrasonic transducer may be biased. In such situations, the membrane may be connected to the integrated circuit 3602 via a capacitor (not shown) for providing or maintaining a desired bias level. Other biasing configurations are also possible.

In some embodiments, the electrode 3022 may be driven, and thus the integrated circuit 3602 may be suitably connected to drive the electrode 3022. In some embodiments, the electrode 3022 may be biased, rather than the membrane.

Transducer Fabrication Technology

The various non-limiting examples of ultrasonic transducers fabricated on CMOS substrates described herein may be fabricated with any suitable feature sizes. According to an embodiment, 0.18 micron technology may be utilized for fabricating such ultrasonic transducers. In some embodiments, 0.13 micron technology may be used. In some embodiments, 90 nm fabrication technology may be used. In some embodiments, 0.35 micron technology may be utilized. Other feature sizes may be used, as those listed represent non-limiting examples.

Various non-limiting examples of ultrasonic transducers which may be used in an ultrasound transducer probe according to one or more aspects of the present application have been described. It should be appreciated, however, that not all aspects of the present application are limited to using such ultrasonic transducers.

The illustrated examples of devices 3000, 3100, 3200, 3300, 3400, and 3500 have been described primarily as utilizing aluminum metal processing techniques. However, other techniques of forming ultrasonic transducers integrated with CMOS substrates may alternatively be used. For example, copper processing techniques, such as damascene or dual damascene processing may be used in some embodiments. For such processing, the interlayer dielectrics used may include $SiO_2$ or other low-K materials, where K represents the dielectric constant. Barrier layers used in combination with copper metallization may include tantalum (Ta), tantalum nitride (TaN), and TiN. Thus, according to aspects of the present application an integrated device may include one or more ultrasonic transducers integrated with a CMOS substrate including CMOS integrated circuitry having copper metallization, and formed using damascene or dual damascene processing.

In some embodiments, a combination of aluminum processing and copper processing techniques may be implemented. For example, referring to the device 3000, the underlying CMOS substrate may be formed using copper-based dual damascene processes. The top metal layer 3014 may be aluminum or aluminum-copper. Thus, a combination of copper processing techniques and aluminum processing techniques may be utilized to fabricate such devices.

Process

As described previously, aspects of the present application provide an ultrasound transducer probe which may be tiled and interconnected by suitably replicating the ultrasound transducer probe. According to some aspects, such replication may be performed using a common photolithography mask or reticle with appropriate stepping and/or scanning functions. Various examples are now described.

Figure 38:
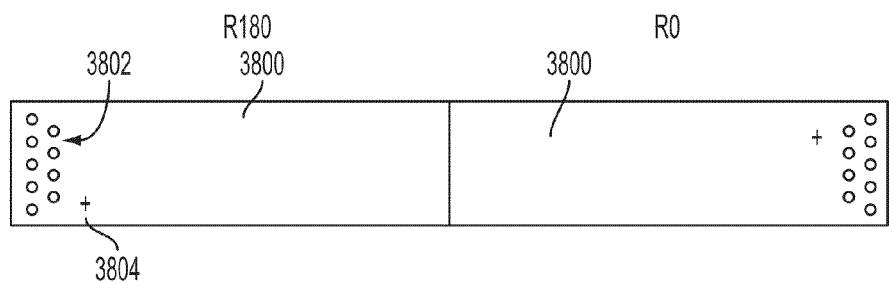
FIG. 38 illustrates the use of a reticle to perform horizontal tiling of an ultrasound transducer probe, according to a non-limiting embodiment of the present application.

According to an aspect of the present application, an ultrasound transducer probe may be fabricated by suitably rotating and printing a pattern from a photolithography mask (also referred to herein as a "pattern mask") to create two side-by-side (or horizontally tiled) instances of the pattern. Referring to FIG. 38, a reticle 3800 may have a pattern formed thereon.

The pattern may include features at least partially defining processing circuitry of an ultrasound transducer probe and ultrasonic transducers of the ultrasound transducer probe. As an example, the features may at least partially define I/O circuitry on a side or periphery of the ultrasound transducer probe, for example consistent with the configuration of previously described ultrasound transducer probe 200 of FIG. 2A. More specifically, the reticle 3800 may be a reticle used to fabricate the ultrasound transducer probe 200 in a non-limiting embodiment. The features 3802 may at least partially define I/O circuitry of the ultrasound transducer probe. The pattern on the reticle may also include an alignment mark 3804.

An ultrasound transducer probe of the type 220 illustrated in FIG. 2C may be fabricated by printing the pattern from the reticle 3800 twice. For example, the pattern from the reticle may be printed on a wafer a first time (by illuminating the reticle), indicated as R0. The wafer may then be rotated and aligned with the already-printed pattern, and the pattern from the reticle 3800 may again be printed on the wafer (by again illuminating the reticle), indicated as R180. Alternatively, the reticle may be rotated (rather than the wafer), or both the reticle and wafer may be rotated. In some embodiments, printing the reticle pattern at the position of R0 may involve printing the odd fields of the pattern and printing the reticle pattern at the position R180 may involve printing the even fields of the pattern. However, alternative manners of operation are possible. By suitably rotating and printing the reticle pattern, as described, a double-wide ultrasound transducer probe (e.g., ultrasound transducer probe 220) may be fabricated from a single reticle.

Figure 39:
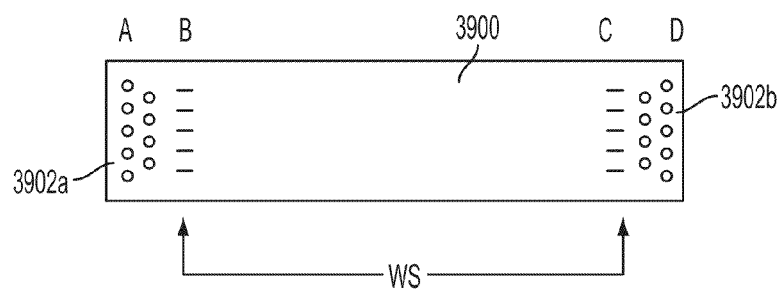
FIG. 39 illustrates a reticle having features at least partially defining input/output (I/O) circuitry of an ultrasound transducer probe on opposing sides of the reticle, according to a non-limiting embodiment of the present application.

Another manner of horizontally tiling ultrasound transducer probes of the types described herein involves printing portions of a reticle in alignment with each other, and is described in connection with FIGS. 39-41. FIG. 39 illustrates a reticle 3900 having features at least partially defining I/O circuitry 3902a and 3902b on opposite sides of the reticle. The reticle pattern may also include features between positions B and C for defining, at least in part, ultrasonic transducers of an ultrasound transducer probe. In some embodiments, the reticle pattern may be substantially uniform over the distance WS in the width direction. It should be appreciated that the reticle 3900 may be suitable for use in fabricating an ultrasound transducer probe of the type 210 of FIG. 2B.

The reticle 3900 may be considered to have multiple portions defined by the positions A-D. For example, position A to B represents a portion, position A to C another portion, position B to C another portion, position B to D another portion, and so on for all combinations of positions A-D. Printing appropriate portions and aligning them may result in creation of an ultrasound transducer probe. Alignment marks may be provided at the positions A-D to facilitate printing of the portions and aligning them.

Figure 40:
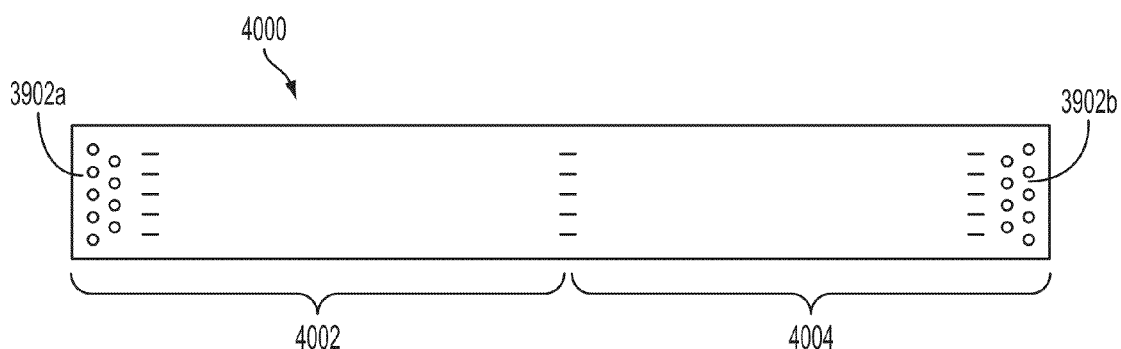
FIGS. 40 and 41 illustrate ultrasound transducer probes that can be formed by horizontal tiling of a photolithography mask pattern, according to non-limiting embodiments of the present application.

The double-wide ultrasound transducer probe 4000 of FIG. 40 may be printed by printing and aligning portions of the pattern of reticle 3900 of FIG. 39. In one photolithography printing step, a first portion of the pattern of reticle 3900 may be printed from position A to position C (see FIG. 39) by scanning the reticle 3900 from position A to position C. The result is shown as pattern 4002 in FIG. 40. When scanning the reticle 3900 from position A to position C, the features to the right of position C in FIG. 39 may be obstructed, for example using blading techniques.

Next, the reticle 3900 may be stepped such that position B on the reticle aligns with position C on the printed pattern. A second portion of the reticle 3900 may then be scanned from position B to position D. The result is shown as pattern 4004 in FIG. 40.

Thus, it should be appreciated that the ultrasound transducer probe 4000 may include I/O circuitry on opposing ends and a central region comprising ultrasonic transducers. Also, such horizontal tiling may be achieved with a single photolithographic mask, thus greatly simplifying the process and cost compared to if multiple masks were used.

Figure 41:
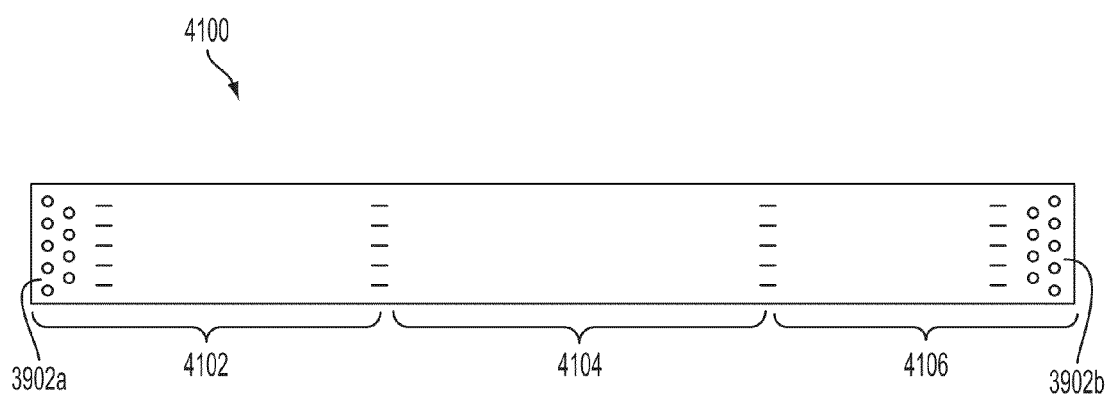

FIG. 41 illustrates an ultrasound transducer probe 4100 which may be formed by horizontally tiling three instances of the reticle pattern from reticle 3900 of FIG. 39. At a first stage of processing, a first portion of the reticle 3900 may be scanned from position A to position C. The result is shown as 4102. Subsequently, the reticle may be stepped such that position B on the reticle aligns with position C on the printed pattern. A second portion of the reticle 3900 may then be scanned from position B to position C. The result is shown as 4104. The reticle 3900 may then be stepped again such that position B on the reticle aligns with position C on the printed pattern 4104. A third portion of the reticle may then be scanned from position B to position D. The result is shown as 4106. In this manner, a three-wide ultrasound transducer probe may be formed from a single reticle. It should be appreciated that additional instances of the ultrasound transducer probe layout corresponding to reticle 3900 may be horizontally tiled by utilizing a similar methodology and adding in additional scans from position B to position C.

When scanning only a portion of a reticle (e.g., from position A to position C of reticle 3900, from position B to position C of reticle 3900, and from position B to position D of reticle 3900), blading techniques or other suitable techniques may be used to obstruct or otherwise avoid printing undesired portions of the reticle pattern.

It should be appreciated from the foregoing that multiple instances of an ultrasound transducer probe may be horizontally tiled on a wafer to form an ultrasound transducer probe of desired dimensions using a common reticle. Vertical tiling may be accomplished by stepping the reticle vertically and suitably aligning it. Thus, multiple instances of an ultrasound transducer probe may be tiled horizontally and/or vertically.

Moreover, it should be appreciated that blading techniques may be used to facilitate tiling of ultrasound transducer probes having peripheral regions on the top and/or bottom side of the transducer probe while still providing a contiguous region of ultrasonic transducers. For example, peripheral regions of an ultrasound transducer probe located on the top and bottom sides of the transducer probe and having only contact pads may be vertically tiled while still creating a contiguous region of ultrasonic transducers by blading one or more of such peripheral regions.

CONCLUSION

The aspects of the present application may provide one or more benefits, some of which have been previously described. Now described are some non-limiting examples of such benefits. It should be appreciated that not all aspects and embodiments necessarily provide all of the benefits now described. Further, it should be appreciated that aspects of the present application may provide additional benefits to those now described.

Some aspects of the present application provide ultrasound transducer probes which are configured to be tiled and interconnected, thus providing an ultrasound probe designer great flexibility in designing an ultrasound probe of choice by mere replication and suitable placement of a common building block ultrasound unit. Some aspects provide ultrasound transducer probes which are connectable to different types of external devices via different physical interfaces, thus increasing usability and accessibility of the devices. Some aspects provide an ultrasound transducer probe that is configurable to operate in various modes, including various ultrasound imaging modes. In some aspects, the ultrasound transducer probes may be highly integrated, including ultrasound transducers and ICs monolithically integrated on a common substrate, providing a compact form factor.

Ultrasound transducer probes according to aspects of the present application may be worn, and used in-situ. Thus, the usefulness of such devices may be greater than conventional ultrasound probes.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present application involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present application need not reside on a single computer or processor, but may be distributed in a modular fashion among a number of different computers or processors to implement various aspects of the present application.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks or wired networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Elements other than those specifically identified by the "and/or" clause may optionally be present, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the term "between" is to be inclusive unless indicated otherwise. For example, "between A and B" includes A and B unless indicated otherwise.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. An apparatus, comprising:
a semiconductor chip including a silicon substrate, a plurality of insulating layers formed on the silicon substrate, and a metal layer between two insulating layers of the plurality of insulating layers, wherein the metal layer is connected to the silicon substrate by a conductive via passing through an insulating layer of the plurality of insulating layers, the semiconductor chip having a device surface with a width and height, the width of the device surface being at least twice as large as the height of the device surface, the metal layer having a thickness between 0.5 microns and 10 microns, wherein the width, the height, and the thickness are orthogonal to each other;
a plurality of complementary metal oxide semiconductor (CMOS) ultrasonic transducers integrated on the plurality of insulating layers, wherein at least one CMOS ultrasonic transducer of the plurality of CMOS ultrasonic transducers is disposed above the metal layer such that the metal layer is between the silicon substrate and the at least one CMOS ultrasonic transducer; and
CMOS control circuitry formed in the silicon substrate, coupled to the plurality of CMOS ultrasonic transducers by at least one conductive via passing through the insulating layer of the plurality of insulating layers and configured to control the plurality of CMOS ultrasonic transducers to support one-dimensional (1D), two-dimensional (2D), and three-dimensional (3D) ultrasound imaging,
wherein the CMOS control circuitry comprises a waveform generator coupled to the at least one CMOS ultrasonic transducer of the plurality of CMOS ultrasonic transducers through a pulser, the waveform generator configurable to generate an impulse, a continuous wave, a coded excitation, and a chirp waveform;
wherein the waveform generator comprises a plurality of registers, wherein the plurality of registers comprises a register storing a value of an initial phase, a register storing a value of an initial frequency, and a register storing a value of a frequency rate of change; and
wherein the waveform generator further comprises a plurality of comparators and a plurality of multiplexers, wherein outputs of the plurality of registers are coupled to inputs to the plurality of comparators, and wherein outputs of the plurality of comparators are coupled to inputs of the multiplexers, an output of a first multiplexer of the plurality of multiplexers being a first input to the pulser, and an output of a second multiplexer of the plurality of multiplexers being a second input to the pulser.

2. The apparatus of claim 1, wherein the plurality of CMOS ultrasonic transducers and the CMOS control circuitry represent multiple instances of an ultrasound probe tiled on the silicon substrate.

3. The apparatus of claim 1, wherein the CMOS control circuitry is configured to control the at least one CMOS ultrasonic transducers of the plurality of CMOS ultrasonic transducers to provide high intensity focused ultrasound (HIFU).

4. The apparatus of claim 1, wherein the plurality of CMOS ultrasonic transducers is a first plurality of CMOS ultrasonic transducers, and wherein the apparatus further comprises a second plurality of CMOS ultrasonic transducers configured to provide high intensity focused ultrasound (HIFU).

5. The apparatus of claim 1, wherein the pulser is a tri-level pulser.

6. The apparatus of claim 1, wherein the pulser is configured to provide voltage pulses to the at least one CMOS ultrasonic transducer of the plurality of CMOS ultrasonic transducer having voltages between 30 Volts and 120 Volts.

7. The apparatus of claim 1, wherein the chirp waveform is a linear frequency modulation (LFM) chirp.

8. The apparatus of claim 1, wherein a ratio of the width of the device surface to the height of the device surface is between 5:1 and 10:1.

9. The apparatus of claim 1, wherein the plurality of CMOS ultrasonic transducers covers more than half of the height of the device surface and less than the width of the device surface, and wherein at least a first portion of the CMOS control circuitry is formed on a peripheral region of the width of the device surface not covered by the plurality of CMOS ultrasonic transducers.

10. The apparatus of claim 1, wherein the at least one CMOS ultrasonic transducer of the plurality of CMOS transducers comprises a membrane, and wherein the membrane is connected to the metal layer by an electrically conductive via.

11. The apparatus of claim 1, further comprising a wiring line in the silicon substrate, wherein the at least one CMOS ultrasonic transducer of the plurality of CMOS ultrasonic transducers comprises an electrode, and wherein the metal layer is configured as an electrical shield between the electrode and the wiring line.

12. The apparatus of claim 1, wherein the CMOS control circuitry includes a sequence processor configured to store a program controlling a sequence of operations executed by the plurality of CMOS ultrasonic transducers.

13. The apparatus of claim 1, wherein the CMOS control circuitry comprises a sequence processor configured to operate the plurality of CMOS ultrasonic transducers semi-autonomously.

14. The apparatus of claim 1, wherein the plurality of CMOS ultrasonic transducers are arranged in groups connected in a daisy-chain configuration by data lines.

15. The apparatus of claim 1, further comprising time-gain compensation circuitry coupled to the plurality of CMOS ultrasonic transducers.

* * * * *